United States Patent
Orlando et al.

(10) Patent No.: US 11,648,335 B2
(45) Date of Patent: May 16, 2023

(54) ORGAN/TISSUE DECELLULARIZATION, FRAMEWORK MAINTENANCE AND RECELLULARIZATION

(71) Applicant: WAKE FOREST UNIVERSITY HEALTH SCIENCES, Winston-Salem, NC (US)

(72) Inventors: Giuseppe Orlando, Winston-Salem, NC (US); Shay Soker, Greensboro, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 0 days.

(21) Appl. No.: 14/610,902

(22) Filed: Jan. 30, 2015

(65) Prior Publication Data

US 2015/0238656 A1 Aug. 27, 2015

Related U.S. Application Data

(60) Provisional application No. 61/934,429, filed on Jan. 31, 2014.

(51) Int. Cl.
*A61L 27/36* (2006.01)
*A61L 27/38* (2006.01)
*A61L 27/54* (2006.01)

(52) U.S. Cl.
CPC ....... *A61L 27/3633* (2013.01); *A61L 27/3604* (2013.01); *A61L 27/3687* (2013.01); *A61L 27/3808* (2013.01); *A61L 27/3834* (2013.01); *A61L 27/54* (2013.01); *A61L 2300/256* (2013.01); *A61L 2300/42* (2013.01); *A61L 2430/26* (2013.01); *A61L 2430/28* (2013.01); *A61L 2430/40* (2013.01)

(58) Field of Classification Search
CPC ............. A61L 2430/40; A61L 2430/28; A61L 2430/26; A61L 27/3604; A61L 27/3633; A61L 27/3687; A61L 27/3808; A61L 27/3834; A61L 27/54
See application file for complete search history.

(56) References Cited

U.S. PATENT DOCUMENTS

| | | |
|---|---|---|
| 4,946,778 A | 8/1990 | Ladner et al. |
| 5,225,539 A | 7/1993 | Winter |
| 5,403,484 A | 4/1995 | Ladner et al. |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,639,641 A | 6/1997 | Pedersen et al. |
| 5,693,761 A | 12/1997 | Queen et al. |
| 5,693,762 A | 12/1997 | Queen et al. |
| 5,702,892 A | 12/1997 | Mulligan-Kehoe |
| 5,714,352 A | 2/1998 | Jakobovits |
| 5,780,279 A | 7/1998 | Matthews et al. |
| 5,821,047 A | 10/1998 | Garrard et al. |
| 5,824,520 A | 10/1998 | Mulligan-Kehoe |
| 5,837,500 A | 11/1998 | Ladner et al. |
| 5,855,885 A | 1/1999 | Smith et al. |
| 5,858,657 A | 1/1999 | Winter et al. |
| 5,871,907 A | 2/1999 | Winter et al. |
| 5,969,108 A | 10/1999 | McCafferty et al. |
| 6,057,098 A | 5/2000 | Buechler et al. |
| 6,225,447 B1 | 5/2001 | Winter et al. |
| 6,265,150 B1 | 7/2001 | Terstappen et al. |
| 2002/0197266 A1 | 12/2002 | Debinski |
| 2005/0282233 A1 | 12/2005 | Eriksson et al. |
| 2009/0191608 A1* | 7/2009 | Matsumoto .......... C12N 5/0676 435/212 |

FOREIGN PATENT DOCUMENTS

| | | |
|---|---|---|
| EP | 0239400 B1 | 8/1994 |
| GB | 2188638 A | 10/1987 |
| WO | WO-2005/087812 A1 | 9/2005 |
| WO | WO-2007/025233 A1 | 3/2007 |

OTHER PUBLICATIONS

Baptista et al. "Decellularization methods of porcine kidneys for whole organ engineering using a high-throughput system" Biomaterials 33 (2012) 7756-7764.*
Abbasoglu, Liver transplantation: yesterday, today and tomorrow, *World J. Gastroenterol.* 14(20): 3117-22 (2008).
Abt et al., Survival following liver transplantation from non-heart-beating donors, *Ann. Surg.* 239(1): 87-92 (2004).
Amann et al., Therapeutic window of MuS110, a single-chain antibody construct bispecific for murine EpCAM and murine CD3, *Cancer Res.* 68(1): 143-51 (2008).
American Diabetes Association, Diagnosis and classification of diabetes mellitus, *Diabetes Care*, 32(Suppl 1): S62-S67 (2009).
American Diabetes Association, Economic costs of diabetes in the U.S. in 2012, *Diabetes Care*, 36: 1033-46 (2013).
Arbiser et al., Oncogenic H-ras stimulates tumor angiogenesis by two distinct pathways, *Proc. Natl. Acad. Sci. USA*, 94(3): 861-6 (1997).
Arenas-Herrera et al., Decellularization for whole organ bioengineering, *Biomed. Mater.* 8(1): 014106 (2013).
Arruebo et al., Antibody-conjugated nanoparticles for biomedical applications, *J. Nanomater.* 2009: 1-24 (2009).
Atala et al., Engineering complex tissues, *Sci. Transl. Med.* 4(160): 160rv12 (2012).
Atala et al., Tissue-engineered autologous bladders for patients needing cystoplasty, *Lancet*, 367: 1241-6 (2006).

(Continued)

*Primary Examiner* — Blaine Lankford
(74) *Attorney, Agent, or Firm* — Marshall, Gerstein & Borun LLP

(57) ABSTRACT

Methods for decellularizing organs and tissues in vitro and in vivo are provided, as are methods of maintaining organ and tissue frameworks and methods of recellularizing organs and tissues, thereby providing an approach to needed organs or tissues.

17 Claims, 44 Drawing Sheets

(56) References Cited

OTHER PUBLICATIONS

Atala, Organ preservation, organ and cell transplantation, tissue engineering, and regenerative medicine: the terms may change, but the goals remain the same, *Tissue Eng. Part A*, 20: 445-6 (2014).
Bach et al., Genetics of transplantation: the major histocompatibility complex, *Annu. Rev. Genet.* 10: 319-39 (1976).
Badylak et al., Engineered whole organs and complex tissues, Lancet <http://www.ncbi.nlm.nih.gov.go.libproxy.wfubmc.edu/pubmed?term=macchiarini%20badylak>. 379(9819): 943-52 (2012).
Badylak et al., Whole-organ tissue engineering: decellularization and recellularization of three-dimensional matrix scaffolds, *Annu. Rev. Biomed. Eng.* 13: 27-53 (2011).
Baiguera et al., Chorioallantoic membrane for in vivo investigation of tissue-engineered construct biocompatibility, *J. Biomed. Mater. Res. B. Appl. Biomater.* 100(5): 1425-34 (2012).
Baptista et al., The use of whole organ decellularization for the generation of a vascularized liver organoid, *Hepatology*, 53(2): 604-17 (2011).
Barakat et al., Use of decellularized porcine liver for engineering humanized liver organ, *J. Surg. Res.* 173(1): e11-25 (2012).
Bissell et al., How does the extracellular matrix direct gene expression? *J. Theor. Biol.* 99(1): 31-68 (1982).
Bonandrini et al., Recellularization of well-preserved acellular kidney scaffold using embryonic stem cells, *Tissue Eng. Part A*, 20(9-10): 1486-98 (2014).
Boyle et al., Projection of the year 2050 burden of diabetes in the US adult population: dynamic modeling of incidence, mortality, and prediabetes prevalence, *Popul. Health Metr.* 8: 29 (2010).
Brien et al., Protection by immunoglobulin dual-affinity retargeting antibodies against dengue virus, *J. Virol.* 87(13): 7747-53 (2013).
Brischwein et al., MT110: a novel bispecific single-chain antibody construct with high efficacy in eradicating established tumors, *Mol. Immunol.* 43(8): 1129-43 (2006).
Brody et al., Aptamers as therapeutic and diagnostic agents, *J. Biotechnol.* 74(1): 5-13 (2000).
Casavilla et al., Experience with liver and kidney allografts from non-heart-beating donors, *Transplantation*, 59(2): 197-203 (1995).
Chazan et al., The clinical spectrum of renal osteodystrophy in 57 chronic hemodialysis patients: a correlation between biochemical parameters and bone pathology findings, *Clin. Nephrol.* 35(2): 78-85 (1991).
Choi et al., Development of a porcine renal extracellular matrix scaffold as a platform for kidney regeneration, *J. Biomed. Mater. Res. A.* 103(4): 1391-403 (2015).
Chung et al., Bladder reconstitution with bone marrow derived stem cells seeded on small intestinal submucosa improves morphological and molecular composition, *J. Urol.* 174(1): 353-9 (2005).
Cioffi et al., EpCAM/CD3-Bispecific T-cell engaging antibody MT110 eliminates primary human pancreatic cancer stem cells, *Clin. Cancer Res.* 18(2): 465-74 (2012).
Cole et al., Monoclonal Antibodies and Cancer Therapy, Alan R Liss Inc., New York: 77-96 (1985).
Cortiella et al., Influence of acellular natural lung matrix on murine embryonic stem cell differentiation and tissue formation, *Tissue Eng. Part. A*, 16: 2565-80 (2010).
Cote et al., Generation of human monoclonal antibodies reactive with cellular antigens, *Proc. Natl. Acad. Sci.* 80(7): 2026-30 (1983).
Crapo et al., An overview of tissue and whole organ decellularization processes, *Biomaterials*, 32(12): 3233-43 (2011).
Daghini et al., Assessment of renal hemodynamics and function in pigs with 64-section multidetector CT: comparison with electron-beam CT, *Radiology*, 243(2): 405-12 (2007).
Daley et al., Extracellular matrix dynamics in development and regenerative medicine, *J. Cell Sci.* 121(Pt 3):255-64 (2008).
Donati et al., Extracorporeal detoxification for hepatic failure using molecular adsorbent recirculating system: depurative efficiency and clinical results in a longterm follow-up, *Artif. Organs*, 38: 125-34 (2009).
Esmatjes et al., The utility of the C9peptide in the phenotyping of patient candidates for pancreas transplantation, *Clin. Transplant.* 21(3): 358-62 (2007).
Faulk et al., Role of the extracellular matrix in whole organ engineering, *J. Cell Physiol.* 229(8): 984-9 (2014).
Fournier et al., Bispecific antibodies and trispecific immunocytokines for targeting the immune system against cancer: preparing for the future, *BioDrugs*, 27(1): 35-53 (2013).
Gattazzo et al., Extracellular matrix: a dynamic microenvironment for stem cell niche, *Biochim. Biophys. Acta.* 1840(8): 2506-19 (2014).
Gilbert, Strategies for tissue and organ decellularization, *J. Cell Biochem.* 113(7): 2217-22 (2012).
Gray, Anatomy of the human body: 2i. The liver, (20th ed.): 1-54 (1918).
Groffen et al., Agrin is a major heparan sulfate proteoglycan in the human glomerular basement membrane, *J. Histochem. Cytochem.* 46(1): 19-27 (1998).
Hammel et al., Regression of liver fibrosis after biliary drainage in patients with chronic pancreatitis and stenosis of the common bile duct, *N. Engl. J. Med.* 344(6): 418-23 (2001).
Haskard et al., The production of human monoclonal autoantibodies from patients with rheumatoid arthritis by the EBV-hybridoma technique, *J. Immunol. Methods*, 74(2): 361-7 (1984).
Hata et al., Transplantation of engineered chimeric liver with autologous hepatocytes and xenobiotic scaffold, *Ann. Surg.* 257(3): 542-7 (2013).
Hoerstrup et al., Functional growth in tissue-engineered living, vascular grafts: follow-up at 100 weeks in a large animal model, *Circulation*, 114(1 Suppl): I159-66 (2006).
Huse et al., Generation of a large combinatorial library of the immunoglobulin repertoire in phage lambda, *Science*, 246(4935): 1275-81 (1989).
Hynes. The extracellular matrix: not just pretty fibrils, *Science*, 326(5957): 1216-9 (2009).
Iannotti et al., Porcine small intestine submucosa augmentation of surgical repair of chronic two-tendon rotator cuff tears. A randomized, controlled trial, *J. Bone Joint Surg. Am.* 88(6): 1238-44 (2006).
Jain et al., Engineering vascularized tissue, *Nat. Biotechnol.* 23(7): 821-3 (2005).
Janeway et al. (eds.), Immunobiology, Garland Publishing, New York, (5th ed.): (2001).
Johnson et al., Effector cell recruitment with novel Fv-based dual-affinity re-targeting protein leads to potent tumor cytolysis and in vivo B-cell depletion, *J. Mol. Biol.* 399(3): 436-49 (2010).
Jones et al., Replacing the complementarity-determining regions in a human antibody with those from a mouse, *Nature*, 321(6069): 522-5 (1986).
Kabat et al., Sequences of proteins of immunological interest, U.S. Department of Health and Human Services, (1983).
Kanasaki et al., Integrin beta1-mediated matrix assembly and signalling are critical for the normal development and function of the kidney glomerulus, *Dev. Biol.* 313: 584-93 (2008).
Ko et al., Enhanced re-endothelialization of acellular kidney scaffolds for whole organ engineering via antibody conjugation of vasculatures, *Technology*, 2: 243-53 (2014).
Ko et al., Targeting mesenchymal stem cells to activated endothelial cells, *Biomaterials*, 30(22): 3702-10 (2009).
Kohler et al., Continuous cultures of fused cells secreting antibody of predefined specificity, *Nature*, 256(5517): 495-7 (1975).
Kortt et al., Dimeric and trimeric antibodies: high avidity scFvs for cancer targeting, *Biomol. Eng.* 18(3): 95-108 (2001).
Kozbor et al., The production of monoclonal antibodies from human lymphocytes, *Immunol. Today*, 4(3): 72-9 (1983).
Lang et al., Three-dimensional culture of hepatocytes on porcine liver tissue-derived extracellular matrix, *Biomaterials*, 32(29): 7042-52 (2011).
Lawton et al., Early stenosis of medtronic mosaic porcine valves in the aortic position, *J. Thorac. Cardiovasc. Surg.* 137(6): 1556-7 (2009).
Lin et al., Spironolactone ameliorates podocytic adhesive capacity via restoring integrin alpha 3 expression in streptozotocin-induced diabetic rats, *J. Renin. Angiotensin. Aldosterone Syst.* 11(3): 149-57 (2010).

(56) References Cited

OTHER PUBLICATIONS

Macchiarini et al., Clinical transplantation of a tissue-engineered airway, *Lancet*, 372(9655): 2023-30 (2008).
Manelli et al., 3D analysis of SEM images of corrosion casting using adaptive stereo matching, *Microsc. Res. Tech.* 70(4): 350-4 (2007).
Marcellin et al., Regression of cirrhosis during treatment with tenofovir disoproxil fumarate for chronic hepatitis B: a 5-year open-label follow-up study, *Lancet*, 381(9865): 468-75 (2013).
Matas et al., OPTN/SRTR 2011 annual data deport: kidney, *Am. J. Transplant*, 13 (Suppl 1):11-46 (2013).
McAleese et al., RECRUIT-TandAbs: harnessing the immune system to kill cancer cells, Future Oncol. 8(6): 687-95 (2012).
Miner, The glomerular basement membrane, *Exp. Cell Res.* 318(9): 973-8 (2012).
Mirmalek-Sani et al., Porcine pancreas extracellular matrix as a platform for endocrine pancreas bioengineering, *Biomaterials*, 34(22): 5488-95 (2013).
Mitzner et al., Albumin dialysis MARS: knowledge from 10 years of clinical investigation, *ASAIO J.* 55(5): 498-502 (2009).
Moore et al., Application of dual affinity retargeting molecules to achieve optimal redirected T-cell killing of B-cell lymphoma, *Blood*, 117(17): 4542-51 (2011).
Moran et al., Whole-organ bioengineering: current tales of modern alchemy, *Transl. Res.* 163(4): 259-67 (2014).
Morrison et al., Chimeric human antibody molecules: mouse antigen-binding domains with human constant region domains, *Proc. Natl. Acad. Sci.* 81(21): 6851-5 (1984).
Nakayama et al., Decellularized rhesus monkey kidney as a three-dimensional scaffold for renal tissue engineering, *Tissue Eng. Part A*, 16(7): 2207-16 (2010).
Nakayama et al., Renal tissue engineering with decellularized rhesus monkey kidneys: age-related differences, *Tissue Eng. Part A*, 17(23-24): 2891-901 (2011).
Nakayama et al., Tissue specificity of decellularized rhesus monkey kidney and lung scaffolds, *PLoS One*, 8(5): e64134 (2013).
Navone et al., Isolation and expansion of human and mouse brain microvascular endothelial cells, *Nat. Protoc.* 8(9): 1680-93 (2013).
Neuberger et al., Recombinant antibodies possessing novel effector functions, *Nature*, 312(5995): 604-8 (1984).
Ng et al., Lineage restricted progenitors for the repopulation of decellularized heart, *Biomaterials*, 32(30): 7571-80 (2011).
Nichols et al., Production and utilization of acellular lung scaffolds in tissue engineering, *J. Cell. Biochem.* 113(7): 2185-92 (2012).
Orlandi et al., Cloning immunoglobulin variable domains for expression by the polymerase chain reaction, *Proc. Natl. Acad. Sci.* 86(10): 3833-7 (1989).
Orlando et al., Cell replacement strategies aiming at reconstitution of the beta cell compartment in type 1 diabetes, *Diabetes*, 63(5): 1433-44 (2014).
Orlando et al., Discarded human kidneys as a source of ECM scaffolds for kidney regeneration technologies, *Biomaterials*, 34(24): 5915-25 (2013).
Orlando et al., How regenerative medicine may contribute to the achievement of an immunosuppression-free state, *Transplantation*, 92(8): e36-8 (2011).
Orlando et al., Organ bioengineering and regeneration as the new Holy Grail of organ transplantation, *Ann. Surg.* 258(2): 221-32 (2013).
Orlando et al., Pancreas transplantation for type 2 diabetes mellitus, *Curr. Op. Org. Transpl.* 16(1): 110-5 (2011).
Orlando et al., Production and implantation of renal extracellular matrix scaffolds from porcine kidneys as a platform for renal bioengineering investigations, *Ann. Surg.* 256(2): 363-70 (2012).
Orlando et al., Regenerative medicine and organ transplantation: past, present and future, *Transplantation*, 91(12): 1310-7 (2011).
Orlando et al., Regenerative medicine as applied to general surgery, *Ann. Surg.* 255(5): 867-80 (2012).
Orlando et al., Regenerative medicine as applied to solid organ transplantation: current status and future development, *Transpl. Int.* 24(3): 223-32 (2011).
Orlando, Immunosuppression-free transplantation reconsidered from a regenerative medicine perspective, *Exp. Rev. Clin. Immun.* 8(2): 179-87 (2012).
Orlando, Transplantation as a subfield of regenerative medicine. An interview by Lauren Constable, *Exp. Rev. Clin. Immunol.* 7(2):137-41 (2011).
Ott et al., Perfusion-decellularized matrix: using nature's platform to engineer a bioartificial heart, Nat. Med. 14(2): 213-21 (2008).
Ott et al., Regeneration and orthotopic transplantation of a bioartificial lung, *Nat. Med.* 16(8): 927-33 (2010).
Owens et al., The genetic engineering of monoclonal antibodies, *J. Immunol. Meth.* 168(2): 149-65 (1994).
Pedersen et al., Comparison of surface accessible residues in human and murine immunoglobulin Fv domains. Implication for humanization of murine antibodies, *J. Mol. Biol.* 235(3): 959-73 (1994).
Peloso et al., Sisyphus, the Giffen's paradox and the holy grail: time for organ transplantation to transition toward a regenerative medicine-focused type of research, *Expert Rev. Clin. Immunol.* 9(10): 883-5 (2013).
Pereira-Sampaio et al., Cranial pole nephrectomy in the pig model: anatomic analysis of arterial injuries in tridimensional endocasts, *J. Endourol.* 26(6): 716-21 (2013).
Perera et al., Current status and recent advances of liver transplantation from donation after cardiac death, *World J. Gastrointest. Surg.* 3(11): 167-76 (2011).
Petersen et al., Tissue-engineered lungs for in vivo implantation, *Science*, 329(5991): 538-41 (2010).
Portner et al., T and NK cells of B cell NHL patients exert cytotoxicity against lymphoma cells following binding of bispecific tetravalent antibody CD19×CD3 or CD19×CD16, *Cancer Immunol. Immunother.* 61(10): 1869-75 (2012).
Pozzi et al., Beta1 integrin expression by podocytes is required to maintain glomerular structural integrity, *Dev. Biol.* 316(2): 288-301 (2008).
Rahimi et al., A role for cadherin-5 in regulation of vascular endothelial growth factor receptor 2 activity in endothelial cells, *Mol. Biol. Cell.* 10: 3401-7 (1999).
Reiter et al., Engineering interchain disulfide bonds into conserved framework regions of Fv fragments: improved biochemical characteristics of recombinant immunotoxins containing disulfide-stabilized Fv, *Protein Eng.* 7(5): 697-704 (1994).
Remuzzi et al., ACE inhibition reduces glomerulosclerosis and regenerates glomerular tissue in a model of progressive renal disease, *Kidney Int.* 69: 1124-30 (2006).
Remuzzi et al., Mechanisms of progression and regression of renal lesions of chronic nephropathies and diabetes, *J. Clin. Invest.* 116: 288-96 (2006).
Reusch et al., A novel tetravalent bispecific TandAb (CD30/CD16A) efficiently recruits NK cells for the lysis of CD30+ tumor cells, *MAbs.* 6(3): 728-39 (2014).
Riechmann et al., Reshaping human antibodies for therapy, *Nature*, 332(6162): 323-7 (1988).
Roder et al., The EBV-hybridoma technique, *Methods Enzymol.* 121: 140-67 (1986).
Ross et al., Embryonic stem cells proliferate and differentiate when seeded into kidney scaffolds, *J. Am. Soc. Nephrol.* 20(11): 2338-47 (2009).
Ross et al., Mouse stem cells seeded into decellularized rat kidney scaffolds endothelialize and remodel basement membranes, *Organogenesis*, 8(2): 49-55 (2012).
Ross et al., Regeneration and bioengineering of transplantable abdominal organs: current status and future challenges, *Expert Opin. Biol. Ther.* 13(1): 103-13 (2013).
Rossi et al., A new class of bispecific antibodies to redirect T cells for cancer immunotherapy, *MAbs*, 6(2): 381-91 (2014).
Salvatori et al., Extracellular matrix scaffold technology for bioartificial pancreas engineering: state of the art and future challenges, *J. Diabetes Sci. Technol.* 8(1): 159-69 (2014).

(56) References Cited

OTHER PUBLICATIONS

Salvatori et al., Semi-xenotransplantation: the regenerative medicine based-approach to immunosuppression-free transplantation and to meet the organ demand, *Xenotransplantation*, 22(1): 1-6 (2015).
Schenke-Layland et al., The use of three-dimensional nanostructures to instruct cells to produce extracellular matrix for regenerative medicine strategies, *Biomaterials*, 30: 4665-75 (2009).
Schlereth et al., Eradication of tumors from a human colon cancer cell line and from ovarian cancer metastases in immunodeficient mice by a single-chain Ep-CAM-/CD3-bispecific antibody construct, *Cancer Res.* 65(7): 2882-9 (2005).
Schlereth et al., Potent inhibition of local and disseminated tumor growth in immunocompetent mouse models by a bispecific antibody construct specific for Murine CD3, *Cancer Immunol. Immunother.* 55(7):785-96 (2006).
Shupe et al., Method for the decellularization of intact rat liver, *Organogenesis*, 6(2): 134-6 (2010).
Skardal et al., Tissue specific synthetic ECM hydrogels for 3-D in vitro maintenance of hepatocyte function, *Biomaterials*, 33(18): 4565-75 (2012).
Song et al., Regeneration and experimental orthotopic transplantation of a bioengineered kidney, *Nat. Med.* 19(5): 646-51 (2013).
Soto-Gutierrez et al., Perspectives on whole organ assembly: moving toward transplantation on demand, *J. Clin. Invest.* 122(11): 3817-23 (2012).
Spenlé et al., Laminin α5 guides tissue patterning and organogenesis. *Cell Adh. Migr.* 7(1): 90-100 (2012).
Sullivan et al., Decellularization methods of porcine kidneys for whole organ engineering using a high-throughput system, *Biomaterials*, 33(31): 7756-64 (2012).
Takeda et al., Construction of chimaeric processed immunoglobulin genes containing mouse variable and human constant region sequences, *Nature*, 314(6010): 452-4 (1985).
Tapias et al., Decellularized scaffolds as a platform for bioengineered organs, *Curr. Opin. Organ Transplant.* 19(2): 145-52 (2014).
Todorovska et al., Design and application of diabodies, triabodies and tetrabodies for cancer targeting, *J. Immunol. Methods*, 248(1-2): 47-66 (2001).
Totonelli et al., Production and characterization of a rat decellularized small bowel scaffold that preserves villus-crypt architecture, *Biomaterials*, 33(12): 3401-10 (2012).
Uygun et al., Organ reengineering through development of a transplantable recellularized liver graft using decellularized liver matrix, *Nat. Med.* 16(7): 814-20 (2010).
Verhoeyen et al., Reshaping human antibodies: grafting an antilysozyme activity, *Science*, 239(4847): 1534-6 (1988).
Vodicka et al., The miniature pig as an animal model in biomedical research, *Ann. N. Y. Acad. Sci.* 1049: 161-71 (2005).
Wang et al., Lineage restriction of human hepatic stem cells to mature fates is made efficient by tissue-specific biomatrix scaffolds, *Hepatology*, 53(1): 293-305 (2011).
Wang et al., Method for perfusion decellularization of porcine whole liver and kidney for use as a scaffold for clinical-scale bioengineering engrafts, *Xenotransplantation*, 22(1): 48-61 (2015).
Wilkin, The accelerator hypothesis: a review of the evidence for insulin resistance as the basis for type I as well as type II diabetes, *Int. J. Obes.* (*Lond*), 33(7): 716-26 (2009).
Winter et al., Man-made antibodies, *Nature*, 349(6307): 293-9 (1991).
Winterdahl et al., Hepatic blood perfusion estimated by dynamic contrast-enhanced computed tomography in pigs: limitations of the slope method, *Invest Radiol.* 47(10): 588-95 (2012).
Yagi et al., Whole-organ re-engineering: a regenerative medicine approach to digestive organ replacement, *Surg. Today*, 43(6): 587-94 (2013).
Zhang et al., Identification of proliferating human hepatic cells from human induced pluripotent stem cells, *Transplant Proc.* 46(4): 1201-4 (2014).
Zhou et al., Decellularized liver matrix as a carrier for the transplantation of human fetal and primary hepatocytes in mice, *Liver Transpl.* 17(4): 418-27 (2011).

\* cited by examiner

H&E Staining

ORGAN/TISSUE DECELLULARIZATION, FRAMEWORK MAINTENANCE AND RECELLULARIZATION

FIELD

The disclosure relates generally to the decellularization of diseased or injured organs or tissues and to the recellularization thereof.

BACKGROUND

In the United States, more than 2,600 kidneys are discarded annually, from the total number of kidneys procured for transplant. In organ bioengineering and regeneration, seeding of cells on supporting scaffolding material offers a potential route to clinical application [1-24]. Discarded organs represent a catastrophic and unrelenting figure at a time of dramatic organ shortage and urgent need for new, potentially inexhaustible sources of transplantable organs.

Cell-scaffold technology has allowed researchers to manufacture relatively simple structures such as vessels, bladders, segments of upper airways and urethras from the patients' own cells, which were eventually implanted in patients with good short- and mid-term results. If we exclude the case of bioengineered vessels, the new structures were implanted without being reconnected to the vascular system, on the assumption that tissues of the bioengineered structures would initially receive oxygen and nutrients by diffusion from adjacent vascularised tissues of the host until neoangiogenesis occurred. While this strategy (i.e., not reconnecting the new structure to the recipient's vasculature) may be acceptable for thin structures such as the ones mentioned above, it is inadequate for more complex, "thicker" organs like the kidney, which requires reconnection to the patient's vascular system to maintain cell viability and the core of the organ, as well as, to exert function.

Organ transplantation is one of the greatest achievements in the history of modern medicine. In view of the excellent results attained to date, the demand for transplantable organs is escalating, whereas the supply has reached a plateau. Consequently, waiting times and patients' mortality while on the waiting list are increasing dramatically (FIG. 1A) and so the identification of new, potentially inexhaustible sources of organs has become an urgent need.

SUMMARY

The disclosure provides materials and methods that diminish the aforementioned need by a new source of tissues and organs claimed from tissues and organs previously discarded. The methods provide an approach to the decellularization of tissues and organs that are diseased or otherwise deemed unusable in transplant scenarios. Following decellularization, disclosed herein are methods for maintaining the acellular tissue or organ scaffold or framework composed largely of extracellular matrix with intact vasculature. Also provided are methods for recellularizing the tissue or organ scaffold ex vivo or in vivo, thereby regenerating a healthy tissue or organ.

In one aspect, the disclosure provides a method of regenerating a tissue or organ comprising inserting an acellular tissue or organ scaffold into a subject in need thereof, establishing at least two vascular connections of the scaffold vasculature and the subject vasculature, and incubating the acellular scaffold until an intact tissue or organ is produced. It is expected that this method will prove advantageous for tissues and organs too thick to obtain sufficient in vivo oxygen and nutrients via diffusion to be viable and thrive. In particular, the disclosure provides a method of regenerating a tissue or organ for a subject in need comprising: (a) providing an acellular tissue or organ scaffold; (b) contacting the tissue or organ scaffold with a cell characteristic of the tissue or organ; (c) incubating the scaffold and cell ex vivo under static conditions; (d) implanting the incubated scaffold and cell into the subject and establishing at least two vascular connections of the scaffold vasculature and the subject vasculature; and (e) incubating the acellular scaffold until an intact tissue or organ is produced. In some embodiments the cell is obtained from the subject. In some embodiments, the scaffold is contacted with at least $5\times10^7$ cells. An example of a cell for use in the method is a vascular endothelial cell.

A variation of the method further comprises incubating ex vivo the scaffold and cell under ramping perfusion conditions, e.g., wherein the perfusion comprises delivery of at least $1\times10^8$ cells at a varying rate spanning 2 ml/minute to 20 ml/minute. Some embodiments of any of the above methods further comprise attachment to the scaffold of an antibody product specifically binding to the cell, such as an antibody product comprises an antigen binding site for CD31. By "antibody product" is meant a complete antibody or any fragment or variant form thereof that retains at least the six complementarity determining regions specifying the binding specificity of the antibody product. In some embodiments, the method further comprises attachment of an anti-thrombotic composition to the scaffold, such as attachment of heparin to the scaffold. In various embodiments, the organ is a kidney, pancreas, liver, gall bladder, stomach, small intestine and large intestine; exemplary organs include a kidney, a pancreas or a liver.

In another aspect, the disclosure provides a method of decellularizing a tissue or organ comprising: (a) perfusing an ex vivo tissue or organ with at least 50 volumes of a detergent; and (b) rinsing the ex vivo tissue or organ with at least 50 volumes of a neutral buffer. The detergent may be either ionic or non-ionic. In some embodiments, the organ is selected from the group consisting of kidney, pancreas, liver, gall bladder, stomach, small intestine and large intestine, for example kidney, pancreas or liver. For kidney decellularization and the decellularization of other hardy organs, an ionic detergent, e.g., sodium dodecyl sulfate, is used. For less hardy organs such as the pancreas, a non-ionic detergent, e.g., 2-[4-(2,4,4-trimethylpentan-2-yl)phenoxylethanol (Triton X-100), is used. Some embodiments comprise a method wherein the perfusing and rinsing are performed using at least two fluid inlets and at least one fluid outlet. The methods may be performed using a variety of fluid flow rates, as would be understood in the art. In some embodiments of the method, the flow rate of the two fluid inlets is about equal. In some embodiment, the flow rate of the fluid outlet is at least 5 ml per minute.

The method described above may further comprise an initial step of delivering distilled water to the organ or tissue at a rate of about 12 ml per minute for at least 10 hours. Some applications of the method further comprise delivering at least one liter of 0.0025 w/w % DNase solution to the detergent-treated tissue or organ prior to rinsing the tissue or organ.

The method described above contemplates embodiments wherein the ionic detergent is an anionic detergent. In some embodiments, the anionic detergent is an organosulfate detergent, e.g., sodium dodecyl sulfate. For example, the disclosure contemplates embodiments wherein the sodium dodecyl sulfate is 0.5% sodium dodecyl sulfate. As noted above, other embodiments use a non-ionic detergent such as 2-[14-(2,4,4-trimethylpentan-2-yl)phenoxy]ethanol (Triton X-100).

Some embodiments comprise a method wherein the tissue or organ is perfused with at least 30 liters of ionic detergent. Some embodiments comprise a method wherein the perfused tissue or organ is rinsed with at least 40 liters of neutral buffer. Also comprehended are methods wherein the perfusing step is performed for at least 10 hours.

In some embodiments, the neutral buffer is phosphate-buffered saline. Further, some embodiments are contemplated wherein the rinsing step is performed for at least 40 hours. Some embodiments comprise a method wherein the neutral buffer contains 10 U/ml heparin.

Further comprehended are embodiments wherein the method further comprises exposing the tissue or organ to a bactericidal agent. Any bactericidal, microbicidal, bacteriostatic, or anti-microbic agent known in the art to be compatible with eukaryotic cells, tissues and organs, such as human cells, organs and tissues, is contemplated by the disclosure, including but not limited to povidone-iodine (betadine).

Other features and advantages of the disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWING

FIGS. 40A-D shows kidney macroscopic frontal view during whole-kidney detergent-based de-cellularization protocol. Representative time lapse of kidney decellularization at T0 (A) and after 16, 32, and 48 hours (T1, T2 and T3) (B, C and D, respectively). Peristaltic perfusion through the renal artery and the ureter (12.5 ml/minute), with the renal vein used as vascular outlet, permits homogeneous and complete cellular compartment removal with a slow progressive change of the color of the organ. FIGS. 40E-H shows a human renal vascular corrosion cast obtained by injection of a specific resin via the renal artery (red dye), the renal vein (blue dye) and the ureter (yellow dye). Macroscopic anterior view of the endocast (E) shows the uniform distribution of the resin, obtained by a gentle continuous injection, inside the native kidney vascular tree from the renal hilum to last vascular branching. Panel F shows the three-dimensional endocast of final renal vascular branching system; the resin filled the finest branches of the vascular network (arterial and venous). Panel G shows the complete preservation of the macrostructures of the organ (arterial, venous and ureteral collecting system). The sample in question possesses a double-ureter and pelvicaliceal system that preserves its entire structure at all detectable hierarchical levels. Even without cells present, the casting resin filled the whole scaffold in its upper and lower pole, producing a final high-fidelity tridimensional reconstruction. Magnification of the lower pole of the endocast (H) shows preservation of the final vascular divisions of the scaffold as observed from the native organ.

FIGS. 41A and 41C show representative SEM images of a single extracted native glomerulus derived from the cortical portion of the vascular corrosion endocast of a native kidney, while FIGS. 41B and 41D show representative SEM images of a single extracted glomerulus derived from the cortical portion of the vascular corrosion endocast of an acellular kidney (scalebar: 100 µm). In both series major glomerular components (afferent artery and branched capillaries) are clearly visible. Background from the original snapshot (A and B) was removed to enhance and highlight effective glomerular morphological shape and to more accurately extrapolate its morphometric measurements. Diameter was measured twice, sagittally and transversally, (C and D) and then the average was calculated (green lines and circle). Afferent arteriolar width was acquired from three different transversal points (red lines) (C and D) and the final average assessed. Finally, six different transversal measurements were obtained (yellow lines) from singular capillaries in several areas of the glomerulus (C and D).

DETAILED DESCRIPTION

Figure 1:
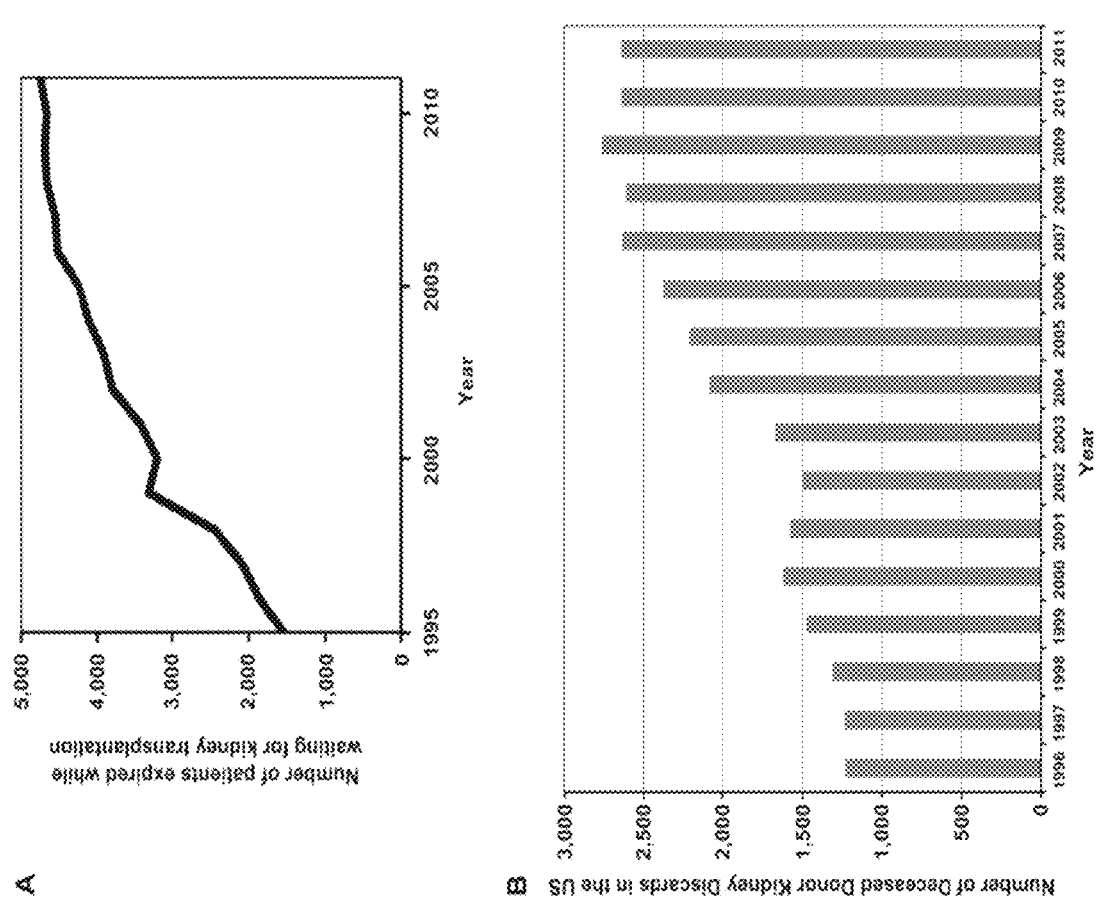
FIG. 1. Statistical data on kidney transplantation. A) United Network for Organ Sharing data on the number of patients who deceased while waiting for kidney transplantation. This number has dramatically increased in the last decade due to longer waiting times determined by the fact that the constantly growing number of patients registered in the waiting list is not being balanced by an adequate offer of transplantable kidneys. B) United Network for Organ Sharing data on human kidneys discarded from transplantation. Basically, one fifth of the procured kidneys are discarded as not suitable for transplantation for multiple reasons.

The disclosure provides materials and methods for decellularizing tissues and organs ex vivo, producing organ and tissue scaffolds or frameworks composed of extracellular matrix containing intact vasculature suitable for recellularization. Thus, the disclosure comprehends materials and methods for the decellularization of tissues or organs, materials and methods for maintenance of the tissue or organ scaffold, and materials and methods for the recellularization of such tissue or organ scaffolds. The technology provides an opportunity to eliminate the cost, suffering, loss in quality of life and loss of life itself associated with the ever-increasing disparity between patients in need of new tissues or organs and the supply thereof.

A pool of legally proper organs discarded for medical reasons may be used as a platform for renal bioengineering and regeneration research. The decellularization of porcine kidneys yields renal extracellular matrix (ECM) scaffolds that maintain their basic components, support cell growth and welfare in vitro and in vivo, and show an intact vasculature that, when such scaffolds are implanted in vivo, is able to sustain physiological blood pressure. Disclosed herein is a study expanding the strategy to discarded human kidneys in order to obtain human renal ECM scaffolds. The results show that the sodium dodecyl sulfate-based decellularization protocol completely cleared the cellular compartment in these kidneys, while the innate ECM framework retained its architecture and biochemical properties. Samples of human renal ECM scaffolds stimulated angiogenesis in a chick chorioallantoic membrane assay. The innate vascular network in the human renal ECM scaffolds retained its compliance. Collectively, these results indicate that discarded human kidneys are a suitable source of renal scaffolds and their use for tissue engineering applications may be more clinically applicable than kidneys derived from animals.

In attempts to bioengineer renal organ(oid)s for human transplant purposes, whole, intact scaffolds produced from the extracellular matrix (ECM) of animal or human kidneys offer some promise. An advantage of using natural scaffolds from innate organs lies in the fact that such biomaterials are intrinsically functional when used as tissue engineering scaffolds, have their basic biochemistry (proteins and polysaccharides) and architecture preserved, retain an intact and patent vasculature, and are able to drive differentiation of progenitor cells into organ-specific phenotypes.

After successful investigations in rodents [7-9, 13-17], the results were transferred to develop a more clinically relevant porcine model [25] because the evolutionary gap between humans and animal models is reduced with a pig model, although the use of non-human animal models has often prevented direct applicability of the knowledge to applications in humans [26]. As noted herein, the United States alone discards more than 2,600 kidneys annually from the total number of kidneys procured from deceased donors. Disclosed herein are studies assessing the suitability of human kidneys discarded from transplantation for use in renal bioengineering and organ(oid) regeneration. The main reasons for discard are severe anatomical anomalies such as glomerulosclerosis, tubular atrophy, interstitial fibrosis, inflammation, cortical necrosis, and vascular changes, however other causes including prolonged cold ischemia, excessive warm ischemia and poor renal function may intervene [27]. This number of organs accounts for nearly 20% of the whole kidney pool procured for transplant purposes, compared with about 12% in the late 1990s, and represent a dramatic figure, at a time of severe organ shortage and urgent need for the identification of new, valuable sources of organs. While the United Network for Organ Sharing is currently devising strategies to minimize the kidney discard rate, the technology disclosed herein salvages those discarded kidneys to produce ECM scaffolds for renal bioengineering and regeneration purposes.

The findings disclosed herein show that discarded human kidneys can be successfully decellularized to produce acellular renal ECM scaffolds. The acellular renal ECM scaffolds maintain their innate molecular and spatial framework, and are theoretically non-immunogenic because of the removal of antigens that are responsible for the activation of the immune rejection response. Thus, these renal scaffolds may represent an ideal platform for investigations aimed at the manufacture of kidneys for transplant purposes. Importantly, these scaffolds derive from diseased organs that were deemed unsuitable for clinical transplantation for a variety of reasons, mainly severe biopsy-proven damage. In fact, the most frequent lesion we have noticed in this study was above 20% glomerulosclerosis, which is often associated with moderate to severe vascular changes, interstitial fibrosis and tubular atrophy.

Studies in the porcine model have shown that the cellular compartment of the porcine kidneys can be completely cleared with SDS-based solutions to ultimately generate acellular ECM scaffolds. These scaffolds retain their complex three-dimensional architecture and basic molecular components. Their innate vascular tree remains intact at all hierarchical levels, including the tuft vessels and intact nephron framework, which can be easily identified using histology and electronic microscopy. The data also establish that these scaffolds can be successfully implanted in porcine recipients, using sequential anastomosis of the renal vein and artery to the vena cava and abdominal aorta, respectively, and that the scaffold's vasculature sustains well physiological blood pressure.

The protocol applied in the studies disclosed herein for discarded human kidneys differs from the one used for pigs in that we perfuse detergents not only through the artery but also through the ureter retrograde into the collecting system. We opted for this approach following initial unsuccessful attempts, while using only arterial perfusion, in which we observed that the severe tissue damage appeared to impair the decellularization process. It should be emphasized that when we performed the visualization of the vascular network by injecting contrast media within the renal artery, contrast cleared through the renal vein but no contrast leaked from the ureter. This indicates that the urinary tract compartment—which eventually drains into the ureter—is sealed, i.e., totally separated, from the vascular network; the reason for which we elected to add retrograde ureteral rinsing and perfusion to make sure that the detergent solution was delivered into all renal compartments to allow successful decellularization.

The successful preparation of acellular human renal ECM scaffolds is emphasized by 1) maintenance of native renal architecture both and at the macro and micro levels, including the vascular and nephron components, 2) removal of important cell-associated immunogenic markers and 3) preservation of natural renal ECM proteins that have an essential role in tissue development and regeneration. In addition, the capability of the scaffolds to induce neoangiogenesis may be interpreted as evidence of ex vivo—or, better, in ovo—regenerative capacity. Furthermore, for transplantation applications, our findings indicate that: (a) the preserved vasculature of acellular human renal ECM scaffolds is patent and resilient, as demonstrated by the fact that the vascular tree maintains the capability to modulate pressure following an increase of the inflow; (b) vessel resilience is determined in large part by the framework of the vasculature rather than its cellular compartment; (c) baseline pressure values are inferior to normal kidneys possibly due to the lack of muscular layer within the vessel wall and/or the baseline diseased status of the vascular tree; d) the angiogenic capability of the ECM scaffold indicates that it can further support the vascular endothelium of the regenerated vascular network and thus improve the microvasculature perfusion.

The results disclosed herein show that the sodium dodecyl sulfate-based decellularization protocol completely cleared the cellular compartment in these kidneys, while the innate ECM framework retained its architecture and biochemical properties. Samples of human renal ECM scaffolds stimulated angiogenesis in a chick chorioallantoic membrane assay. Importantly, the innate vascular network in the human renal ECM scaffolds retained its compliance. Collectively, these results indicate that discarded human kidneys are a suitable source of renal scaffolds and their use for tissue engineering applications is expected to be more clinically applicable than kidneys derived from animals.

The strategy of using discarded organs introduces a new type of biomaterial, represented by natural scaffolds obtained from the manipulation of organs with pre-existing damage. It is expected that human renal ECM scaffolds from discarded organs will maintain the ability to provide cell attachments in view of the successful seeding of cells that should be followed by appropriate attachment, proliferation and function. As one of the cell's functions is ECM remodeling by continuous degradation followed by synthesis and deposition of new ECM, it is expected that the baseline fibrosis will be eventually reverted, thereby paving the way for successful regeneration of normal kidney tissue.

Facilitating the use of natural scaffolds to provide functional tissues and organs through recellularization is the association of cell-binding antibody products, e.g., an anti-CD31 antibody product, with the scaffolds, improving the ability of scaffolds to recellularize. Thus, disclosed herein are antibody products derived from an antibody that specifically binds to an endothelial cell or in induced pluripotent stem cell. An exemplary antibody product comprises each of the six complementarity determining regions of the above-described antibody, in addition to further sequences which provide a framework to support a three-dimensional conformation that retains the binding property of the antibody from which the antibody product is derived. In exemplary embodiments, the antibody product comprises one or both of the light chain variable region and/or the heavy chain variable region of an antibody binding to an endothelial cell or an iPS cell. When present, the light and heavy chain variable regions may be joined via a linker. Suitable linkers are known in the art and include, e.g., a linker comprising a short amino acid sequence of about 5 to about 25 amino acids, e.g., about 10 to about 20 amino acids.

In exemplary embodiments, the antibody product provided herein further comprises additional amino acid sequences. The binding agent may further comprise a constant region of a heavy chain and/or a constant region of a light chain. Sequences for heavy and light chain constant regions are publically available. For example, the National Center of Biotechnology Information (NCBI) nucleotide database provides a sequence of the constant region of the IgG1 kappa light chain. See GenBank Accession No. DQ381549.1, incorporated herein by reference. Also, for example, the NCBI nucleotide database provides a sequence of the constant region of the *Mus musculus* IgG1. See GenBank Accession No. DQ381544.1.

The antibody product may be derived from an antibody of any type of immunoglobulin that is known in the art. For instance, the antibody can be of any isotype, e.g., IgA, IgD, IgE, IgG, IgM. The antibody can be monoclonal or polyclonal. The antibody can be a naturally occurring antibody, i.e., an antibody isolated and/or purified from a mammal, e.g., mouse, rabbit, goat, horse, chicken, hamster, human, and the like. In this regard, the antibody may be considered to be a mammalian antibody, e.g., a mouse antibody, rabbit antibody, goat antibody, horse antibody, chicken antibody, hamster antibody, human antibody, and the like. The term "isolated" as used herein means having been removed from its natural environment. The term "purified," as used herein relates to the isolation of a molecule or compound in a form that is substantially free of contaminants normally associated with the molecule or compound in a native or natural environment and means having been increased in purity as a result of being separated from other components of the original composition. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%. In exemplary aspects, the antibody comprises a constant region of an IgG, such as the constant region of an $IgG_1$. The antibody may comprise the constant region of an IgG kappa light chain. In some embodiments, the antibody comprises a constant region of a *Mus musculus* $IgG_1$.

The antibody products of the disclosure can have any level of affinity or avidity for an endothelial cell or an iPS cell. In certain embodiments in which the antibody product comprises two or more distinct antigen binding regions or fragments, the antibody product is considered bispecific, trispecific, or multi-specific, or bivalent, trivalent, or multivalent, depending on the number of distinct epitopes that are recognized and bound by the antibody product. The antibody product in exemplary aspects is considered to be a blocking antibody or neutralizing antibody.

In exemplary embodiments, the antibody product is a genetically engineered antibody, e.g., a single chain antibody, a humanized antibody, a chimeric antibody, a CDR-grafted antibody, an antibody that includes portions of CDR sequences specific for a cell-surface marker of an endothelial cell or an iPS cell, a humaneered or humanized antibody, a bispecific antibody, a trispecific antibody, and the like, as defined in greater detail herein. Genetic engineering techniques also provide the ability to make fully human antibodies in a non-human.

In some aspects, the antibody product is a chimeric antibody. The term "chimeric antibody" is used herein to refer to an antibody containing constant domains from one species and the variable domains from a second, or more generally, containing stretches of amino acid sequence from at least two species.

In some aspects, the antibody is a humanized antibody. The term "humanized" when used in relation to antibodies is used to refer to antibodies having at least CDR regions from a nonhuman source that are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence, as would be known in the art.

Use of the terms "chimeric or humanized" herein is not meant to be mutually exclusive; rather, is meant to encompass chimeric antibody products, humanized antibody products, and chimeric antibody products that have been further humanized. Except where context otherwise indicates, statements about (properties of, uses of, testing, and so on) chimeric antibody products apply to humanized antibody products, and statements about humanized antibody products pertain also to chimeric antibody products.

In some aspects of the disclosure, the antibody product is an antigen binding fragment of an antibody that specifically binds to an endothelial cell or iPS cell in accordance with the disclosure. The antigen binding fragment (also referred to herein as "antigen binding portion") may be an antigen binding fragment of any of the antibodies described herein. The antigen binding fragment can be any part of an antibody that has at least one antigen binding site including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like. Antibody fragments of the disclosure, however, are not limited to these exemplary types of antibody fragments.

In exemplary aspects, the antibody product comprises a leader sequence. In exemplary aspects, the antigen binding fragment comprises an Ig kappa leader sequence. Suitable leader sequences are known in the art.

In exemplary aspects, an antibody product of the disclosure comprises one more tag sequences. Tag sequences may assist in the production and characterization of the manufactured antigen binding fragment. In exemplary aspects, the antigen binding fragment comprises one or more tag sequences C-terminal to the binding domains of the antibody product. Suitable tag sequences are known in the art and include, but are not limited to, Myc tags, His tags, and the like.

In exemplary aspects, an antibody product of the disclosures comprises, from the N- to the C-terminus, a leader sequence, a heavy chain variable region, a linker sequence, a light chain variable region, a Myc tag, and a His tag.

In exemplary aspects, the antibody product is a domain antibody. A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth the weight of a full antibody. Domain antibodies may be derived from full antibodies. The antibody products in some embodiments are monomeric or polymeric, bispecific or trispecific, and bivalent or trivalent.

Antibody products that contain the antigen binding, or idiotope, of an antibody molecule share a common idiotype and are contemplated by the disclosure. Such antibody products may be generated by techniques known in the art and include, but are not limited to, the F(ab')$_2$ fragment which may be produced by pepsin digestion of an antibody; the Fab' fragments which may be generated by reducing the disulfide bridges of a F(ab')$_2$ antibody, and the two Fab' fragments which may be generated by treating an antibody with papain and a reducing agent.

In exemplary aspects, the antibody product provided herein is a single-chain variable region fragment (scFv) antibody fragment. An scFv may consist of a truncated Fab fragment comprising the variable (V) domain of an antibody heavy chain linked to a V domain of an antibody light chain via a synthetic peptide, and it can be generated using routine recombinant DNA technology techniques (see, e.g., Janeway et al., *Immunobiology*, 2$^{nd}$ Edition, Garland Publishing, New York, (1996)). Similarly, disulfide-stabilized variable region fragments (dsFv) can be prepared by recombinant DNA technology (see, e.g., Reiter et al., Protein Engineering, 7, 697-704 (1994)).

Recombinant antibody products, e.g., scFvs of the disclosure, can also be engineered to assemble into stable multimeric oligomers of high binding avidity and specificity to different target antigens on endothelial and iPS cells. Such diabodies (dimers), triabodies (trimers) or tetrabodies (tetramers) are well known in the art. See e.g., Kortt et al., *Biomol Eng.* 2001 18:95-108, (2001) and Todorovska et al., *J Immunol Methods.* 248:47-66, (2001).

In exemplary embodiments, the antibody product is a bispecific antibody (bscAb). Bispecific antibodies are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNAs obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entireties.

In exemplary embodiments, the antibody product is a bispecific T-cell engaging antibody (BiTE) containing two scFvs produced as a single polypeptide chain. Methods of making and using BiTE antibodies are described in the art. See, e.g., Cioffi et al., *Clin Cancer Res* 18: 465, Brischwein et al., *Mol Immunol* 43:1129-43 (2006); Amann M et al., *Cancer Res* 68:143-51 (2008); Schlereth et al., *Cancer Res* 65: 2882-2889 (2005); and Schlereth et al., *Cancer Immunol Immunother* 55:785-796 (2006).

The antibody product may be a dual affinity re-targeting antibody (DART). DARTs are produced as separate polypeptides joined by a stabilizing interchain disulfide bond. In exemplary embodiments, the antibody product is a DART comprising an scFv. Methods of making and using DART antibodies are described in the art. See, e.g., Rossi et al., *MAbs* 6: 381-91 (2014); Fournier and Schirrmacher, BioDrugs 27:35-53 (2013); Johnson et al., *J Mol Biol* 399:436-449 (2010); Brien et al., *J Virol* 87: 7747-7753 (2013); and Moore et al., *Blood* 117:4542 (2011).

In exemplary embodiments, the antibody product is a tetravalent tandem diabody (TandAbs) in which an antibody fragment is produced as a non-covalent homodimer folded in a head-to-tail arrangement. TandAbs are known in the art. See, e.g., McAleese et al., *Future Oncol* 8: 687-695 (2012); Portner et al., *Cancer Immunol Immunother* 61:1869-1875 (2012); and Reusch et al., *MAbs* 6:728 (2014).

The BiTE, DART, or TandAbs of the disclosure comprise the CDRs of an antibody that binds an endothelial or iPS cell.

Suitable methods of making antibodies and/or antibody product are known in the art. For instance, standard hybridoma methods are described in, e.g., Harlow and Lane (eds.), Antibodies: A Laboratory Manual, CSH Press (1988), and C A. Janeway et al. (eds.), Immunobiology, $5^{th}$ Ed., Garland Publishing, New York, N.Y. (2001)).

Monoclonal antibodies as source material for the antibody products of the disclosure may be prepared using any technique that provides for the production of antibody molecules by continuous cell lines in culture. These include, but are not limited to, the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

Briefly, a polyclonal antibody is prepared by immunizing an animal with an immunogen comprising an antigenic polypeptide and collecting antisera from that immunized animal. A wide range of animal species can be used for the production of antisera. In some aspects, an animal used for production of anti-antisera is a non-human animal including rabbits, mice, rats, hamsters, goat, sheep, pigs or horses. Because of the relatively large blood volume of rabbits, a rabbit, in some exemplary aspects, is a preferred choice for production of polyclonal antibodies. In an exemplary method for generating a polyclonal antisera immunoreactive with the chosen marker of an endothelial and/or iPS cell, 50 µg of antigenic marker is emulsified in Freund's Complete Adjuvant for immunization of rabbits. At intervals of, for example, 21 days, 50 µg of epitope are emulsified in Freund's Incomplete Adjuvant for boosts. Polyclonal antisera may be obtained, after allowing time for antibody generation, simply by bleeding the animal and preparing serum samples from the whole blood.

Briefly, in exemplary embodiments, to generate monoclonal antibodies, a mouse is injected periodically with the antigenic marker against which the antibody is to be raised (e.g., 10-20 µg of the marker emulsified in Freund's Complete Adjuvant). The mouse is given a final pre-fusion boost of the antigenic marker, and four days later the mouse is sacrificed and its spleen removed. The spleen is placed in 10 ml serum-free RPMI 1640, and a single-cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11% fetal bovine serum (FBS) (Hyclone Laboratories, Inc., Logan, Utah) for three days prior to fusion, are centrifuged at 200 g for 5 minutes, and the pellet is washed twice.

Spleen cells ($1\times10^8$) are combined with $2.0\times10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5\times10^6$ splenocytes/ml and plated into 10 Corning flat-bottom 96-well tissue culture plates (Corning, Corning N.Y.).

On days 2, 4, and 6, after the fusion, 100 µl of medium is removed from the wells of the fusion plates and replaced with fresh medium. On day 8, the fusion is screened by ELISA, testing for the presence of mouse IgG binding to the marker.

Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media that support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/15XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions. It should be noted that the hybridomas and cell lines produced by such techniques for producing the monoclonal antibodies are contemplated to be compositions of the disclosure.

Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Alternatively, other methods, such as EBV-hybridoma methods (Haskard and Archer, J. Immunol. Methods, 74(2), 361-67 (1984),and Roder et al.,5 Methods Enzymol., 121, 140-67 (1986)), and bacteriophage vector expression systems (see, e.g., Huse et al., Science, 246, 1275-81 (1989)) that are known in the art may be used. Further, methods of producing antibodies in non-human animals are described in, e.g., U.S. Pat. Nos. 5,545,806, 5,569,825, and 5,714,352, and U.S. Patent Application Publication No. 2002/0197266 A1.

Antibodies may also be produced by inducing in vivo production in the lymphocyte population or by screening recombinant immunoglobulin libraries or panels of highly specific binding reagents as disclosed in Orlandi et al. (Proc. Natl. Acad. Sci. 86: 3833-3837; 1989), and Winter and Milstein (Nature 349: 293-299, 1991).

Furthermore, phage display can be used to generate an antibody of the disclosure. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, $3^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150). Related methods also are described in U.S. Pat. Nos. 5,403,484; 5,571,698; 5,837, 500; and 5,702,892. The techniques described in U.S. Pat. Nos. 5,780,279; 5,821,047; 5,824,520; 5,855,885; 5,858, 657; 5,871,907; 5,969,108; 6,057,098; and 6,225,447, are also contemplated as useful in preparing antibodies according to the disclosure.

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539; 5,585,089; and 5,693,761; European Patent No. 0239400 B1; and United Kingdom Patent No. 2188638. Humanized antibodies can also be generated using the antibody resurfacing technology described in U.S. Pat. No. 5,639,641 and Pedersen et al., J. Mol. Biol., 235:959-973 (1994).

Techniques developed for the production of "chimeric antibodies," the splicing of mouse antibody genes to human antibody genes to obtain a molecule with appropriate antigen specificity and biological activity, can be used (Morrison et al., Proc. Natl. Acad. Sci. 81: 6851-6855, 1984; Neuberger et al., Nature 312: 604-608, 1984; and Takeda et al., Nature 314: 452-454; 1985). Alternatively, techniques described for the production of single-chain antibodies (U.S. Pat. No. 4,946,778) can be adapted to produce endothelial or iPS cell-specific single chain antibodies.

A preferred chimeric or humanized antibody has a human constant region, while the variable region, or at least a CDR, of the antibody is derived from a non-human species. Methods for humanizing non-human antibodies are well known in the art. (see U.S. Pat. Nos. 5,585,089, and 5,693, 762). Generally, a humanized antibody has one or more amino acid residues introduced into a CDR region and/or into its framework region from a source which is non-human. Humanization can be performed, for example, using methods described in Jones et al. (*Nature* 321: 522-525, 1986), Riechmann et al., (*Nature*, 332: 323-327, 1988) and Verhoeyen et al. (*Science* 239:1534-1536, 1988), by substituting at least a portion of a rodent complementarity-determining region (CDR) for the corresponding region of a human antibody. Numerous techniques for preparing engineered antibodies are described, e.g., in Owens and Young, J. Immunol. Meth., 168:149-165 (1994). Further changes can then be introduced into the antibody framework to modulate affinity or immunogenicity.

Consistent with the foregoing description, compositions comprising CDRs may be generated using, at least in part, techniques known in the art to isolate CDRs. Complementarity-determining regions are characterized by six polypeptide loops, three loops for each of the heavy or light chain variable regions. The amino acid position in a CDR is defined by Kabat et al., "Sequences of Proteins of Immunological Interest," U.S. Department of Health and Human Services, (1983), which is incorporated herein by reference. For example, hypervariable regions of human antibodies are roughly defined to be found at residues 28 to 35, from 49-59 and from residues 92-103 of the heavy and light chain variable regions [Janeway et al., supra]. The murine CDRs also are found at approximately these positions in the heavy and light chain variable regions of antibodies. It is understood in the art that CDR regions may be found within several amino acids of the approximated amino acid positions set forth above. An immunoglobulin variable region also consists of four "framework" regions surrounding the CDRs (FR1-4). The sequences of the framework regions of different light or heavy chains are highly conserved within a species, and are also conserved between human and murine sequences.

Compositions comprising one, two, and/or three CDRs of a heavy chain variable region or a light chain variable region of a monoclonal antibody are generated. Polypeptide compositions comprising one, two, three, four, five and/or six complementarity-determining regions of an antibody are contemplated. Using the conserved framework sequences surrounding the CDRs, PCR primers complementary to these consensus framework sequences are generated to amplify the CDR sequence located between the primer regions. Techniques for cloning and expressing nucleotide and polypeptide sequences are well-established in the art [see e.g., Sambrook et al., *Molecular Cloning: A Laboratory Manual*, $2^{nd}$ Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

It is contemplated that modified polypeptide compositions comprising one, two, three, four, five, or six CDRs of a heavy or light chain of an immunoglobulin are generated, wherein a CDR is altered to provide increased specificity or affinity or avidity to the target IL13Rα2. Sites at locations in the CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the target site.

Framework regions (FR) of a murine antibody are humanized by substituting compatible human framework regions chosen from a large database of human antibody variable sequences, including over twelve hundred human $V_H$ sequences and over one thousand $V_L$ sequences. The database of antibody sequences used for comparison is downloaded from Andrew C. R. Martin's KabatMan web page (http://www.rubic.rdg.ac.uk/abs/). The Kabat method for identifying CDRs provides a means for delineating the approximate CDR and framework regions of any human antibody and comparing the sequence of a murine antibody for similarity to determine the CDRs and FRs. Best-matched human $V_H$ and $V_L$ sequences are chosen on the basis of high overall framework matching, similar CDR length, and minimal mismatching of canonical and $V_H/V_L$ contact residues. Human framework regions most similar to the murine sequence are inserted between the murine CDRs. Alternatively, the murine framework region may be modified by making amino acid substitutions of all or part of the native framework region that more closely resembles a framework region of a human antibody.

"Conservative" amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E). "Insertions" or "deletions" are preferably in the range of about 1 to 20 amino acids, more preferably 1 to 10 amino acids. The variation may be introduced by systematically making substitutions of amino acids in a polypeptide molecule using recombinant DNA techniques and assaying the resulting recombinant variants for activity. Nucleic acid alterations can be made at sites that differ in the nucleic acids from different species (variable positions) or in highly conserved regions (constant regions).

Additionally, another useful technique for generating antibodies for use in the methods of the disclosure may be one which uses a rational design-type approach. The goal of rational design is to produce structural analogs of biologically active polypeptides or compounds with which they interact (agonists, antagonists, inhibitors, peptidomimetics, binding partners, and the like). In this case, the active polypeptides are antibody products specifically binding an endothelial or iPS cell. By creating analogs of such polypeptides, it is possible to fashion additional antibodies that are more immunoreactive than the native or natural molecule. In one approach, one would generate a three-dimensional structure for the antibodies or an epitope binding fragment thereof. This could be accomplished by x-ray crystallography, computer modeling or by a combination of both approaches. An alternative approach, "alanine scan," involves the random replacement of residues throughout a molecule with alanine, and the resulting effect on function is determined.

It also is possible to solve the crystal structure of the specific antibodies. In principle, this approach yields a pharmacore upon which subsequent drug design can be based. It is possible to bypass protein crystallography altogether by generating anti-idiotypic antibodies to a functional, pharmacologically active antibody. As a minor image of a mirror image, the binding site of anti-idiotype antibody is expected to be an analog of the original antigen. The anti-idiotype antibody is then be used to identify and isolate additional antibodies from banks of chemically- or biologically-produced peptides.

Chemically synthesized bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky et al., J. Exp. Med. 160:1686-701, 1984; Titus et al., J. Immunol., 138:4018-22, 1987).

Methods of testing antibodies for the ability to bind to endothelial or iPS markers, regardless of how the antibodies are produced, are known in the art and include any antibody-antigen binding assay such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Recent advances in the field of combinatorial sciences have identified aptamers, i.e., short polymer sequences (e.g., oligonucleic acid or peptide molecules) with high affinity and specificity to a given target. For example, SELEX technology has been used to identify DNA and RNA aptamers with binding properties that rival mammalian antibodies. The field of immunology has generated and isolated antibodies or antibody fragments which bind to a myriad of compounds, and phage display has been utilized to discover new peptide sequences with very favorable binding properties. Based on the success of these molecular evolution techniques, it is certain that molecules can be created which bind to any target molecule. A loop structure is often involved in providing the desired binding attributes as in the case of aptamers, which often utilize hairpin loops created from short regions without complementary base pairing, naturally derived antibodies that utilize combinatorial arrangement of looped hyper-variable regions and new phage-display libraries utilizing cyclic peptides that have shown improved results when compared to linear peptide phage display results. Thus, sufficient evidence has been generated to indicate that high-affinity ligands can be created and identified by combinatorial molecular evolution techniques, and molecular evolution techniques can be used to isolate antibody products specific for the endothelial and/or iPS cells disclosed herein. For more on aptamers, see generally, Gold, L., Singer, B., He, Y. Y., Brody. E., "Aptamers As Therapeutic And Diagnostic Agents," J. Biotechnol. 74:5-13 (2000). Relevant techniques for generating aptamers are found in U.S. Pat. No. 6,699,843, which is incorporated herein by reference in its entirety.

In some embodiments, the aptamer is generated by preparing a library of nucleic acids; contacting the library of nucleic acids with an endothelial or iPS cell marker, wherein nucleic acids having greater binding affinity for the marker (relative to other library nucleic acids) are selected and amplified to yield a mixture of nucleic acids enriched for nucleic acids with relatively higher affinity and specificity for binding to the marker. The processes may be repeated, and the selected nucleic acids mutated and rescreened, whereby a marker aptamer is identified. Nucleic acids may be screened to select for molecules that bind to more than target. Binding more than one target can refer to binding more than one simultaneously or competitively. In some embodiments, an antibody product comprises at least one aptamer, wherein a first binding unit binds a first epitope of an endothelial or iPS cell marker and a second binding unit binds a second epitope of the marker.

With regard to the antibody products of the compositions of the disclosure, attachment of endothelial and/or iPS cells to an organ or tissue scaffold is enhanced by immobilizing an antibody product to a scaffold and allowing the antibody product to facilitate the association of endothelial and/or iPS cells with the scaffold. As used herein, the term "facilitate" or "enhance" does not necessarily mean a 100% increase in the rate of association, the strength of association or the duration of association. Rather, there are varying degrees of facilitation or enhancement that one of ordinary skill in the art would recognize as having a potential benefit or therapeutic effect. Methods of measuring enhanced or facilitated association or attachment of endothelial or iPS cells to tissue or organ scaffolds are known in the art.

The antibody products according to the disclosure specifically bind to at least one endothelial cell or iPS cell marker. Endothelial cell markers contemplated by the disclosure include CD31/PECAM-1, ACE/CD143, MCAM/CD146, C1q R1/CD93, Nectin-2/CD112, VE-Cadherin, PD-ECGF/Thymidine Phosphorylase, CC Chemokine Receptor D6, Podocalyxin, Podoplanin, CD34, S1P1/EDG-1, CD36/SR-B3, S1P2/EDG-5, CD151, S1P3/EDG-3, CD160, S1P4/EDG-6, CD300LG/Nepmucin, S1P5/EDG-8, CL-K1/COLEC11, E-Selectin/CD62E, CL-P1/COLEC12, E-Selectin (CD62E)/P-Selectin (CD62P), Coagulation Factor III/Tissue Factor, P-Selectin/CD62P, DC-SIGNR/CD299, SLAM/CD150, DCBLD2/ESDN, Stabilin-1, EMMPRIN/CD147, Stabilin-2, Endoglin/CD105, TEM7/PLXDC1, Endomucin, TEM8/ANTXR1, Endosialin/CD248, Thrombomodulin/BDCA-3, EPCR, THSD1, Erythropoietin R, Tie-2, ESAM, TNF RI/TNFRSF1A, FABP5/E-FABP, TNF RII/TNFRSF1B, FABP6, TRA-1-85/CD147, ICAM-1/CD54, TRAIL R1/TNFRSF10A, ICAM-2/CD102, TRAIL R2/TNFRSF10B, IL-1 RI, VCAM-1/CD106, IL-13 R alpha 1, VE-Statin, Integrin alpha 4/CD49d, VEGF R1/Flt-1, Integrin alpha 4 beta 1, VEGF R2/KDR/Flk-1, Integrin alpha 4 beta 7/LPAM-1, VEGF R3/Flt-4, Integrin beta 2/CD18, VG5Q, KLF4, vWF-A2, or LYVE-1. An exemplary endothelial cell marker is CD31/PECAM-1.

Induced pluripotent stem (iPS) cell markers contemplated by the disclosure include 5T4, Lefty, ABCG2, Lefty-1, Activin RIB/ALK-4, Lefty-A, Activin RIIB, LIN-28A, Alkaline Phosphatase/ALPL, LIN-28B, E-Cadherin, LIN-41, Cbx2, c-Maf, CD9, c-Myc, CD30/TNFRSF8, Nanog, CD117/c-kit, Oct-3/4, CDX2, Oct-4A, CHD1, Podocalyxin, Cripto, Rex-1/ZFP42, DNMT3B, Smad2, DPPA2, Smad2/3, DPPA4, SOX2, DPPA5/ESG1, SSEA-1, EpCAM/TROP1, SSEA-3, ERR beta/NR3B2, SSEA-4, ESGP, STAT3, F-box protein 15/FBXO15, Stella/Dppa3, FGF-4, SUZ12, FGF-5, TBX2, FoxD3, TBX3, GBX2, TBX5, GCNF/NR6A1, TERT, GDF-3, TEX19, Gi24/VISTA/B7-H5, TEX19.1, Integrin alpha 6/CD49f, THAP11, Integrin alpha 6 beta 1, TRA-1-60(R), Integrin alpha 6 beta 4, TRA-1-81, Integrin beta 1/CD29, TROP-2, KLF4, UTF1, KLF5, ZIC3, or L1TD1. Exemplary iPS markers include SSEA-4, Alkaline Phosphatase/ALPL, Oct-3/4 and Nanog.

In various embodiments of the method of recellularizing a tissue or organ scaffold according to the disclosure, one or more antibody products binding an endothelial cell marker, such as the exemplary endothelial cell markers identified above, is/are used to facilitate or enhance the association or attachment of cells to the scaffold. Embodiments are also contemplated in which one or more antibody products binding an induced pluripotent stem cell marker, such as the exemplary iPS markers identified above, is/are used to facilitate or enhance the association or attachment of cells to the scaffold. In yet additional embodiments, a mixture of antibody products is contemplated for use in the methods of recellularizing a tissue or organ scaffold, i.e., at least one antibody product recognizing an endothelial cell marker in combination with at least one antibody product recognizing an induced pluripotent stem cell marker.

The disclosure will be more fully understood by reference to the following examples which detail exemplary embodiments of the disclosure. The examples should not, however, be construed as limiting the scope of the disclosure.

EXAMPLE 1

Material & Methods

The materials and methods disclosed in this Example are applicable to the studies described in Examples 1-8.

Kidney Procurement

Ten human kidneys procured for transplant purposes but eventually discarded for the reasons mentioned above, were processed. All organs were procured within the designated service area of our local organ procurement organization (Carolina Donor Services) and were refused by all local, regional, and national transplant centers. After exhaustion of the national list, kidneys from donors with research consent were offered for research purposes to the transplant team of the Wake Forest School of Medicine and processed at the Wake Forest Institute for Regenerative Medicine.

Kidney Preparation

Kidneys were received in sterile cold storage and placed in a sterile basin containing ice and preservation solution used for shipment. The aortic patch and the renal vein were prepared as for transplant purposes. The renal artery was dissected circumferentially towards the hilum of the kidney. The renal vein was dissected circumferentially and sectioned at 2 cm from its origin. In the case of multiple arteries, these were reconstructed in order to create a single arterial inlet. The excess perinephric fat was trimmed from the kidney, leaving a triangle of fat at the lower pole. The perihilar fat and lymphatic tissue was ligated with 2-0 silk ties. Sixteen gauge intravenous catheters were inserted into the ureter and the renal artery and secured with 2/0 silk suture to allow perfusion. Thereafter, the renal artery and ureter were tested for possible leaks and repaired with 6-0 Prolene figure-of-eight sutures. Because all kidneys had been biopsied at the upper pole at the time of procurement, a renorrhaphy of the "wedge" defect was performed with 4-0 PDS suture in a running fashion. Kidneys were finally placed on ice until decellularization.

Decellularization—Kidney (One Protocol)

At room temperature, the angiocatheters previously inserted in the renal artery and in the ureter were connected to a pump (Masterflex L/S peristaltic pump with Masterflex L/S easy load pump head and L/S 16G tubing, Cole-Palmer Instrument Co, Vernon Hills, Ill., USA) to allow continuous rinsing with different solutions, starting with distilled water at a rate of approximately 12 ml/min for 12 hours (8,640 mL total), as previously described[12]. Afterward, 0.5% sodium dodecyl sulphate (SDS)-based solution was delivered at the same flow rate for 48 hours (34,560 mL total) in both the renal artery and ureter. Finally, the kidneys were rinsed with phosphate buffer saline (PBS) for 5 days at a flow rate of 6 mL/min (43,320 mL total).

Decellularization—Kidney (Another Protocol)

Kidneys are received in sterile cold storage and placed in a sterile basin containing ice and preservation solution used for shipment. The aortic patch and the renal vein are prepared for research in the manner prepared for transplant purposes. The renal artery is dissected circumferentially towards the hilum of the kidney. The renal vein is dissected circumferentially and sectioned at 2 cm from its origin. The excess perinephric fat is trimmed from the kidney, leaving a triangle of fat at the lower pole. The perihilar fat and lymphatic tissue is ligated with 2-0 silk ties. Sixteen gauge intravenous catheters are inserted into the ureter and the renal artery and secured with 2/0 silk suture to allow perfusion. Thereafter, the renal artery and ureter are tested for possible leaks and repaired with 6-0 Prolene figure-of-eight sutures. Because all kidneys are biopsied at the upper pole at the time of procurement, a renorrhaphy of the "wedge" defect is performed with 4-0 PDS suture in a running fashion. Kidneys are finally placed on ice until decellularization.

At room temperature, the angiocatheters previously inserted in the renal artery and in the ureter were connected to a pump (Masterflex L/S peristaltic pump with Masterflex L/S easy load pump head and L/S 16G tubing, Cole-Palmer Instrument Co, Vernon Hills, Ill., USA) to allow continuous rinsing with different solutions, starting with distilled water at a rate of approximately 12 ml/min for 12 hours (8,640 mL total). Afterward, 0.5% sodium dodecyl sulfate (SDS)-based solution was delivered at the same flow rate for 48 hours (34,560 mL total) in both the renal artery and ureter. After decellularization with SDS, 1000 mL of DNase solution (0.0025 w/w % DNase [Sigma-Aldrich, DN25] and 10 mm magnesium chloride [Sigma-Aldrich, M4880] in 1×PBS at neutral pH) are re-circulated through the hrECMs overnight to allow digestion of residual DNA. Thereafter, hrECMs are rinsed with phosphate buffer saline (PBS) for 5 days at a flow rate of 6 mL/min (43,320 mL total). Finally, the resulting hrECMs are stored in PBS and, eventually, gamma-irradiated to achieve sterilization.

Decellularization—Pancreas

First, the pancreata are procured with the duodenum and the spleen attached. Pancreata are received in sterile cold storage and placed in a sterile basin containing ice and preservation solution used for shipment. For research purposes, the splenic artery and the superior mesenteric artery are prepared as for transplant purposes. Then, the duodenum is removed to allow identification of the pancreatic duct, which is "buried" in the duodenum. Likewise, the spleen is removed, after ligation and section of the distal segment of the splenic vein and artery, as well as of the short gastric arteries. The excess peripancreatic fat and lymphatic tissue are ligated with 2-0 and 3-0 silk ties, and trimmed from the organ thereafter. Sixteen gauge intravenous catheters are inserted into the splenic artery, the superior mesenteric artery and the pancreatic duct and secured with 3/0 silk sutures to allow perfusion. Thereafter, the two arteries and the duct are tested for possible leaks and repaired with 6-0 Prolene figure-of-eight sutures. The organ is finally placed on ice until decellularization.

Decellularization takes place in the following steps:

1. Wash with 10% povidone-iodine (betadine) for 10 minutes. In one embodiment, the organ is put in a basin containing povidone-iodine (betadine) in order to kill bacteria.

2. Wash with 10% Penicillin/Streptomycin for 10 minutes. Wash with 10% antibiotics for 10 minutes.

3. Rinse with 500 mL sterile PBS.

4. Place pancreas in container, connect lines and secure with silk sutures. For example, one line goes into the pancreatic duct and the second one is split into two (the first one is connected to the superior mesenteric artery and the second one goes into to the splenic artery).

5. Pre-fill the container and prime the pancreas with PBS and Heparin (1% of 1000 U, 10U/mL).

6. Seal the container and place in a refrigerator (4° C.).

7. Flush the pancreas with PBS and Heparin (1% off 1000 U, 10U/mL) for 15 minutes at a rate of 0.75 L/hr in each inlet (total PBS volume is 187.5 ml for the pancreatic duct and 93.75 ml for mesenteric artery and splenic artery).

8. Flush the pancreas with 1% non-ionic detergent (Triton) and 0.1 ammonium hydroxide in PBS for 48 hours at a rate of 0.75 L/hr in each inlet (total volume is 36 L for the pancreatic duct and 18 L for the mesenteric and the splenic artery).

9. Flush the tissue or organ with PBS for 4 days at a rate of 0.375 L/hour in each inlet.

10. Flush for 24 hours with PBS and 1% Penicillin/Streptomycin and Gentamicin at a rate of 0.375 L/hour in each inlet.

11. Flush for 4 hours with DNase and 0.0025% magnesium chloride at a rate of 0.375 L/hour in each inlet.

12. Flush for 12 hours with PBS at a rate of 0.375 L/hour in each inlet.

Bioscaffold Characterization

Basic Histology

To assess cell and nuclear clearance as well as preservation of collagen fibrils, hematoxylin and eosin (H&E), Masson's trichrome (Newcomer Supply, Middleton, Wis., USA) and nuclear-specific 4,6-diamidino-2-phenylindole (DAPI) staining were performed after fixation in formalin 10%, paraffin embedding and sectioning. We expected nuclei and cells to be completely removed and collagen fibrils to be preserved.

Immunohistochemistry (IHC)

Tissue slides were fixed in 4% paraformaldeyhyde, quenched for endogenous peroxidase in 70% Methanol plus 0.3% Hydrogen Peroxide, blocked with protein blocker (Dako, X090930) and incubated with primary antibodies diluted in antibody diluent (Dako S0809) for 1 hour at room temperature. Tissue slides were washed in 3×PBS, incubated with secondary antibodies for 30 minutes at room temperature, washed with 3×PBS and incubated with ABC reagent (Vector Elite ABC Reagent, Vector PK-7100). Target proteins detection was visualized by adding DAB reagent (Vector ImmPACT DAB Peroxidase Substratek, Vector SK-4105). Cell nuclei were counterstained by hematoxylin.

Antibodies for Immunostaining

1) Primary antibodies for immunostaining included: Anti-HLA DR [LN-3] (Abcam Ab49388, 1:50), Anti-HLA class 1 ABC[EMR8-5] (Abcam ab70328, 1:50), Type IV collagen (Developmental Studies Hybridoma Bank, M3F7, 1:100, which binds to the triple helical domain of collagen alpha1 and alpha2 chains), Anti Collagen IV [COL-94] (Abcam Ab6311, 1:50), Anti collagen IV alpha3 (Sigma SAB4500376, 1:50), COL4A4[G-12] (Santa Cruz sc-167524, 1:50), Anti-Agrin (Abcam Ab85174, 1:100), COL4A5 [H-234] (Santa Cruz sc-11360, 1:50), COL4A6 [H-299] (Santa Cruz sc-134614, 1:50), Nidogen-1/Entactin (R &D system AF2570, 1:50), Nidogen-2 (R &D system AF3385, 1:50), Laminin alpha1 (LAMA1)(Lifespan Biosciences LS-C25112/34991, 1:50), Laminin alpha5 (LAMAS) (Lifespan Biosciences LS-C119651/28195, 1:100), Laminin a5-chain (Millipore MAB 1924, 1:100), Laminin (Millipore MAB1921, 1:50), Anti-integrin alpha3/beta1 [P1B5] (Abcam Ab24696, 1:100).

2) Secondary antibodies included biotinylated goat anti-rabbit IgG (1:200) (Vector), biotinylated goat anti-mouse IgG (Vector), biotinylated goat anti-rabbit IgG (1:200) (Vector), biotinylated goat anti-mouse IgG (1:200) (Vector). Target protein detection reagents included VECTASTAIN Elite ABC Reagent, R.T.U. (Vector PK-7100) and ImmPACT DAB Peroxidase Substrate (Vector SK-4105), which were used for IHC staining. Positive staining (typically black) was the expected result.

Scanning Electron Microscopy (SEM)

A segment of decellularized kidney incorporating both medulla and cortex was fixed in 2% glutaraldehyde in 0.1 M phosphate buffer and left for 24 hours at 3° C. Following washing with 0.1 M phosphate buffer, 0.5 cm$^2$ pieces of tissue were sampled from both the medulla and cortex and cryoprotected in 25% sucrose, 10% glycerol in 0.05 M PBS (pH 7.4) for 2 hours, then fast frozen in nitrogen slush and fractured at approximately −160° C. The samples were then placed back into the cryoprotectant at room temperature and allowed to thaw. After washing in 0.1 M phosphate buffer (pH 7.4), the material was fixed in 1% $OsO^4$/0.1 M phosphate buffer (pH 7.3) at 3° C. for 1.5 hours and washed again in 0.1 M phosphate buffer (pH 7.4). After rinsing with distilled water, specimens were dehydrated in a graded ethanol-water series to 100% ethanol, critical point dried using $CO^2$ and finally mounted on aluminum stubs using sticky carbon taps. The material was mounted to present the fractured surfaces to the beam. The complete samples were opened and mounted to show the fractured surface, then coated with a thin layer of Au/Pd (approximately 2 nm thick) using a Gatan ion beam coater. Images were recorded with a Jeol 7401 FEG scanning electron microscope.

DNA Quantitation

The DNA content of fresh and decellularized kidney was quantified using the tissue DNA isolation kit (PureLink Genomic DNA MiniKit, Invitrogen) according to the manufacturer's instructions. Briefly, the samples were digested overnight using Proteinase K and a digestion buffer. Upon removal of RNA, DNA samples were isolated by spin column-based nucleic acid purification and the extracts were characterized spectrophotometrically (NanoDrop 1000; Thermo Scientific). Optical densities at 260 nm and 280 nm were used to estimate the purity and yield of nucleic acids, which were quantified on the basis of 280 nm absorbance.

Glycosaminoglycan and Collagen Quantification

The sulfated glycosaminoglycan (GAG) content of fresh and decellularized kidneys was quantified using the Blyscan GAG Assay Kit (Biocolor, UK). In brief, 30 mg of minced wet tissue were digested in papain-containing digestion buffer for 18 hours at 65° C. Aliquots of each sample were mixed with 1,9-dimethyl-methylene blue dye and reagents from the GAG assay kit. The absorbance at 595 nm was measured using a microplate reader (Tecan Infinity) and compared to standards made from bovine tracheal chondroitin-4-sulfate to determine the absolute GAG content.

The collagen content was measured indirectly through measurement of hydroxyproline residues using the QuickZyme total Collagen Assay (QuickZyme, Biosciences). Five mg of tissue was acid-hydrolyzed overnight with 6 M HCl at 95° C., following assay as described by the manufacturer. Hydroxyproline content resulted in a chromogen with an absorbance maximum at 570 nm, which was measured using a microplate reader (Tecan Infinity). The absolute collagen content was determined by comparison to standards from hydrolyzed collagen (1200 µg/ml in 0.02M acetic acid).

Chicken Chorioallantoic Membrane (CAM) Angiogenic Assay

The CAM was performed essentially as previously described [28, 29]. Fertilized chicken eggs (Henry Stewart and Co., UK) were incubated at 37° C. and constant humidity. At 3 days of incubation an artificial air sac was created by aspirating 2 ml of albumin from the acute end of the egg using a 21-G gauge needle. An oval window of approximately 3 cm in diameter was opened in the shell with small dissecting scissors to reveal the embryo and CAM vessels. The window was sealed with tape and the eggs were returned to the incubator for a further 5 days. At day 8 of incubation, 1 mm diameter samples of kidney acellular ECM (3 samples) or polystyrene (three samples) as a negative control, were placed on the CAM between branches of the blood vessels. Grafts were examined daily until 7 days after placement wherein they were photographed with a stereomicroscope equipped with a Camera System (Leica) both in ovo and after removal and pinning in a silicone rubber-coated dish, to quantify the blood vessels surrounding the matrices. The number of blood vessels less than 10 µm in diameter converging towards the placed tissues was counted blindly by assessors (scaffold n=3, polystyrene n=3, assessors n=3).

Pressure Measurement

To test the compliance of vascular network of the human renal ECM scaffolds, native and decellularized kidney samples were perfused with water through the cannulated renal artery using a peristaltic pump (Masterflex 7523-70, Cole-Parmer) and pulse dampener (Cole-Parmer) to create steady flow. Pressure was measured and recorded using a Millar MPC-500 Mikro-Tip pressure transducer with MPVS-400 signal conditioning hardware (Millar Instruments Inc.) and integrated data acquisition technology (Powerlab, ADInstruments). The pressure probe was inserted into the renal artery and pressure was recorded at flow rates ranging from 10 ml/min to 30 ml/min in 5 native and 6 decellularized kidneys. All probes were calibrated to mmHg before each use.

EXAMPLE 2

Human Kidney Decellularization

Perfusion of SDS-contained buffer successfully decellularized human kidneys discarded from transplantation. DNA confirmed this observation and showed that approximately 95% of DNA was removed in comparison with the native organ (12.27±0.7 vs. 274.7±4.7, p<0.0003). On the other hand, measurements of glycosaminoglycans (GAGs) demonstrated a decrease from 0.89±0.18 µg/mg to 0.55±0.21 µg/mg, equal to a reduction to 60% of the fresh value (p=ns). Similar results were observed for the amounts of collagen remaining in the acellular ECM scaffolds.

EXAMPLE 3

Histological Characterization of the Human Renal ECM Scaffold

Figure 2:
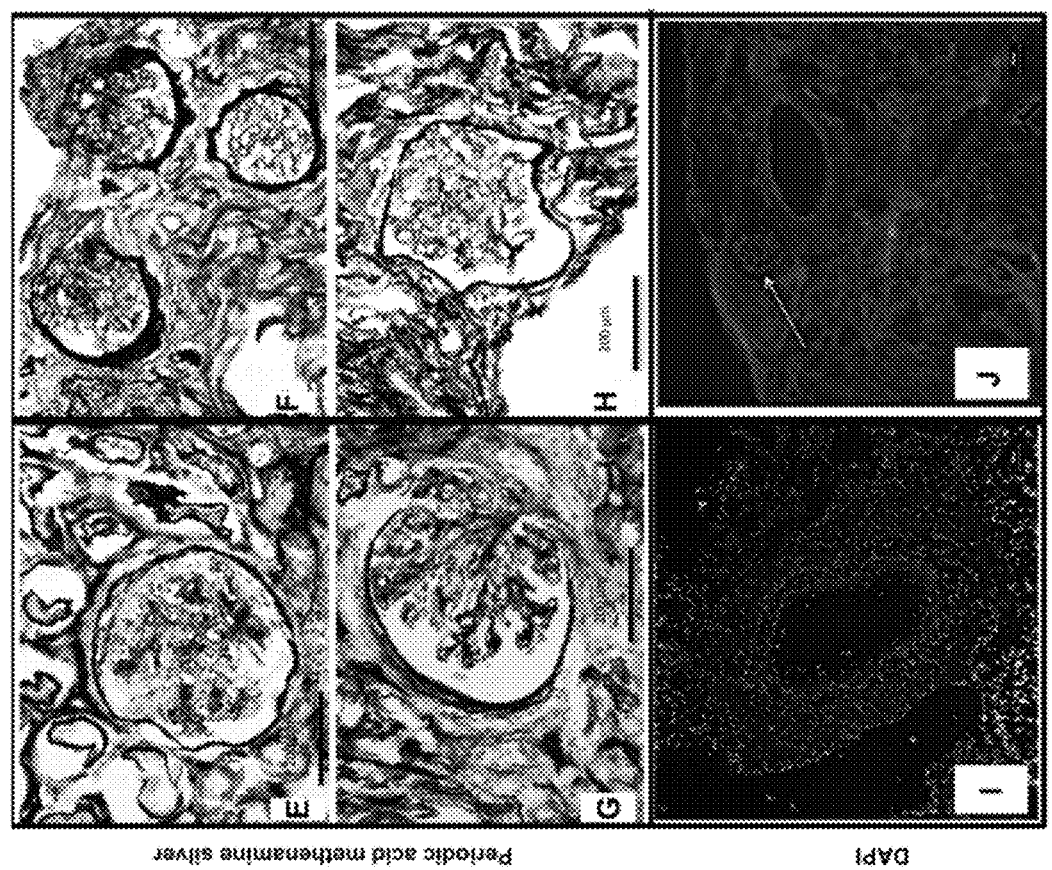
FIG. 2. Histological examination of decellularized human kidneys. H&E, Masson trichrome, methenamine silver and DAPI staining of native (A, C, E, G, I) and acellular (B, D, F, H, J) human kidneys. Cell and nuclear material are well cleared as demonstrated by the total lack of nuclei and cellular components or debris. The inset in B shows an example of a severely sclerotic glomerulus that is now completely acellular. Arrow in panel J shows the intact framework of a glomerulus.
Figure 2:
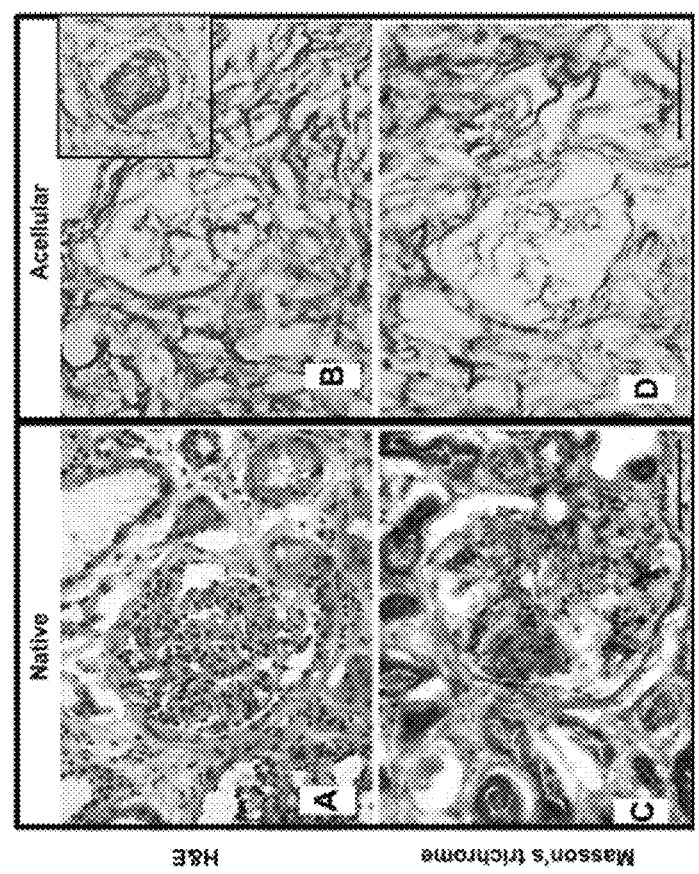

H&E staining of the decellularized kidney tissue showed pink eosinophilic staining typical of collagen while no basophilic staining indicative of cellular nuclear material was detected (FIGS. 2A, B). The scaffolding architecture of glomeruli, vessels and tubules was preserved. Notably, our decellularization protocol allowed cell clearance despite severe glomerulosclerosis and interstitial fibrosis. FIG. 2B shows an acellular glomerulus at an advanced degree of ischemic collapse with a remnant of the corrugated glomerular basement membrane of the collapsed tuft and surrounded by the thickened and multilayered Bowman capsule basement membrane. Masson's trichrome stain confirmed these results, showing a homogenous blue staining of the ECM consistent with collagen (FIGS. 2C, D). This indicates that the disclosed method allows detergents to reach all cellular compartments despite advanced fibrosis. Methenamine silver staining was performed in order to assess preservation of glomerular basement membrane (GBM), which is an essential structure of renal ECM scaffolds situated between endothelial cells and podocytes. This membrane derives from the fusion of the endothelial cell and podocyte basal laminas and represents the basal laminal portion of the glomerulus that performs the actual filtration through the filtration slits between the podocytes, separating the blood on the inside from the filtrate on the outside. The methenamine silver staining revealed the presence of a well preserved GBM (FIGS. 2E-H), which was often thick because of severe glomerulosclerosis in these discarded kidneys. To further assess the decellularization efficiency, cell nuclei staining was performed using DAPI, and confirming successful clearance of cells and nuclear material (FIGS. 2I-J).

EXAMPLE 4

Removal of Antigenic Markers

Figure 3:
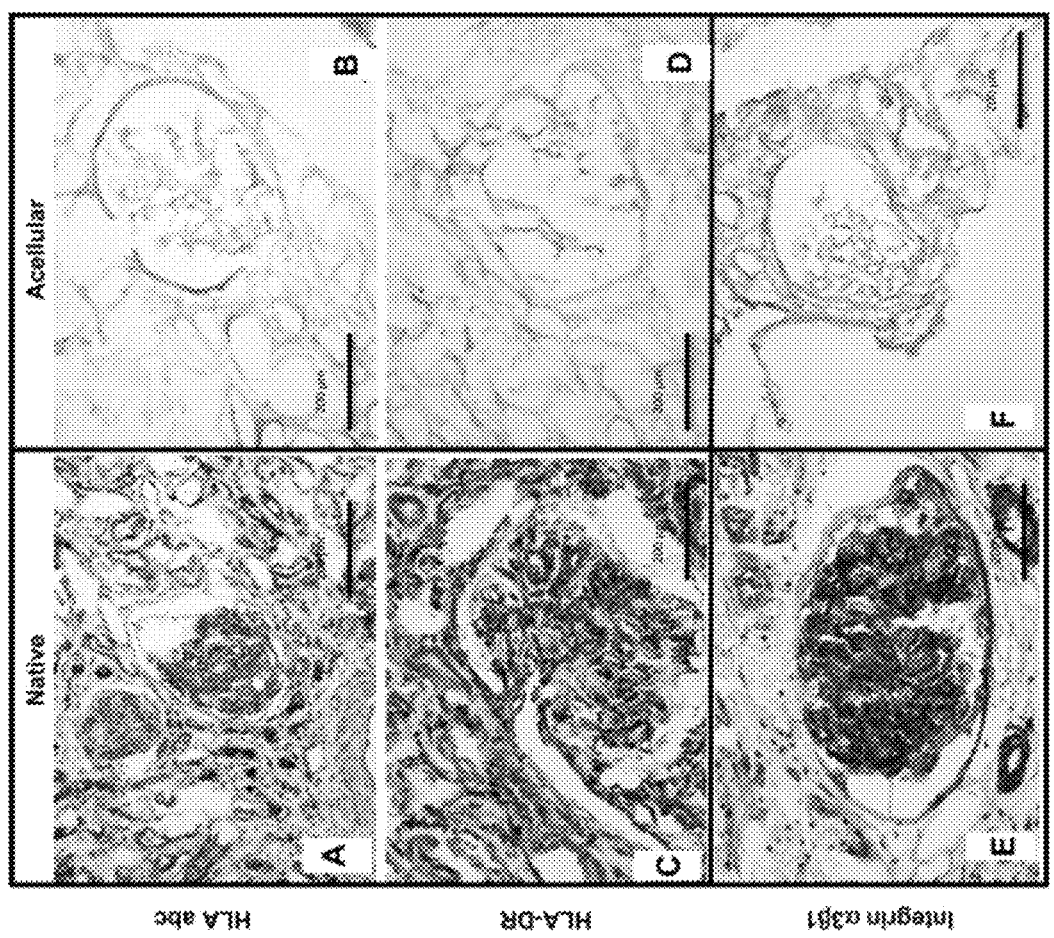
FIG. 3. Removal of antigenic markers. Immunostaining for HLA ABC (class I, A, B), HLA DR (class II, C, D) antigens and integrin a3b1 (E, F) in native (A, C, E) and acellular (B, D, F) human kidneys. The staining of these antigenic markers is completely absent in the acellular ECM scaffolds.

The HLA system is the major histocompatibility complex in humans. ABC antigens represent the human major histocompatibility complex class I, while DR antigens are members of class II. They are heavy chain receptors expressed in nearly all cells whose role is to help the immune system distinguish the body's own proteins from non-self proteins. HLA class I antigens (A, B, and C) present peptides from inside the cell, while HLA class II (DR) present antigens from outside of the cell to T-lymphocytes [32]. Immunostaining for HLA-ABC and HLA-DR showed that the antigens were completely removed upon decellularization, whereas they strongly present in the native kidneys (FIGS. 3A-D). This finding has a significant immunological implication, as it indicates that human renal ECM scaffolds may have only minimal if not negligible immunogenicity, possibly limited to a non-specific inflammatory response. Integrin $\alpha 3/\beta 1$ are transmembrane heteromeric receptors that mediate interactions between cells and ECM, are highly expressed in the glomerulus of the kidney, and are key players in glomerular morphogenesis and maintenance of glomerular filtration barrier integrity. Similar to the efficient removal of the HLS-ABC and HLA-DR antigens, the decellularization protocol efficiently removed integrin $\alpha 3/\beta 1$ in the acellular human renal ECM scaffolds (FIGS. 3E, F).

EXAMPLE 5

Immunohistochemical Characterization of the Human ECM Renal Scaffolds

Figure 4:
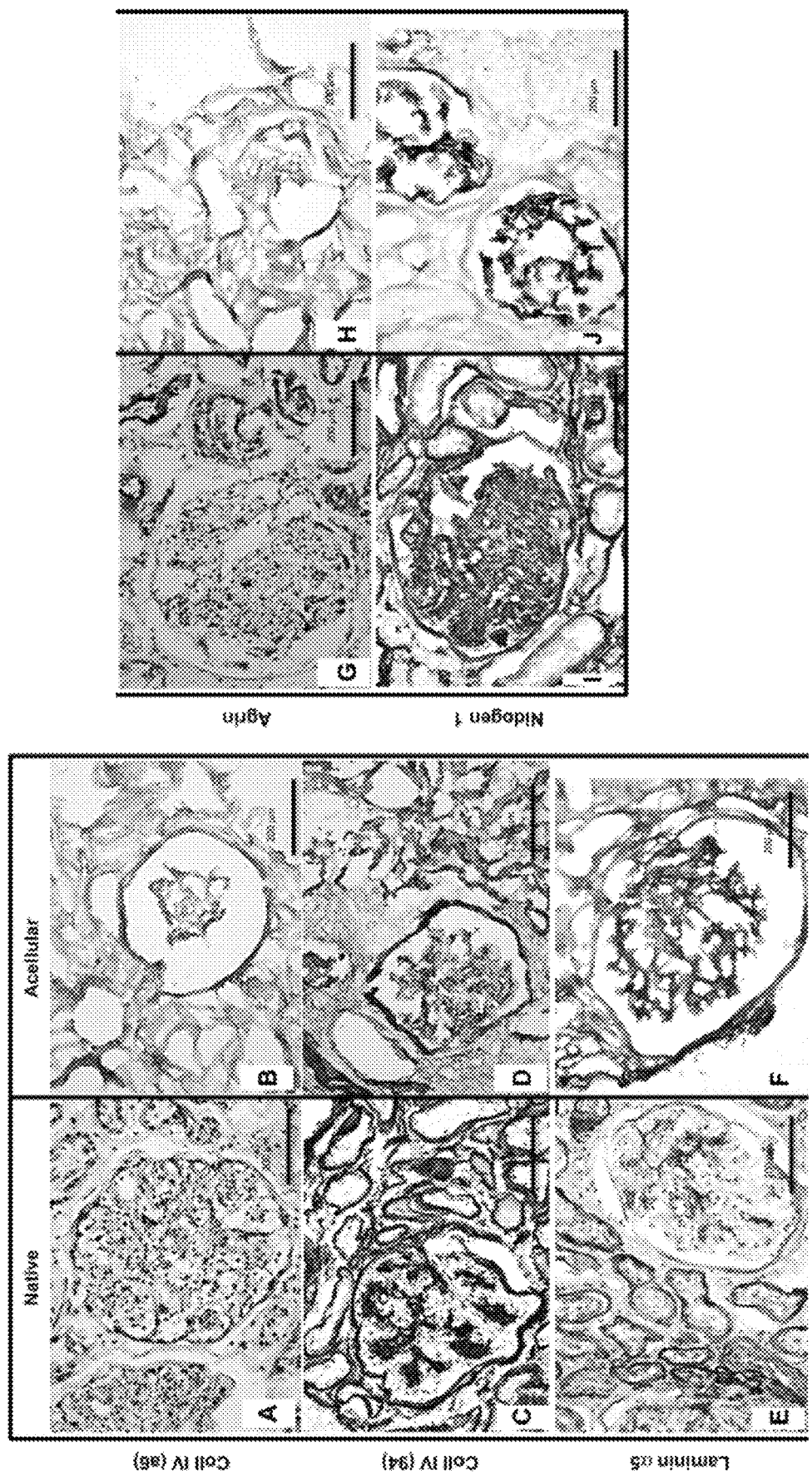
FIG. 4. Preservation of ECM molecules. Immunostaining for Collagen type IV (AeD), laminin alpha5 (EeF), agrin (GeH) and nidogen (IeJ) in native (A, C, E, G, I) and acellular (B, D, F, H, J) human kidneys. The natural location of these ECM molecules is shown in the native kidneys. There is well-preserved expression of the ECM molecules following the decellularization process, and they remained in their natural locations.

Type IV collagen (Coll IV) is the major structural component of GBM together with laminins, proteoglycans and nidogen. Laminins are ubiquitous basement membranes. The most important receptors for laminin $\alpha 5$ are the integrin family. Agrin is the major heparan sulfate proteoglycan of the GBM playing a key role in the renal filtration and cell-matrix interactions. Nidogen 1 and 2 are both dumbbell-shaped, virtually ubiquitous basement membrane proteins, binding to the short arm of laminin $\gamma 1$ as well as to Coll IV. Staining for Coll IV, with 2 different anti-Coll IV antibodies, showed preservation of Coll IV in the GBM (FIG. 4A-D). Laminin $\alpha 5$ was also preserved after decellularization of the human kidneys, and its preservation is important for successful cell attachment on the renal scaffolds (FIG. 4E-F). Agrin and nidogens were also well preserved (FIG. 4G-J).

EXAMPLE 6

Ultrastructural Analysis

Figure 5:
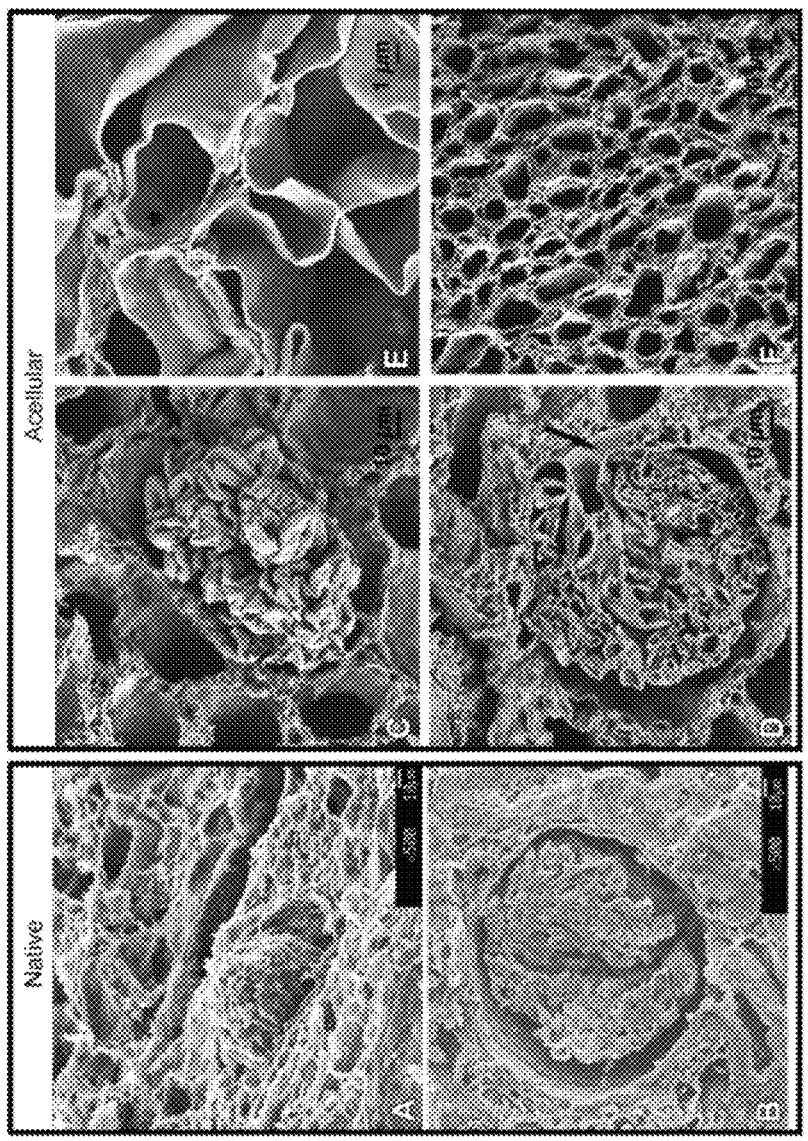
FIG. 5. Infrastructural analysis. Scanning electron microscope images of native (A, B) and acellular (C, D, E, F) human kidneys. The images indicate good preservation of the ultrastructure in the acellular ECM scaffolds, compared with the native kidneys. No cellular remnants can be detected on the acellular matrix.

SEM confirmed the successful clearance of the cellular compartment of human kidneys (FIGS. 5C-F). No cells or nuclei could be observed, while the remaining acellular ECM scaffold maintained the ultrastructural characteristics of the native tissue (FIGS. 5A-B). The three-dimensional architecture of the kidneys was well preserved including all of the essential structures—namely, glomeruli, tubules and vessels of any hierarchical level, which were well represented and evident. Lower magnification images of a single renal corpuscle show the integrity of the glomerulus with its winding blood capillary loops (FIGS. 5C-D). The capillary wall is intact and no podocytes are present on the outer surface (FIG. 5C). SEM view of the microdissected glomeruli showed the convoluted GBM and the vascular pole where the afferent arteriole integrates with the glomerulus (arrow) (FIG. 5D). The surface of the GBM, under higher magnification, is regular and no cellular elements could be observed (FIG. 5E). The internal surface of the parietal layer of the Bowman's capsule appeared like a flat, regular surface where no epithelial cell could be detected. A transversal section of the sample of renal ECM gave a honeycomb-like image of the complex network of arterioles and tubules, which composes the nephron structure in the mammalian kidney and was well preserved in the decellularized tissue (FIG. 5F).

EXAMPLE 7

Induction of Angiogenesis

Figure 6:
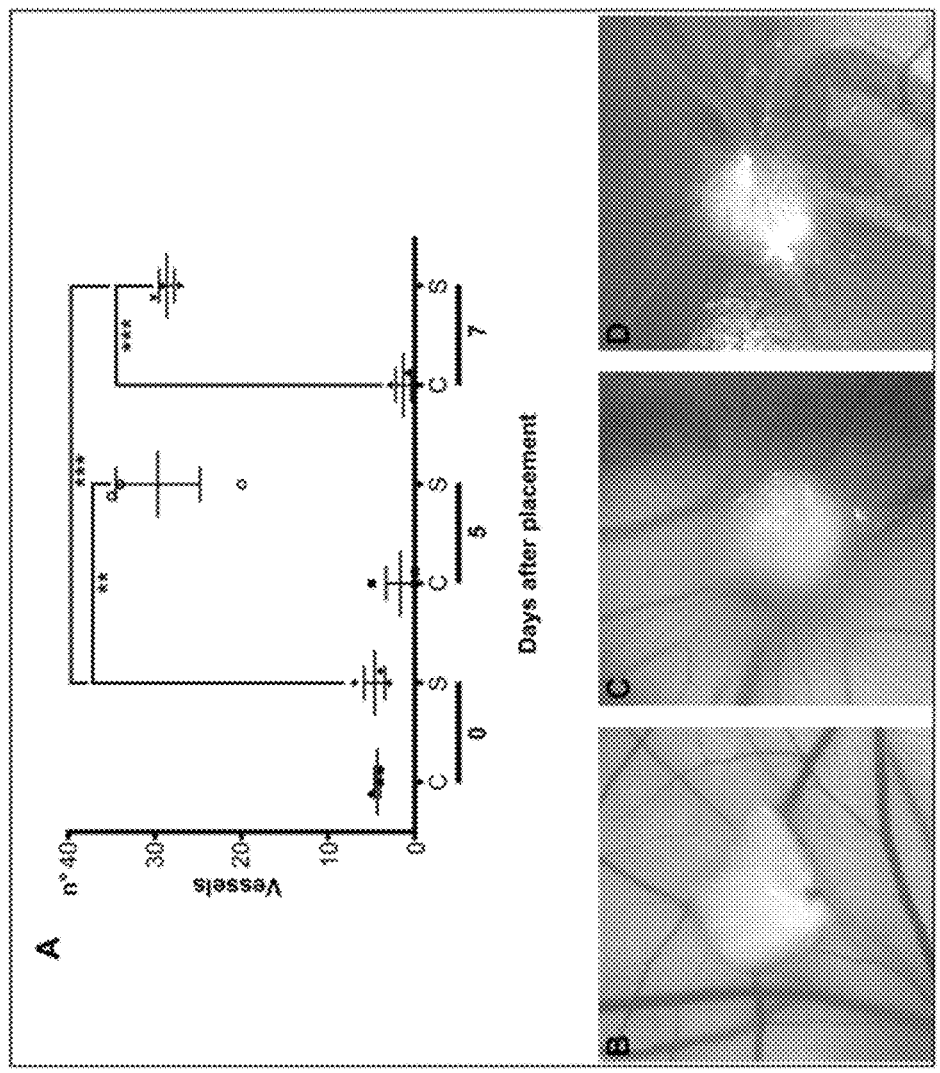
FIG. 6. Angiogenic induction. The angiogenic potential of the renal ECM scaffolds was tested using CAM assay. Images of the scaffolds placed on the chorioallantoic membrane from day 0, 5, and 7 (B, C and D, respectively) show progressive attraction of blood vessels towards the ECM scaffold. The number of vessels induced by the implantation of ECM versus control (polystyrene membranes) was calculated from these images (A).

The chorioallantoic membrane (CAM) of chicken embryos is a highly vascularized structure normally adherent to the egg shell and responsible for gas exchange, and thus, used in in vivo assay to determine the angiogenic/antiangiogenic activities of biomaterials and other compounds. Macroscopic observation of the CAM at day 0 showed the renal ECM scaffold on top of the allantoic vessels beneath, but without vessels penetrating the scaffold (FIG. 6B). Five days later the scaffold had changed color to a yellowish hue, was well-adherent to the CAM and new vessels of the CAM had begun penetrating renal ECM scaffolds (FIG. 6C). At 7 days, the ECM scaffolds were completely enveloped by the CAM and the vessels, which formed an organized network around the scaffolds (FIG. 6D). The pro-angiogenic effect of the renal ECM scaffolds was quantified at day 0, 5 and 7 in a blinded fashion. Human renal ECM scaffolds induced the onset of a significantly higher number of vessels, both from longitudinally (i.e., from time 0 to day 7) and versus the control. At day 0 (time of transplantation) no vessels growing towards the implanted tissues were observed. At day 5 the renal ECM scaffolds significantly stimulated the growth of converging allantoic vessels compared to day 0 (p=0.007). A further increase was observed at day 7, with the number of converging allantoic vessels significantly higher when compared to day 0 (p<0.0001) and to the control polystyrene membranes at the same time-point (p<0.0001; FIG. 6A).

EXAMPLE 8

Resistance to Vascular Pressures

Figure 7:
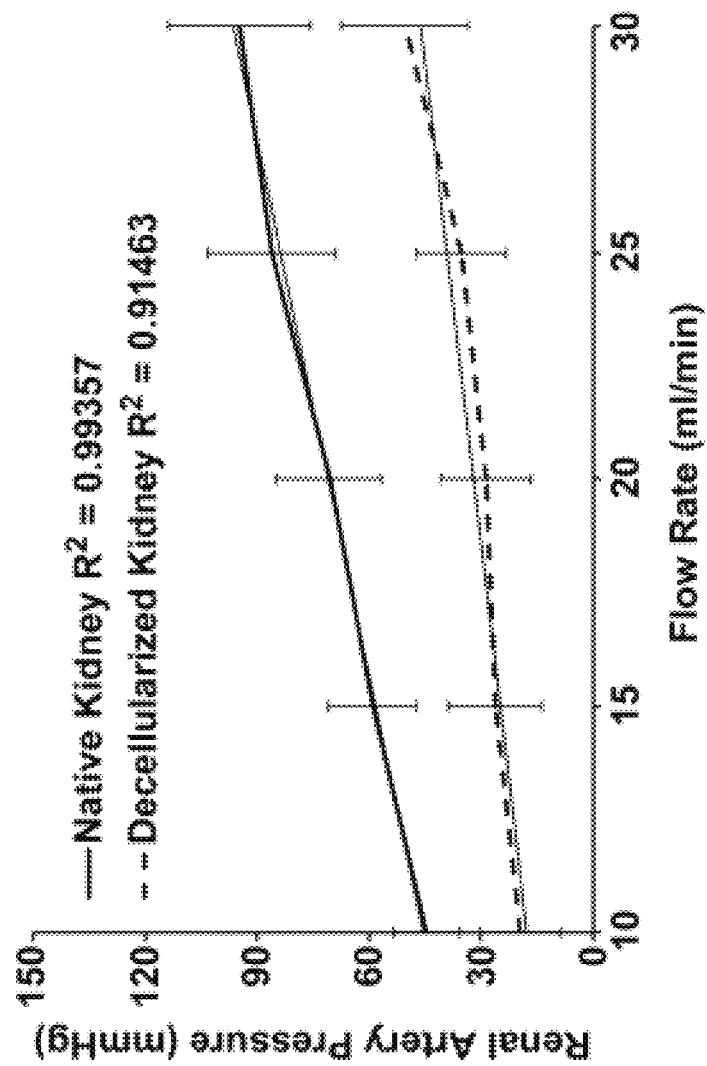
FIG. 7. Resistance to vascular pressures. Pressures within the renal artery in acellular human renal ECM scaffolds increased linearly with flow rate, similar to native kidneys. Linear regression calculation shows similar trends, which however significantly differ between native and acellular kidneys.
Figure 8:
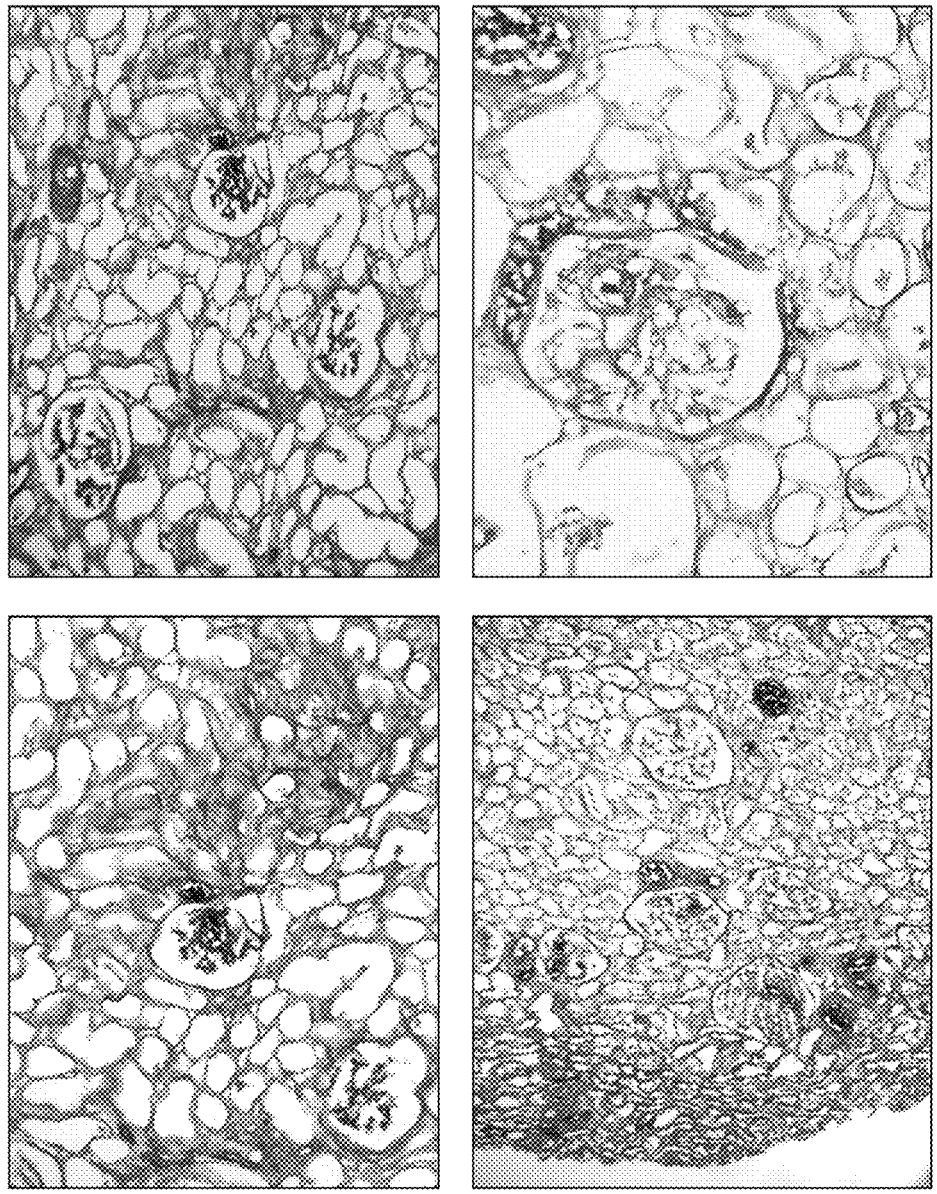
FIG. 8. Hemotoxylin & Eosin staining of kidney tissue post-decellularization obtained by arterial perfusion only. Cell clearance is not complete, as revealed by the presence of cells and nuclei detected in glomeruli as well as in other zones of the kidney parenchyma.
Figure 9:
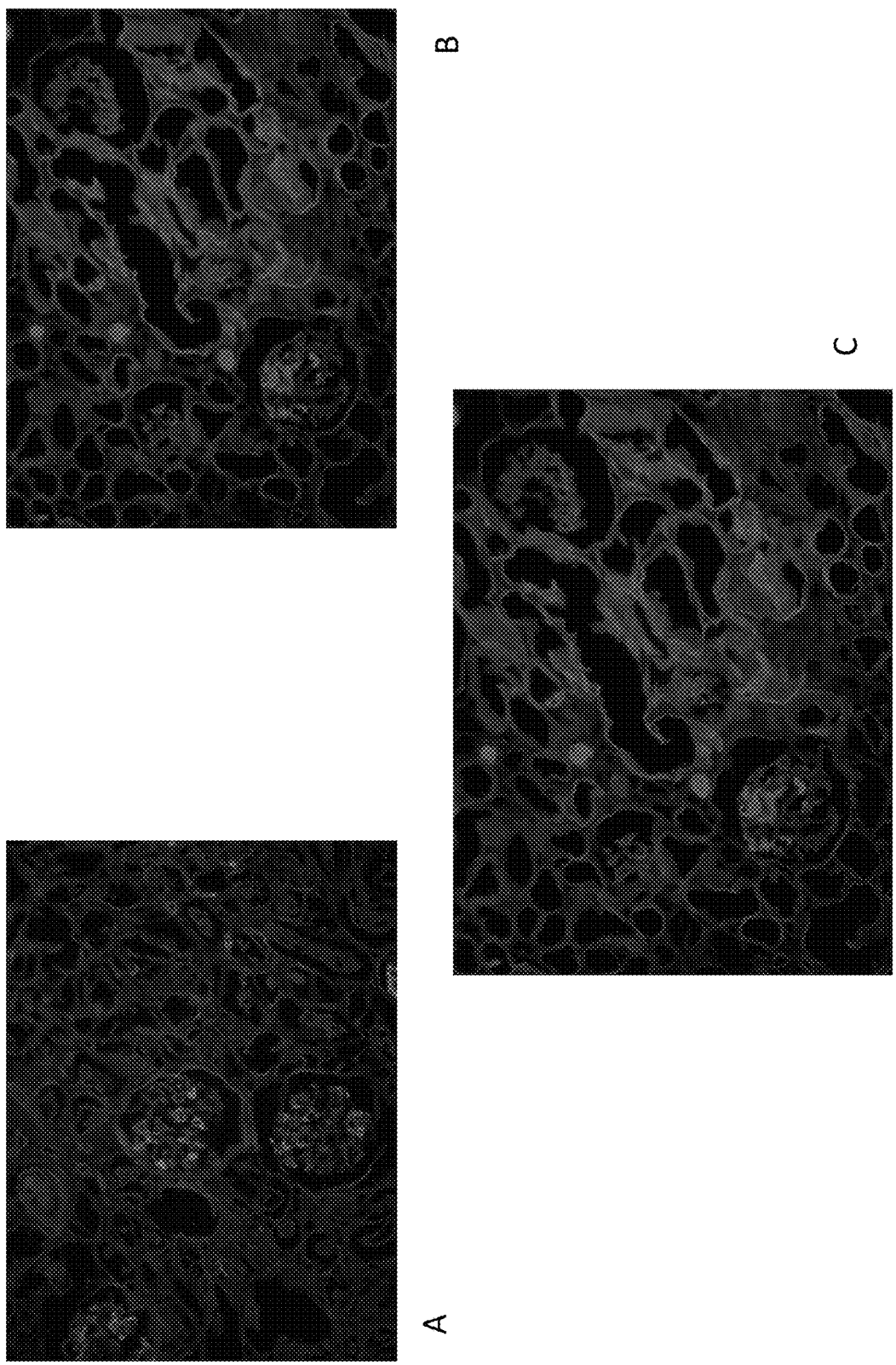
FIG. 9. DAPI staining of kidney tissue post-decellularization obtained by arterial perfusion reveals the presence of cells, as indicated by fluorescence (bright dots) staining of cell nuclei.
Figure 10:
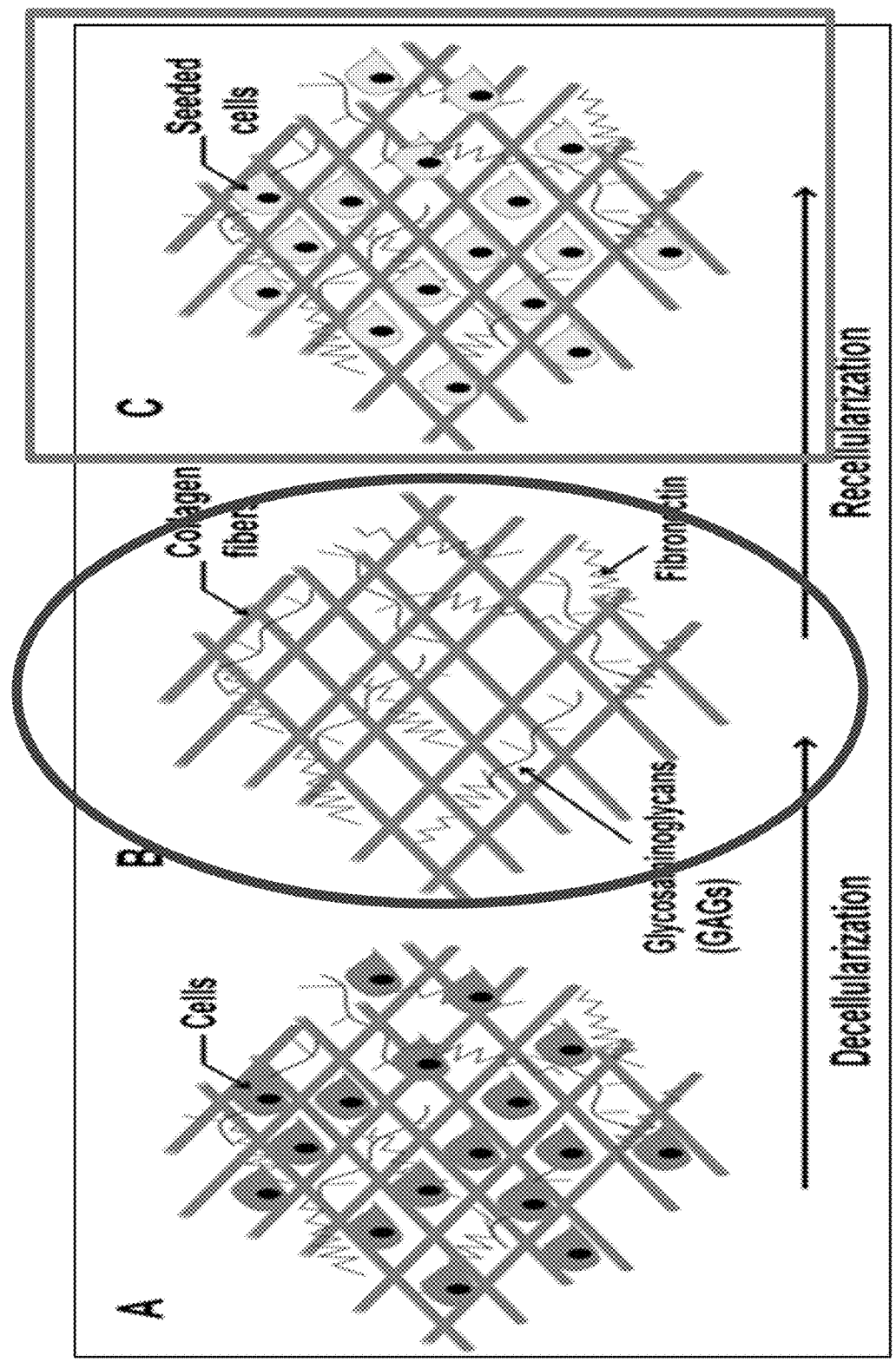
FIG. 10. Schematic illustration of organ or tissue decellularization.
Figure 11:
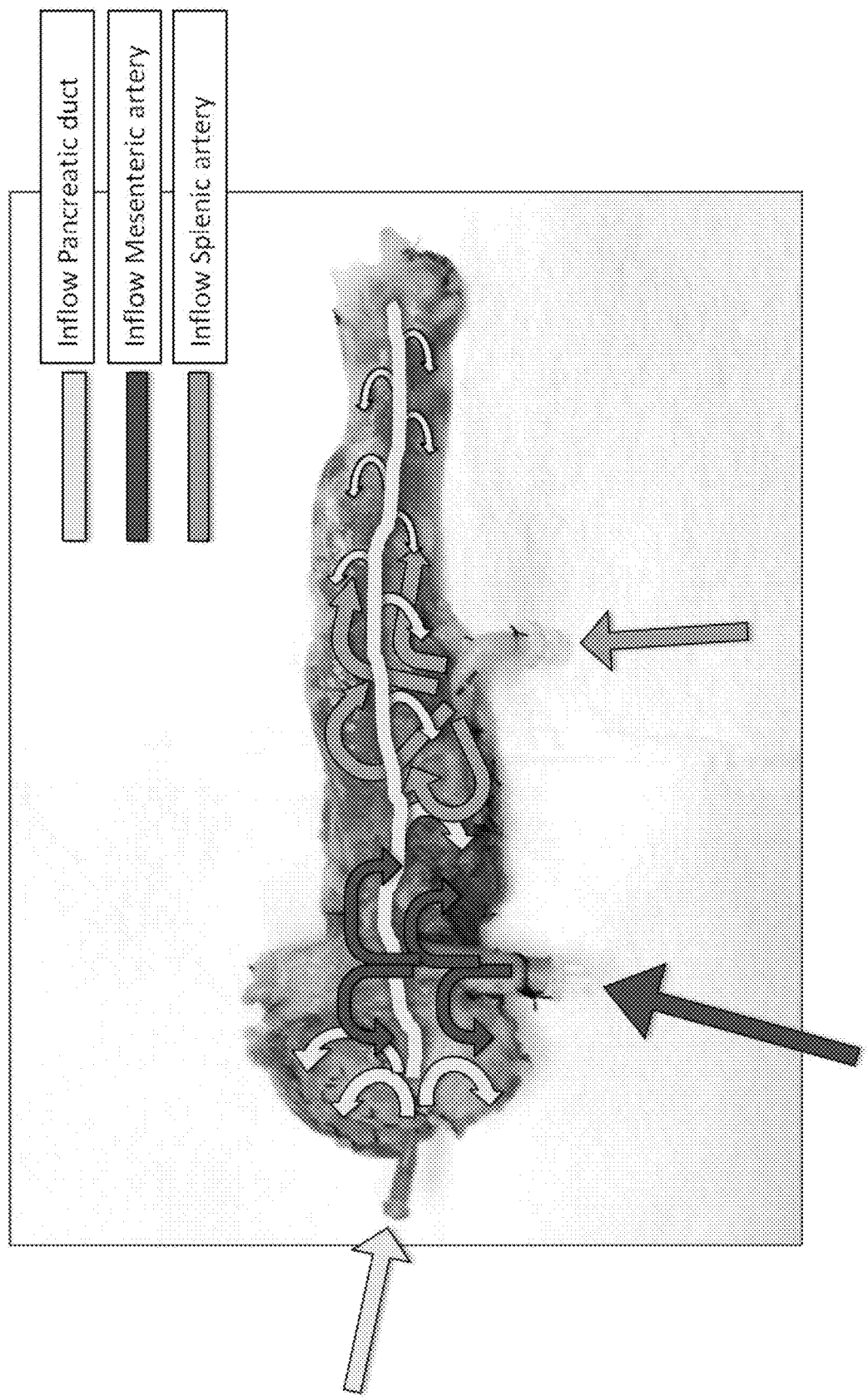
FIG. 11. Pancreas decellularization through three different inlets, i.e., the pancreatic duct, the superior mesenteric artery and the splenic artery. Arrows show the direction of flow and the territory to be rinsed with detergent.
Figure 12:
FIG. 12. Gross appearance of the human pancreas post-decellularization. In the case of human organs, the scaffold or acellular organ does not look perfectly white or whitish.
Figure 13:
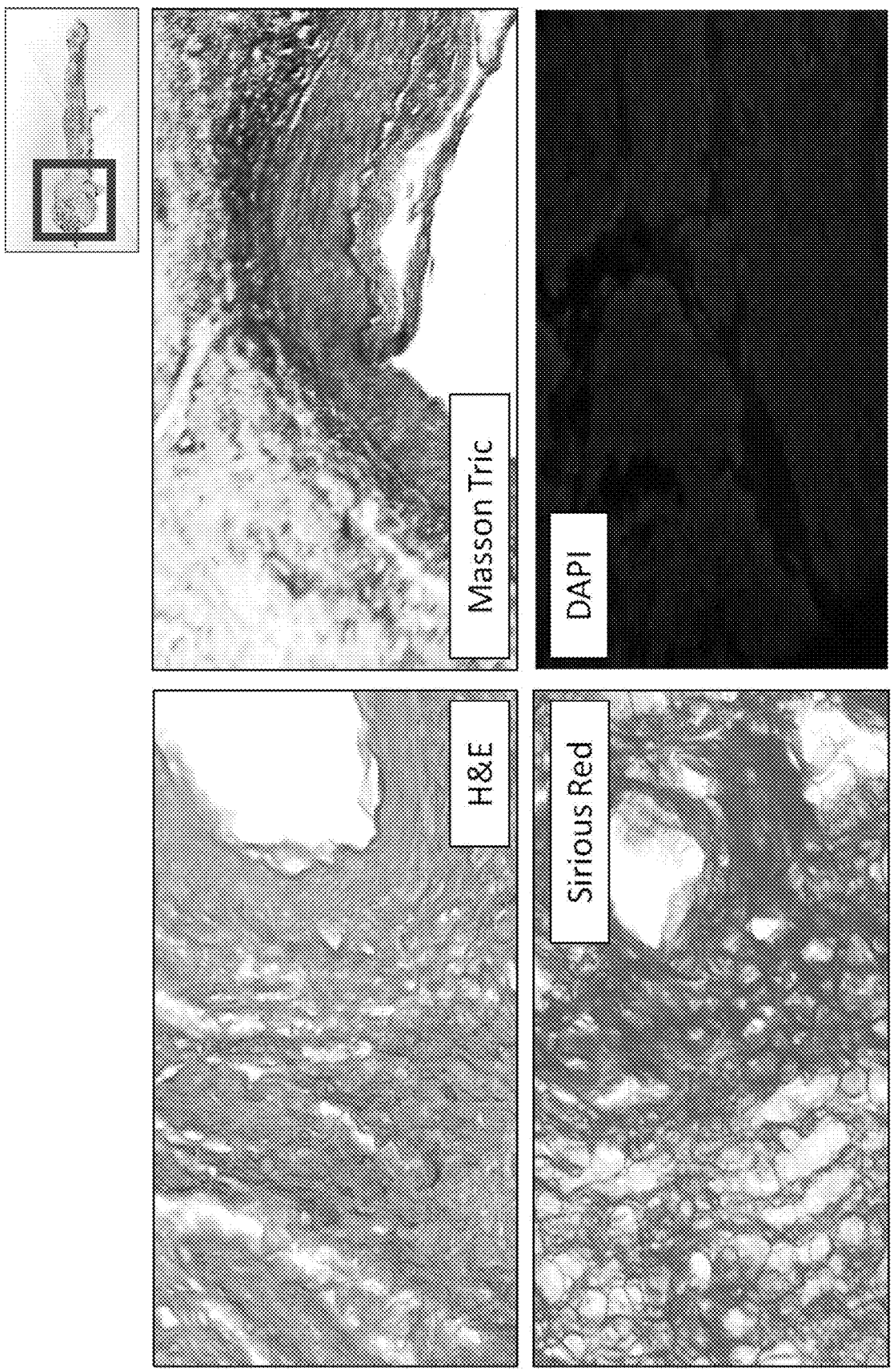
FIG. 13. Staining of the head of the post-decellularization pancreas with H&E, Masson Tric, Sirious Red and DAPI. All stains show the absence of cells.
Figure 14:
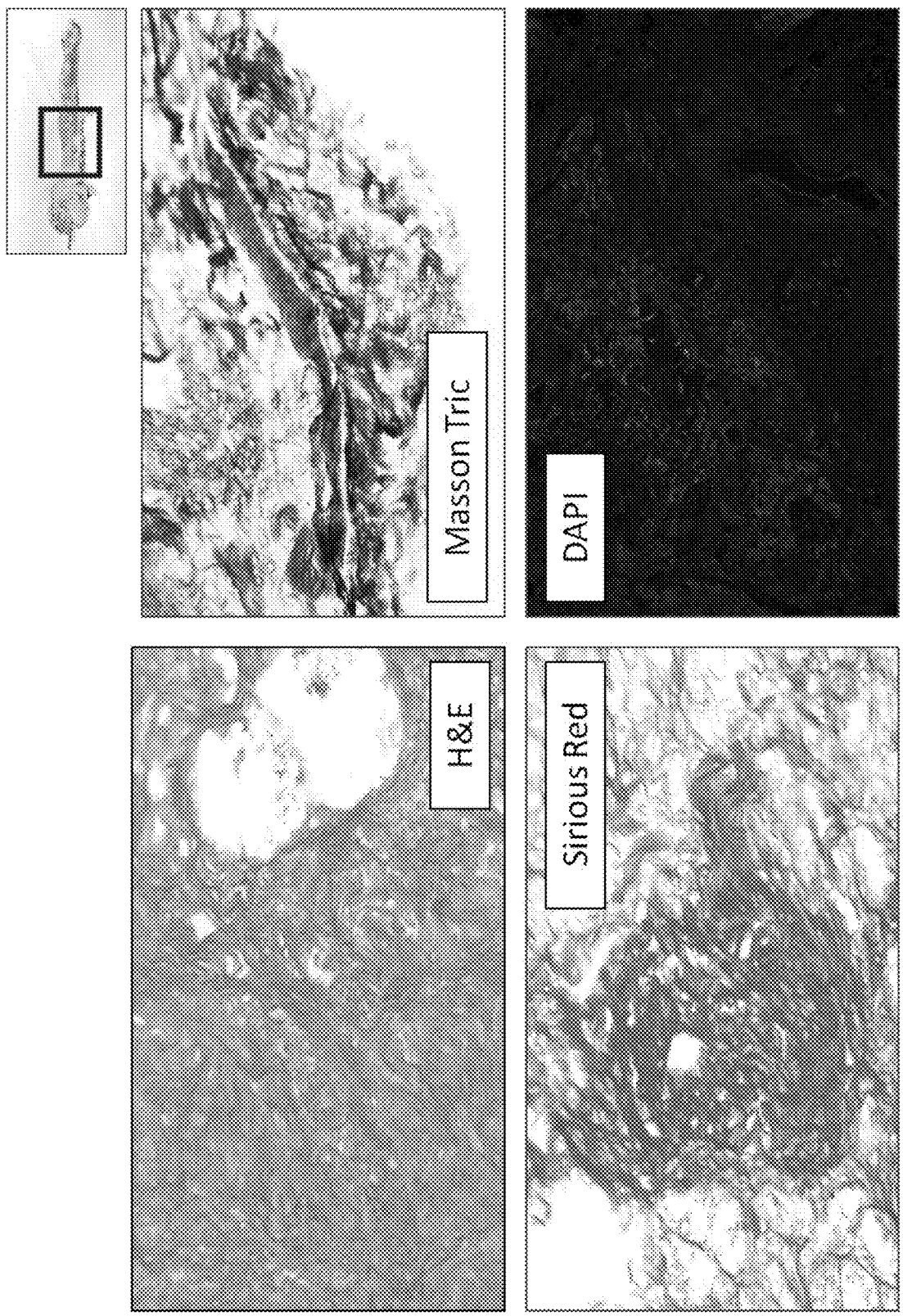
FIG. 14. Staining of the body of the post-decellularization pancreas with H&E, Masson Tric, Sirious Red and DAPI. All stains show the absence of cells.
Figure 15:
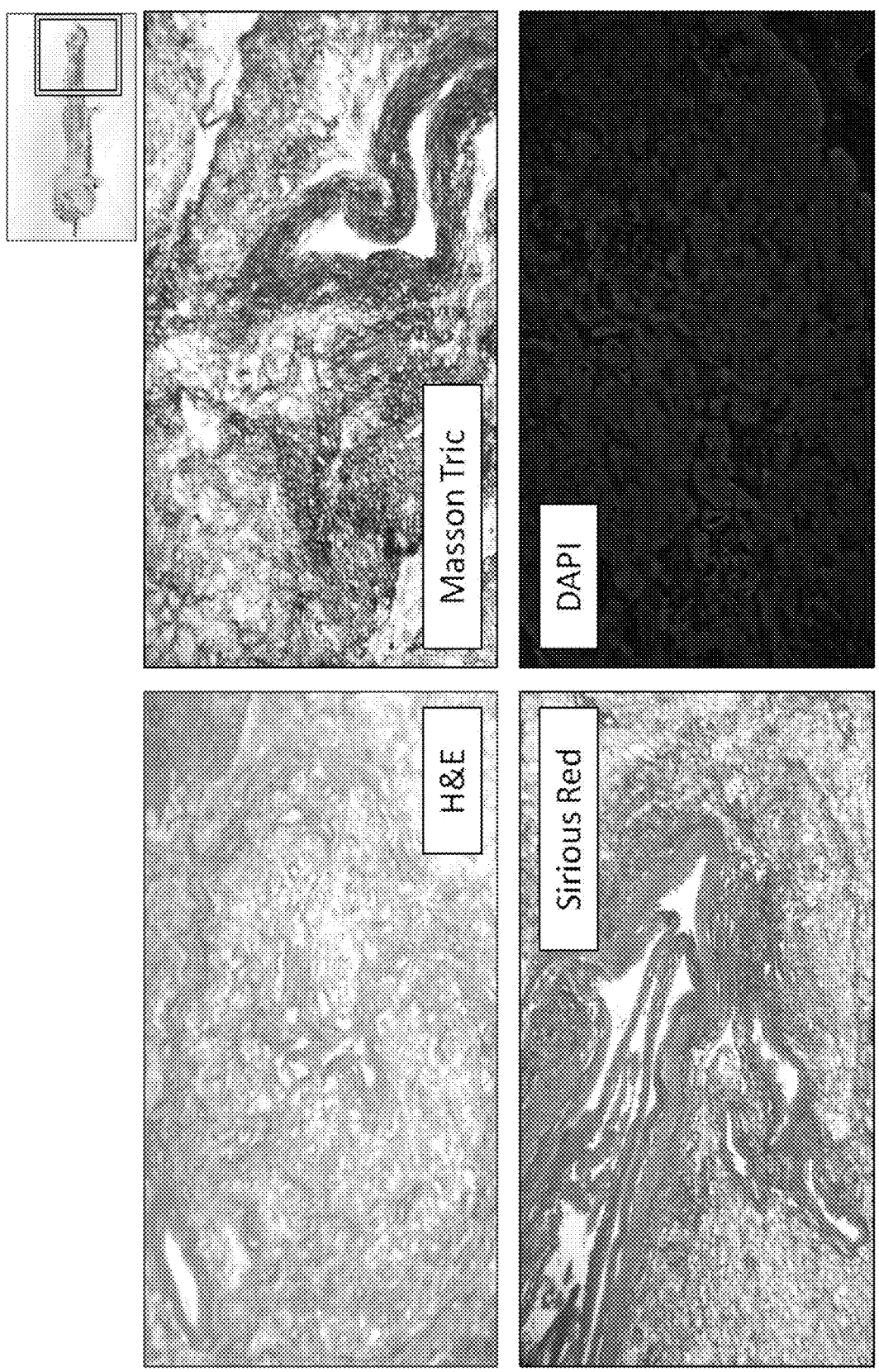
FIG. 15. Staining of the tail of the post-decellularization pancreas with H&E, Masson Tric, Sirious Red and DAPI. All stains show the absence of cells.
Figure 16:
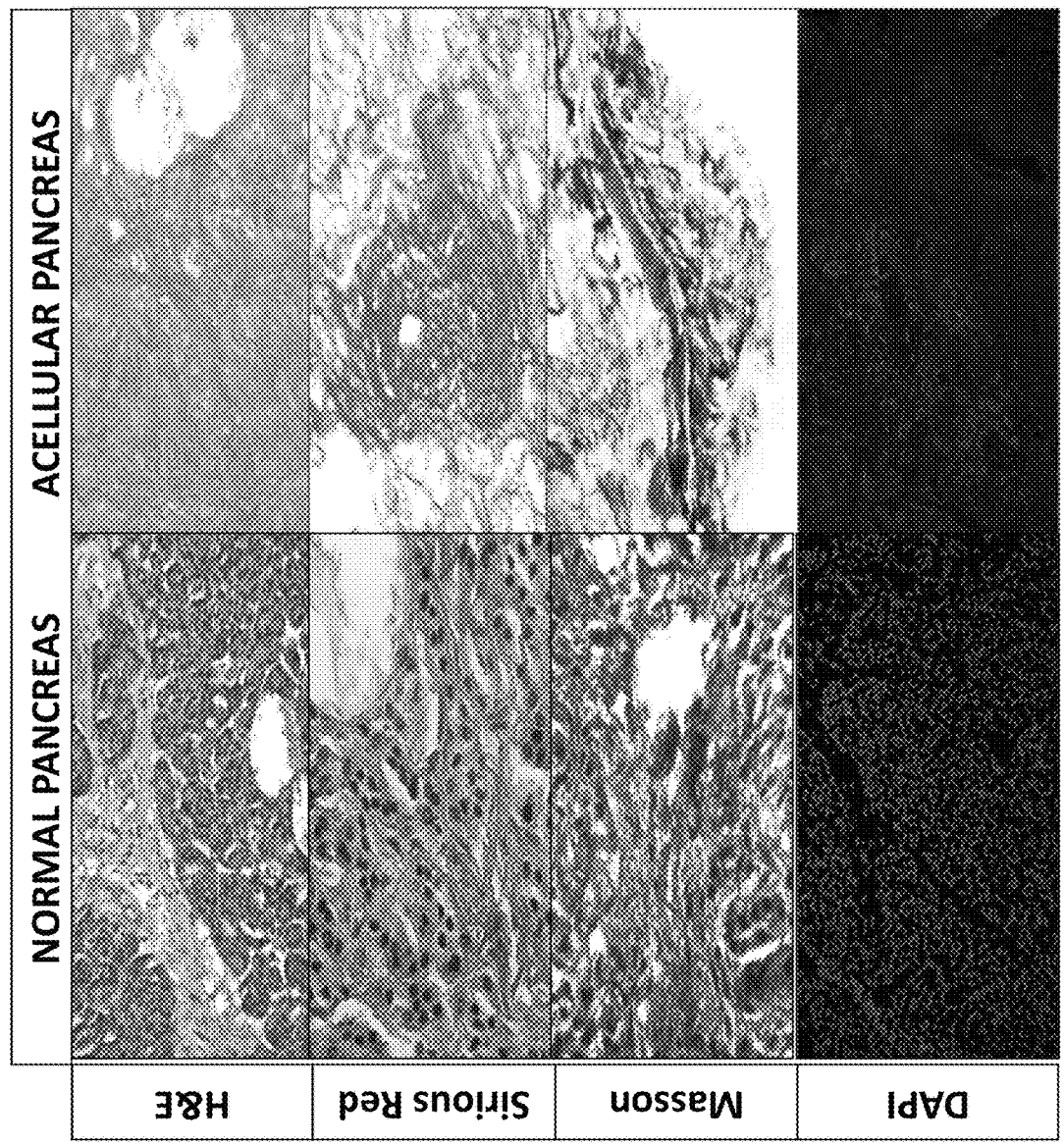
FIG. 16. Comparison between the normal pancreas prior to decellularization and the pancreas after decellularization, revealing the post-decellularization pancreas to be acellular.

The average renal artery pressure in native kidney ranged from about 32-44 mmHg at 10 ml/min and increased linearly to about 50-94 at mmHg at 30 ml/min ($R^2$=0.99) (FIG. 7). The pressures measured for the acellular renal ECM scaffolds ranged from about 10-195 mmHg at 10 ml/min and increased linearly to about 17-50 mmHg at 30 ml/min ($R^2$=0.91) (FIG. 7). One-way ANOVA determined that a statistically significant difference exists between native and acellular kidney artery pressure (p<0.05). Post-hoc analysis using Fisher's least significance difference (LSD) correction was conducted and determined that statistically significant differences ($p<0.05$) were observed between native and acellular kidney pressure at 20 ml/min, 25 ml/min, and 30 ml/min (FIG. 7). Although there was a large degree of variability in samples, possibly due the varying degree of vascular damage (arteriolo- and arterio-sclerosis, vascular hyalinosis) present in the renal grafts, the linear increase in pressures indicates good preservation of the vasculature in the renal ECM scaffolds, with patent and resilient vasculature.

REFERENCES—FOR EXAMPLES 1-8 ONLY

1. Orlando G, Wood K J, De Coppi P, Baptista P M, Binder K W, Bitar K N, et al. Regenerative medicine as applied to general surgery. Ann Surg 2012; 255:867-880.
2. Orlando G, Wood K J, Stratta R J, Yoo J, Atala A, Soker S. Regenerative medicine and organ transplantation: Past, present and future. Transplantation 2011; 91:1310-7.
3. Orlando G, Baptista P, Birchall M, Di Coppi P, Farney A, Opara E, et al. Regenerative medicine as applied to solid organ transplantation: current status and future development. Transpl Int 2011; 24:223-232.
4. Ross C L, Booth C, Sanders B, Bergman C, Soker T, Stratta R J, et al. Abdominal organ bioengineering: current status and future perspectives. Expert Opin Biol Ther 2013; 13:103-13
5. Badylak S F, Weiss D J, Caplan A, Macchiarini P. Engineered whole organs and complex tissues. Lancet 2012; 379:943-52.
6. Badylak S F, Taylor D, Uygun K. Whole-organ tissue engineering: decellularization and recellularization of three-dimensional matrix scaffolds. Annu Rev Biomed Eng 2011; 13:27-53.
7. Shupe T, Williams M, Brown A, Willenberg B, Petersen B E. Method for the decellularization of intact rat liver. Organogenesis 2010; 6:134-136.
8. Wang Y, Cui C B, Yamauchi M, Miguez P, Roach M, Malavarca R, et al. Lineage restriction of human hepatic stem cells to mature fates is made efficient by tissue-specific biomatrix scaffolds. Hepatology 2011; 53:293-305.
9. Baptista P M, Siddiqui M M, Lozier G, Rodriguez S R, Atala A, Soker S. The use of whole organ decellularization for the generation of a vascularized liver organoid. Hepatology 2011; 53:604-617.
10. Lang R, Stern M M, Smith L, Liu Y, Bharadwaj S, Liu G, et al. Three-dimensional culture of hepatocytes on porcine liver tissue-derived extracellular matrix. Biomaterials 2011; 32:7042-7052.
11. Hata T, Uemoto S, Fujimoto Y, Murakami T, Tateno C, Yoshizato K, et al. Transplantation of engineered chimeric liver with autologous hepatocytes and xenobiotic scaffold. Ann Surg 2013; 257:542-7.
12. Barakat O, Abbasi S, Rodriguez G, Rios J, Wood R P, Ozaki C, et al. Use of decellularized porcine liver for engineering humanized liver organ. J Surg Res 2012; 173:11-25.
13. Uygun B E, Soto-Gutierrez A, Yagi H, Izamis M L, Guzzardi M A, Shulman C, et al. Organ reengineering through development of a transplantable recellularized liver graft using decellularized liver matrix. Nat Med 2010; 16:814-820.
14. Zhou P, Lessa N, Estrada D C, Severson E B, Lingala S, Zern M A, et al. Decellularized liver matrix as a carrier for the transplantation of human fetal and primary hepatocytes in mice. Liver Transpl 2011; 17:418-427.
15. Ott H C, Matthiesen T S, Goh S K, Black L D, Kren S M, Netoff T I, et al. Perfusion-decellularized matrix: using nature's platform to engineer a bioartificial heart. Nat Med 2008; 14:213-21.
16. Ott H C, Clippinger B, Conrad C, Schuetz C, Pomerantseva I, Ikonomou L, et al. Regeneration and orthotopic transplantation of a bioartificial lung. Nat Med 2010; 16:927-33.
17. Petersen T H, Calle E A, Zhao L, Lee E J, Gui L, Raredon M B, et al. Tissue-engineered lungs for in vivo implantation. Science 2010; 329:538-41.
18. Nichols J E, Niles J A, Cortiella J. Production and utilization of acellular lung scaffolds in tissue engineering. J Cell Biochem 2012; 113:2185-92.
19. Bissell M J, Hall H G, Parry G. How does the extracellular matrix direct gene expression? *J Theor Biol* 1982; 99:31-68.
20. Chung S Y, Krivorov N P, Rausei V, Thomas L, Frantzen M, Landsittel D, et al. Bladder reconstitution with bone marrow derived stem cells seeded on small intestinal submucosa improves morphological and molecular composition. J Urol 2005; 174:353-9.
21. Ross E A, Williams M J, Hamazaki T, Terada N, Clapp W L, Adin C, et al. *Embryonic stem cells proliferate and differentiate when seeded into kidney scaffolds.* J Am Soc Nephrol 2009; 20:2338-47.
22. Ng S L, Narayanan K, Gao S, Wan A C. Lineage restricted progenitors for the repopulation of decellularized heart. Biomaterials 2011; 32:7571-80.
23. Cortiella J, Niles J, Cantu A, Brettler A, Pham A, Vargas G, et al. Influence of acellular natural lung matrix on murine embryonic stem cell differentiation and tissue formation. *Tissue Eng Part A* 2010; 16:2565-80.
24. Song J J, Guyette J P, Gilpin S E, Gonzalez G, Vacanti J P, Ott H C. Regeneration and experimental orthotopic transplantation of a bioengineered kidney. Nature Medicine 2013 [Epub ahead of print] doi:10.1038/nm.3154.
25. Orlando G, Farney A, Sullivan D C, AbouShwareb T, Iskandar S, Wood K J, et al. Production and implantation of renal extracellular matrix scaffolds from porcine kidneys as a platform for renal bioengineering investigations. Ann Surg 2012; 256:363-70.
26. Vodicka P, Smetana K Jr, Dvoránková B, Emerick T, Xu Y Z, Ourednik J, et al. The miniature pig as an animal model in biomedical research. Ann NY Acad Sci 2005; 1049:161-71.
27. Matas A J, Smith J M, Skeans M A, Lamb K E, Gustafson S K, Samana C J, et al. OPTN/SRTR 2011 Annual Data Report: kidney. Am J Transplant 2013; 13 (Suppl 1):11-46.
28. Baiguera S, Macchiarini P, Ribatti D. Chorioallantoic membrane for in vivo investigation of tissue-engineered construct biocompatibility. *J Biomed Mater Res B Appl Biomater* 2012; 100:1425-34.
29. Totonelli G, Maghsoudlou P, Garriboli M, Riegler J, Orlando G, Burns A, et al. Production and characterization of a rat decellularized small bowel scaffold that preserves villus-crypt architecture. Biomaterials 2012; 33:3401-10.
30. Miner J H. *The glomerular basement membrane.* Exp Cell Res 2012; 318:973-8.
31. Spenlé C, Simon-Assmann P, Orend G, Miner J H. *Laminin α5 guides tissue patterning and organogenesis.* Cell Adh Migr. Oct. 17, 2012; 7(1). [Epub ahead of print].

32. Bach F H. Genetics of transplantation: the major histocompatibility complex. *Annu Rev Genet.* 1976; 10:319-39.
33. Lin S, Li D, Jia J, Zheng Z, Jia Z, Shang W. Spironolactone ameliorates podocytic adhesive capacity via restoring integrin alpha 3 expression in streptozotocin-induced diabetic rats. J Renin Angiotensin Aldosterone Syst. 2010; 11:149-157.
34. Pozzi A, Jarad G, Moeckel G W, Coffa S, Zhang X, Gewin L, et al. Beta1 integrin expression by podocytes is required to maintain glomerular structural integrity. Dev Biol. 2008; 316:288-301.
35. Kanasaki K, Kanda Y, Palmsten K, Tanjore H, Lee S B, Lebleu V S, et al. Integrin beta1-mediated matrix assembly and signaling are critical for the normal development and function of the kidney glomerulus. Dev Biol. 2008; 313:584-593.
36. Groffen A J, Ruegg M A, Dijkman H, van de Velden T J, Buskens C A, van den Born J, et al. Agrin is a major heparan sulfate proteoglycan in the human glomerular basement membrane. J Histochem Cytochem 1998; 46:19-27.
37. Remuzzi A, Gagliardini E, Sangalli F, Bonomelli M, Piccinelli M, Benigni A, et al. ACE inhibition reduces glomerulosclerosis and regenerates glomerular tissue in a model of progressive renal disease. *Kidney Int* 2006; 69:1124-30.
38. Remuzzi G, Benigni A, Remuzzi A. Mechanisms of progression and regression of renal lesions of chronic nephropathies and diabetes. J Clin Invest 2006; 116:288-96.
39. Hammel P, Couvelard A, O'Toole D, Ratouis A, Sauvanet A, Fléjou J F, et al. *Regression of liver fibrosis after biliary drainage in patients with chronic pancreatitis and stenosis of the common bile duct.* N Engl J Med 2001; 344:418-23.
40. Marcellin P, Gane E, Buti M, Afdhal N, Sievert W, Jacobson I M, et al. Regression of cirrhosis during treatment with tenofovir disoproxil fumarate for chronic hepatitis B: a 5-year open-label follow-up study. *Lancet* 2013; 381:468-75.

The data presented in Examples 1-8 show that discarded human kidneys can be successfully decellularized with the resulting renal ECM scaffolds maintaining (a) their three-dimensional architecture at the macro and micro levels, (b) vascular patency and (c) biological function. From a clinical transplant perspective, the possibility of utilizing discarded human kidneys as source of organs gives hope to the myriad of patients who are currently waiting for a new kidney and have to face longer waiting times because of the increasing disparity between supply and demand. The catastrophic consequence represented by the increase in waiting list mortality is fueling efforts to meet the urgent need to identify new organ sources. Organ bioengineering and regeneration holds the promise to meet this need and justifies investments and efforts in this direction.

EXAMPLE 9

Whole Organ Engineering—Antibody Conjugation to Re-Endothelialize Kidney Scaffolds Consistent with observations made above, end-stage renal disease (ESRD) is a major problem in the United States and around the world. According to a report by the National Kidney &Urologic Diseases Information Clearinghouse (2009), more than 870,000 people in the United States were undergoing treatment for ESRD. Current treatments are limited to life-long dialysis and/or renal transplantation. While dialysis can replace the filtration function of the kidneys by removing certain toxins from the patient's blood, it cannot replace many of the other functions of the kidneys, such as production of erythropoietin and vitamin D; resulting in complications such as anemia, malnutrition, and eventually requires kidney transplantation. Therefore, kidney transplantation is currently the only definitive solution for the treatment of ESRD. However, due to a critical shortage of available donor kidneys, physicians and scientists have sought for novel solutions to this problem.

Whole organ engineering techniques based on decellularization of organs and recellularization of the resulting collagen-based matrix would provide an effectively inexhaustible supply of organs to replace those suffering from disease or injury. The first step of this technique is the "decellularization" of native organs. During the decellularization process, primary immunogenic factors such as cellular proteins and DNA components are removed from the organ so that foreign body responses can be reduced after transplantation. Decellularization methods are typically based on perfusion of the organ through existing vascular systems with detergents and other agents. These perfusion-based decellularization protocols allow efficient removal of all native cells and residual DNA, while maintaining the structural integrity of the organ's extracellular matrix. Subsequently, the resulting acellular matrix needs to be repopulated with functional organ-specific cell populations ("recellularization"). Available cell sources for target-specific organs can be seeded onto the decellularized matrix and allowed to organize into functional components of the organ. Ideally, engineered whole organs should contain an intact three-dimensional cellular architecture as well as functional vasculature that is composed of appropriate cell types to achieve organ function after transplantation.

Figure 23:
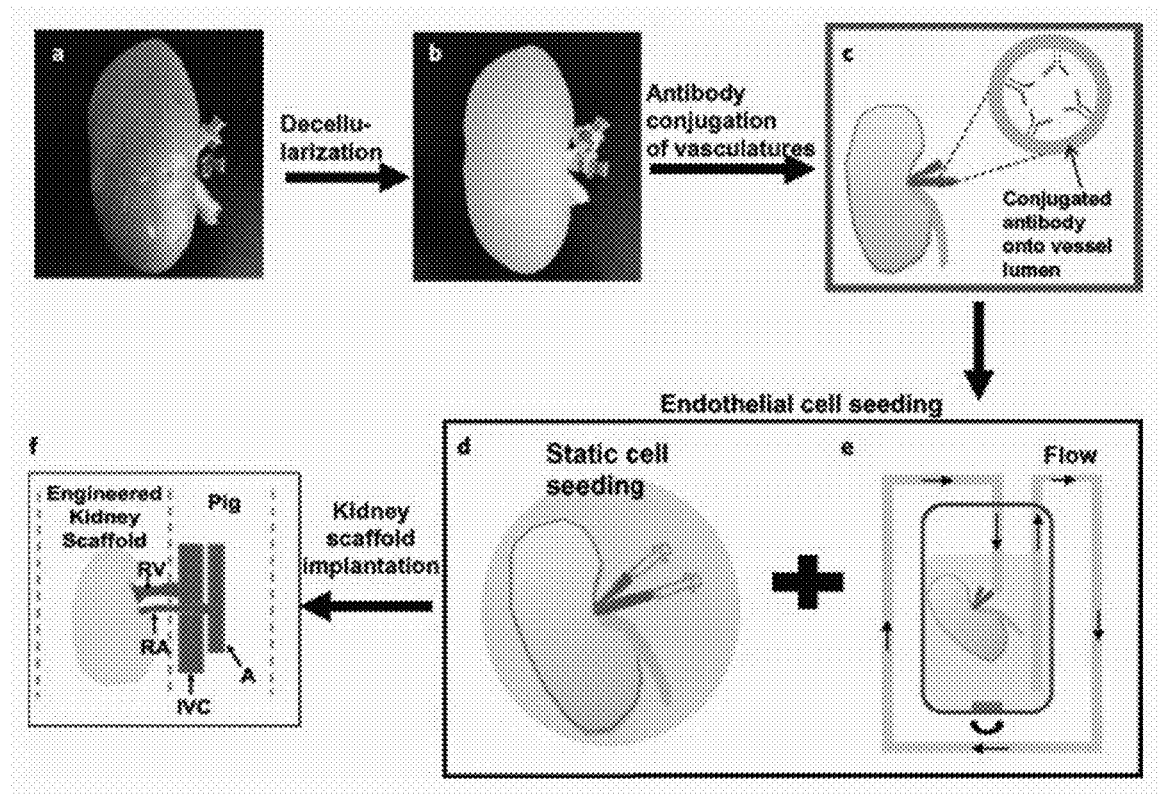
FIG. 23. Schematic diagram of the overall re-endothelialization processes in the decellularized pig kidney scaffold and in vivo implantation. Native kidney (a) was decellularized using 0.5% SDS and DNAase treatment to obtain a completely decellularized kidney scaffold (b). Following antibody conjugation on vasculatures of the kidney scaffold (c), the antibody-conjugated scaffold was then seeded with endothelial cells (MS1) using a combination of the static (d) and ramping perfusion methods (e), and then cultured in a bioreactor system. For in vivo function evaluation, the implantation of re-endothelialized kidney scaffold was performed by arterial [renal artery (RA) with aorta (A)] and venous [renal vein (RV) with inferior vena cava (IVC)] anastomosis into pigs (f). RA and RV are indicated by red and blue suture material, respectively.

The field of whole-organ tissue engineering is still in its infancy. One major challenge for long-term in vivo success of bioengineered organs is vascular patency. In the absence of complete endothelial reseeding of vascular matrices, significant thrombosis is likely to occur within the vasculature of the scaffold, thus rendering the recellularized construct nonfunctional. To address this issue, we have developed an endothelial cell-seeding method that permits effective endothelial cell coating of the vascular walls of decellularized porcine kidney scaffolds. Acellular renal matrices were processed from normal pig kidneys using a decellularization technique incorporated herein by reference[13]. Several endothelial cell-seeding methods were tested that have been described in other studies[2,4,5,8]. Through optimization of these cell-seeding protocols, a combined cell-seeding method was developed for acellular kidney scaffolds that is composed of static and ramping perfusion seeding. The efficiency of re-endothelialization on the blood vessels in the kidney scaffold was determined by histological characterization and imaging studies of the re-endothelialized vascular tree, as well as in vitro functionality being tested by blood perfusion. In addition, a surface modification method was developed to reinforce endothelial cell attachment onto renal vasculatures via CD31 antibody conjugation. The effectiveness of antibody conjugation to mediate re-endothelialization in vivo was evaluated through implantation (FIG. 23).

Decellularization of porcine kidney and endothelial cell seeding of acellular kidney scaffolds Decellularization of porcine kidney was processed using a high-throughput system as described[13], and that description is incorporated herein by reference. In brief, whole kidneys were perfused with heparin and then 0.5% sodium dodecyl sulfate (SDS) in phosphate-buffered saline (PBS) for 36 hours, followed by a rinse with PBS, enzymatic treatment with 0.0025% DNase (Sigma-Aldrich, St. Louis, Mo.) for 12 hours, followed by another rinse with PBS. Subsequently, decellularized kidneys were sterilized via gamma irradiation at 1 MRad (10,000 Gy) prior to cell seeding. Vascular endothelial cells expressing GFP protein (MS1) were used in this study[5]. Four experimental groups were tested in order to find an optimal cell seeding condition. These include (1) perfusion cell seeding ($100\times10^6$) at a constant rate of 20 ml/min (n=2), (2) static cell seeding ($50\times10^6$) followed by constant perfusion seeding ($50\times10^6$) at 20 ml/min (n=1), (3) ramping perfusion cell seeding ($100\times10^6$) (n=2), and (4) static cell seeding ($50\times10^6$) followed by ramping perfusion ($50\times10^6$) (n=3). For static cell seeding, 5 ml of $10\times10^6$/ml MS1 cells suspended in DMEM-high glucose medium (Invitrogen Life Technologies, Carlsbad, Calif.) supplemented with 10% FBS (Invitrogen Life Technologies) was infused into the renal artery (2.5 ml) and vein (2.5 ml) simultaneously. The seeded cells were then allowed to attach for 2 hours, followed by another 2 hours after a 180-degree angle rotation of the kidney scaffold from the original position to allow for homogenous attachment of the cells in an incubator at 37° C., supplemented with 5% $CO_2$. Following the static seeding, the kidney scaffold was connected to a bioreactor system and then perfused at 2 ml/min with 10% FBS DMEM medium until ramping perfusion seeding began. The ramping perfusion was initiated at a rate of 2 ml/min and gradually increased to 5, 10, and 20 ml/min at 10-12 hour intervals, and maintained at 20 ml/min. All kidney scaffolds received a total of approximately $100\times10^6$ cells and were cultured for 3 days in the bioreactors prior to analysis. For the constant perfusion seeding, $100\times10^6$ MS1 cells were suspended in the bioreactor medium, and the scaffold was continuously perfused at a constant flow rate of 20 ml/min. Almost all of the seeded cells were retained within the scaffold. This was confirmed by examining the returned perfusate in the bioreactor container. Only a few cells were visible under a 10× microscope. After bioreactor perfusion culture, the MS1-seeded scaffold was fixed in 10% formalin, embedded in OCT compound, and processed for histological analysis (H&E and DAPI nuclear staining).

Characterization of Re-Endothelialization on Kidney Scaffold

Seeding efficiency was determined by histomorphometric analysis using H&E stained images of the re-endothelialized vessels of different sizes (large for renal artery and vein, intermediate, small) within the scaffold. The number of blood vessels that had been re-endothelialized (greater than 50% coverage in each vessel) and/or filled with MS1 cells (greater than 50% occupancy of vessel spaces) were counted and scored for analysis (Table 1).

TABLE 1

| Cell adhesion | Constant perfusion | Static + constant perfusion | Ramping perfusion | Static + ramping perfusion |
|---|---|---|---|---|
| Artery and vein | + | + | + | +++ |
| Immediate-sized blood vessels | + | + | ++ | +++ |
| Small-sized blood vessels in cortex | + | + | ++ | +++ |
| Cell Clogging | ++ | +++ | + | + |

Criteria for scoring: 0-30% (+), 31-60% (++), 61-100% (+++).

Vessel size greater than 100 μm was considered as intermediate, and less than 100 μm as small. Re-endothelialized renal artery and vein were observed under scanning electron microscopy (SEM; ModelS-2260N, Hitachi Co. Ltd., Japan). Briefly, the sample was sputter-coated with gold (Hummer™ 6.2, Anatech Ltd, Denver, N.C., USA) to a thickness of 10-15 nm. Images were acquired using an environmental SEM operating at an accelerating voltage of 20 kV with a 10 cm working distance. For re-endothelialized vascular tree imaging, formalin-fixed blood vessel branches were isolated and visualized with a fluorescent stereomicroscope (Leica, Germany) equipped with a GFP protein detection filter.

In vitro Functional Testing

To determine the functionality of re-endothelialized kidney vasculature, seeded scaffolds were perfused with freshly collected heparinized pig blood for 30 minutes up to 100 ml/min of flow rate. To more closely represent an in vivo environment following implantation, the perfusion rate was increased up to 100 ml/min, which is the maximum rate the pump can generate. The blood perfusate was prepared by diluting whole blood with 3:1 ratio in Kreb's bicarbonate buffer. Unseeded scaffolds were used as controls. To determine platelet adhesion on the scaffolds, frozen sections were stained with an anti-integrin αIIb antibody (SantaCruz Biotechnology Inc., Santa Cruz, Calif.) and Alexa 647-conjugated rabbit anti-goat antibody (Invitrogen Life Technologies). Images were visualized with an inverted microscope (Nikon Eclipse TE 2000-U) with an argon laser confocal microscope system (Laser Drive Inc, Gibsonia, Pa.) facilitated with MAG Biosystems software. The numbers of stained platelets were counted in 3 randomly selected images from different sized vessels. The counts were averaged, and then represented as mean±SD.

Cell Detachment Study Under Flow Conditions

A polydimethylsiloxane (PDMS)-based microfluidic device was constructed to conduct cell detachment study under shear flow. The molded portion of flow chamber was made from Sylgard 184 silicone elastomer kit (Dow Corning, Midland, Mich.) according to manufacturer's instructions. After preparation of the chamber, 20 G needles were inserted into the inlet and outlet and tubing was used for connecting the inlet to syringes. The interior surface of the chamber was coated with type I collagen (Elastin Products Co. Inc., Owensville, Mo.) by filling the chamber with a 0.05% collagen solution dissolved in 1,1,1,3,3,3-hexafluoro-2-propanol (HFIP, Sigma). Rat anti-mouse CD31 antibody (BD sciences, Franklin Lakes, N.J.) was conjugated to the collagen-coated chamber by filling the chamber with a solution of 1-Ethyl-3-[3-dimethylaminopropyl]carbodiimide hydrochloride (EDC) (Sigma-Aldrich) and N-hydroxysuccinimide esters (NHS) (Sigma-Aldrich) in PBS buffer for 30 minutes, followed by reacting with a 100 μg/mL antibody solution for 2 hours. Control chambers were coated with collagen, crosslinked with DC/NHS, and then treated with PBS for 2 hours. Collagen coating and CD31 antibody conjugation on the surfaces of chamber slides was confirmed with coomassie blue staining and treatment with Alexa588 goat anti-rat antibody, respectively. The conjugated antibody was semi-quantified by imaging with a fluorescent microscope and measuring the fluorescent intensity using Image J software. To examine the efficacy of antibody conjugation on reducing cell detachment from the surfaces, the flow chamber experiment under dynamic flow conditions (2 to 100 ml/hour) was performed. For the cell detachment study, MS1 cells were allowed to pre-adhere on the surfaces by placing the cell suspension solution ($10^5$ cells/mL) at static conditions for 10 minutes before starting flow through the chamber. A duration of 10 minutes was chosen for this experiment, based on previous studies on cell adherence and detachment[14]. A syringe pump was used to flow 3% w/v BSA/media through the chamber at a rate of 2 mL/hour for 10 minutes to remove non-adherent cells. The flow rate of media through the chamber was increased sequentially to 10, 20, 50, and 100 mL/hour with each flow rate run for 3 minutes. Continuous video of the cells was obtained during the flow. The number of cells on the surface was counted after exposure to each flow condition. All values were normalized to the number of cells after 2 mL/hour flow. Cell numbers were counted using Image J software, averaged, and represented as mean±SEM.

Bioreactor Culture

Perfusion bioreactors were designed and constructed specifically for porcine kidneys, and consisted of a glass chamber for the kidney, with media circulation via platinum-cured silicone tubing (Cole-Parmer, L/S 15) and a pulse dampener to maintain constant flow using Cole-Parmer Digital Drive peristaltic pumps. Bioreactors contained 2 L of growth medium (DMEM-high glucose with 10% fetal bovine serum, 1% antibiotic/antimycotic supplement) for each cell-seeding method and were maintained in humidified conditions at 37° C., supplemented with 5% $CO_2$. Media was perfused directly into the kidney via the renal artery and, during the culture, media was constantly stirred via a magnetic stirrer.

In vivo Implantation Study

Yorkshire pigs (female, 40-50 kg, 3-6 months) were used for the in vivo animal study. All surgical procedures were performed in accordance with the Institutional Animal Care and Use Committee (IACUC) approved protocols. The animals received two different groups of implantation: (1) 2 hours (re-endothelialized kidney without antibody conjugation, n=3 animals) and (2) 4 hours implantation (re-endothelialized kidney with CD31 antibody conjugation, n=3 animals). To prepare MS1-seeded kidney with antibody conjugation, CD31 antibody was conjugated to native collagen present in the decellularized kidneys[13] using the same reaction protocol used for the flow-chamber study. MS1 cell seeding on the antibody-conjugated scaffold was performed as described above (endothelial cell seeding method). The implantation protocol was similar to that developed in our previous study[5]. Briefly, animals were placed in a supine position, the surgical site was disinfected, and an intravenous catheter was placed to allow for proper fluid replacement and drug delivery during surgery, while monitoring cardiopulmonary function. Under general anesthesia, a midline abdominal incision was made through the skin and muscle. The abdominal aorta and inferior vena cava just above the iliac bifurcation were identified and dissected from the surrounding tissue. After placing a large Satinsky clamp on the recipient's inferior vena cava and aorta, the artery and vein of the kidney scaffold were anastomosed to the aorta and inferior vena cava in an end-to-side fashion using double-armed 6/0 prolene sutures. After reperfusion, the blood flow through the artery and vein of the implanted scaffold was monitored with Color Doppler ultrasonography (Acuson Sequola 512, Simens).

Characterization of the Harvested Kidney

At 2 and 4 hours after implantation, patency of vascular tree in the harvested kidney scaffold from the euthanized animals was examined by radiographic fluoroscopy using a Siemens SIREMOBIL CompactL C-arm (Siemens, Munich, Bavaria, Germany). Conray (iothalamatemeglumine) (Mallinckrodt Inc., St Louis, Mo.) contrast agent was injected through the renal artery, followed by histological (H&E staining) and immunohistochemical (platelet immunostaining) examination. To obtain percentage of endothelialization by MS1 cells on the vasculatures, three different images of medulla and cortical regions were taken (H&E and GFP). GFP+MS1-endothelialization was based on the criteria (greater than 50% coverage in each vessel with less than 50% occupancy of vessel spaces). For quantification of platelet adhesion, αIIb+platelet fluorescent intensity was obtained from randomly selected images from medulla (three sites) and cortex (nine sites). Fluorescence intensity was calculated from the values [equal to (total fluorescence intensity/area)] of each fluorescence image using Image J software. The data was represented as mean±SD.

Statistics

Two-way ANOVA statistical analysis and the Bonferonni post hoc test were used for the flow chamber experiments. Student t-test analysis was used for other statistical analyses. Differences were considered significant at $P<0.05$.

Figure 17:
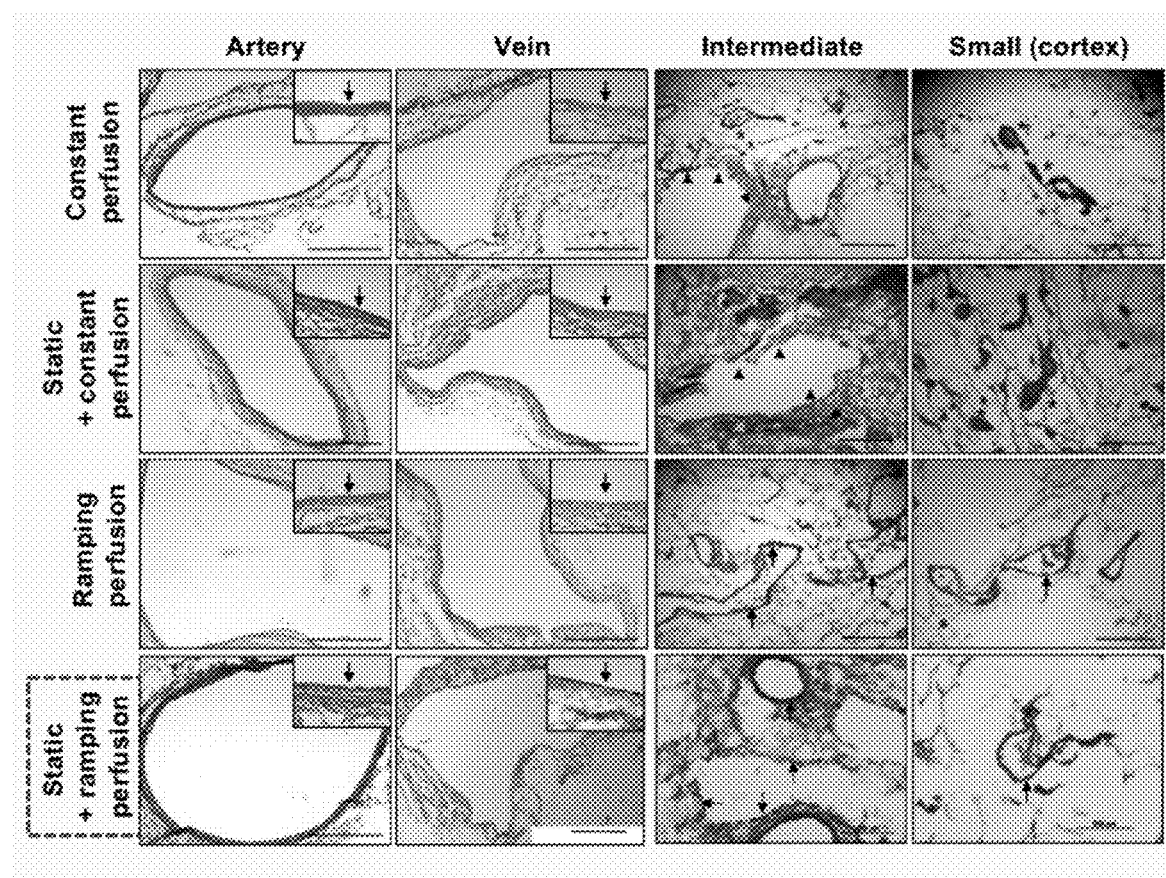
FIG. 17. Various cell seeding methods for re-endothelialization of acellular kidney scaffold. H&E stained images demonstrate that combination of static and ramping perfusion is the most effective method to facilitate cell lining of the renal artery and vein (arrows) and the intermediate- and small-sized blood vessels (arrows) in the parenchyma without cell clogging [(Small (cortex)]. The other three methods resulted in low cell attachment on the different-sized blood vessels (arrowheads), with severe cell clogging (asterisk) in the cortex. Scale bars indicate 1 mm (artery and vein), 50 μm (magnified box of artery/vein), and 200 μm (intermediate and small).
Figure 18:
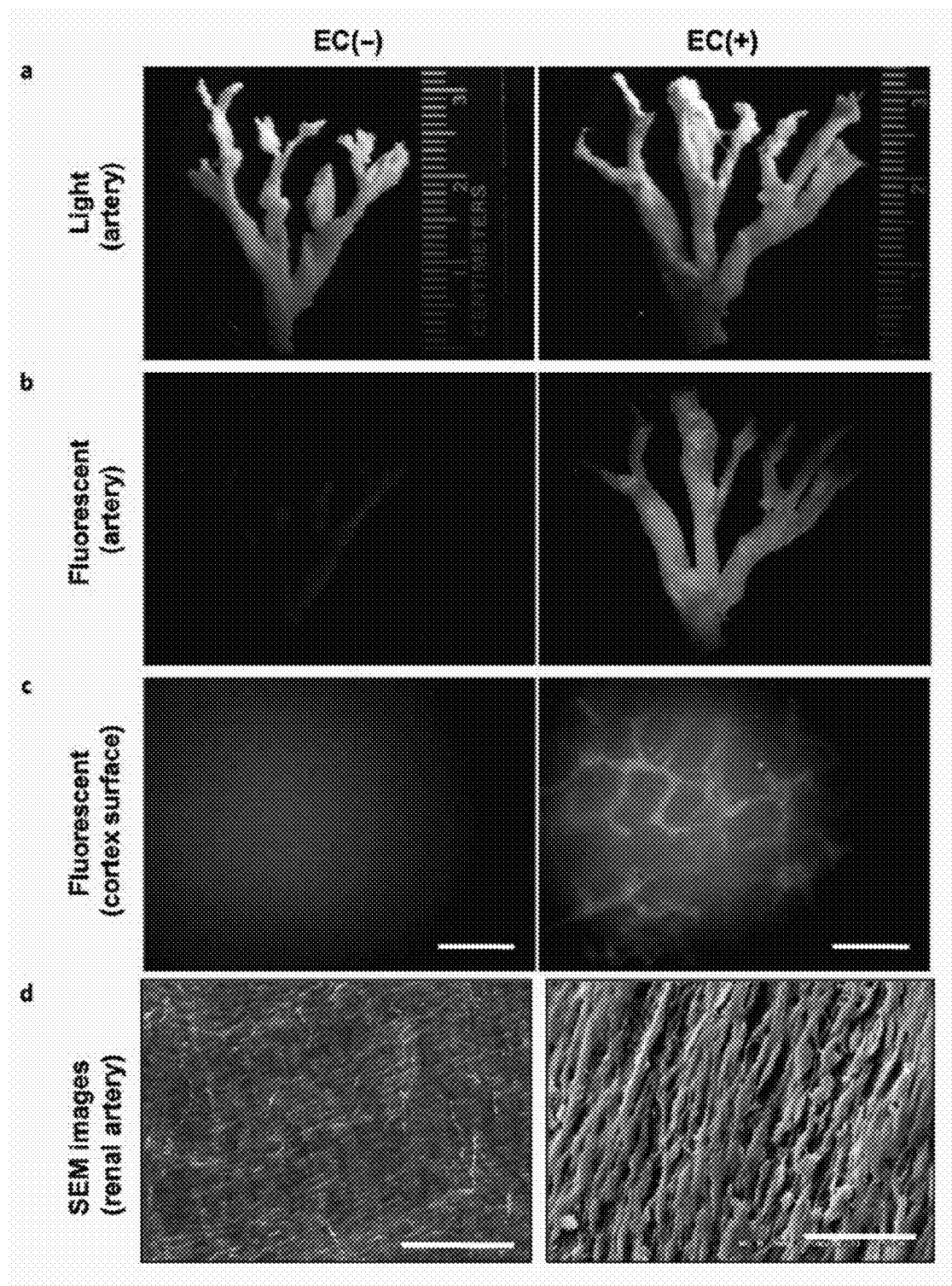
FIG. 18. Imaging of the re-endothelialized vascular tree. Light microscopic images (a) show intact arterial branches in unseeded [EC(−)] and seeded kidney scaffold [EC(+)]. The green fluorescent image derived from re-endothelialization was clearly visualized in [EC(+)] kidney scaffolds, whereas there is no strong GFP signal in the [EC(−)] scaffolds (b). Fluorescent imaging of cortical surfaces (c) indicates GFP-positive capillary-like structures in the [EC(+)] kidney scaffolds, indicating that viable MS1 cells are present in the cortical parenchyma. The SEM study indicates that the morphology of the endothelial cells is preserved on the inner surface of artery (d). Scale bars: 200 μm (c) and 50 μm (d).
Figure 24:
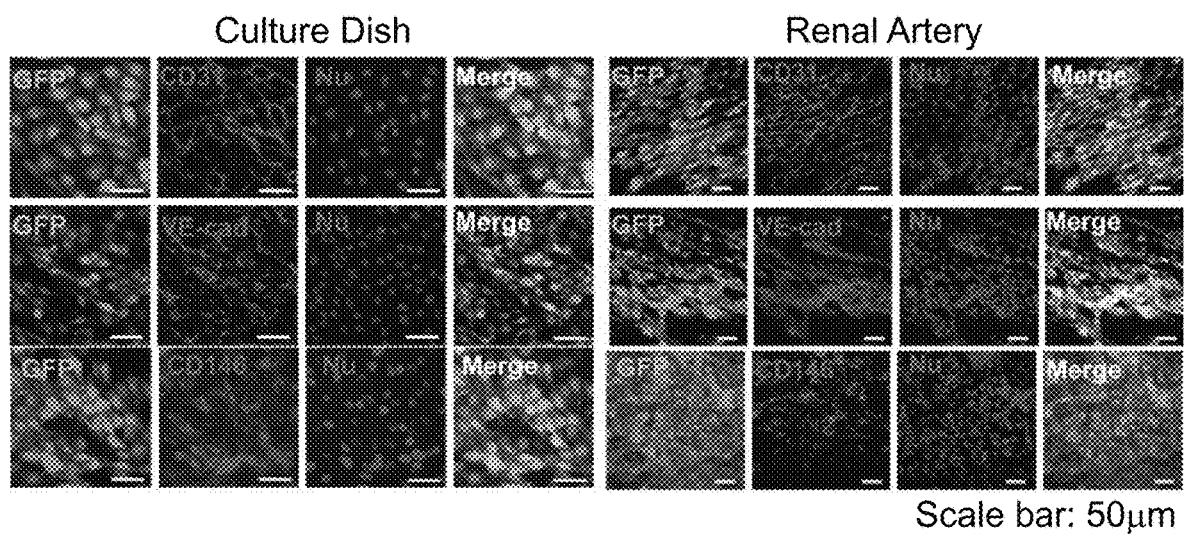
FIG. 24. Characterization of endothelial specificity by immunostaining using endothelial cell markers to determine phenotypic maintenance of MS1 cells. Endothelial cell markers such as CD31, vascular endothelial cadherin (VE-cad), and CD146 were used for the immunostaining. No phenotypic change was detected. Scale bars: 50 μm.
Figure 25:
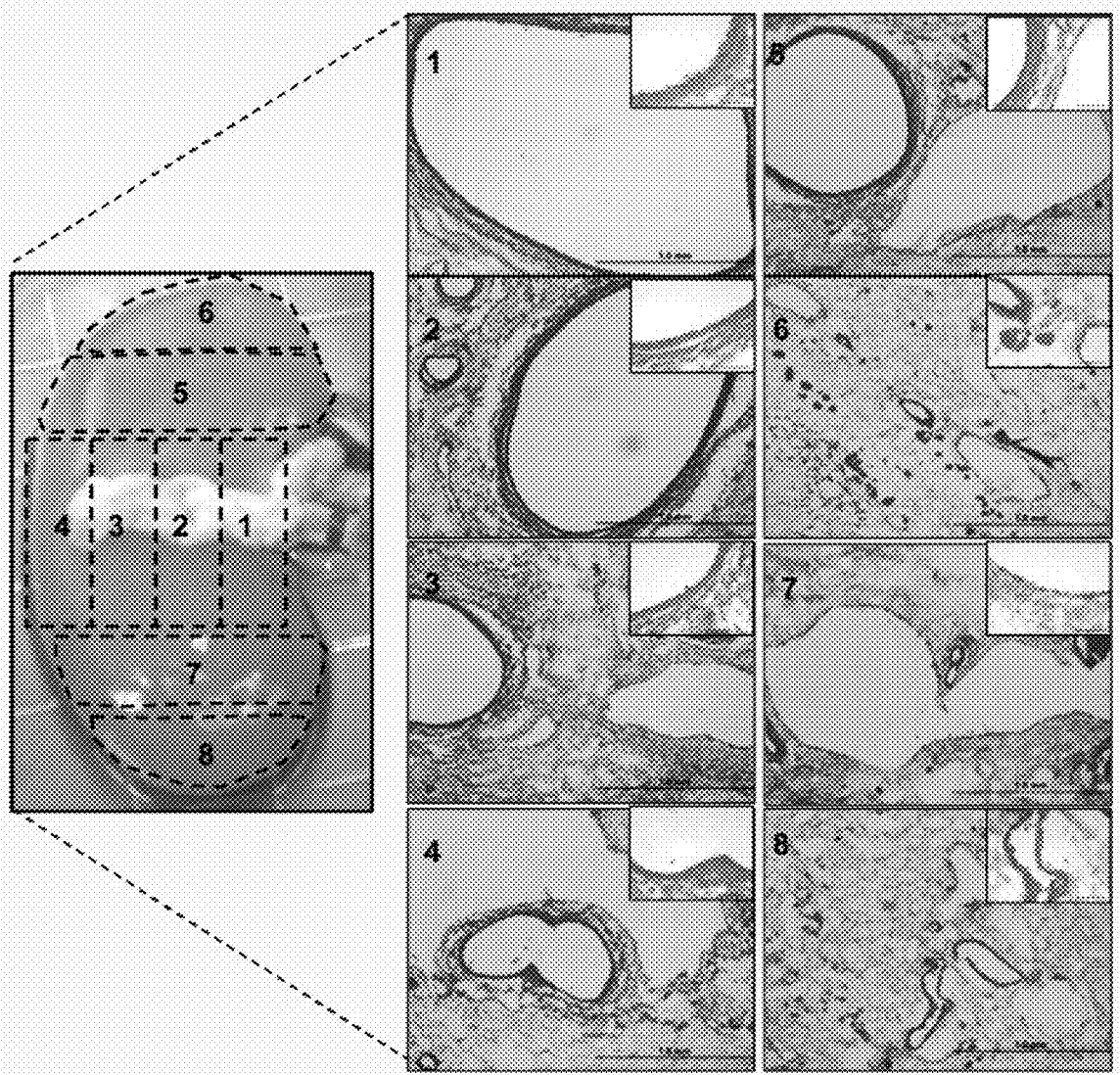
FIG. 25. H&E histology of different-sized blood vessels in the renal parenchyma. The H&E staining demonstrates that the size of the blood vessels decreased from segment 1 (closed renal artery and vein) to segment 4 (mid-pole cortex) and most blood vessels were lined with seeded MS1 cells as shown in the magnified images. Particularly, small-sized vessels showed patency in segment 6 (superior pole) and 8 (inferior pole) of the cortex. Scale bars: 50 μm (magnified boxes).

Development of an Effective Cell Seeding Method: Combining Static and Ramping Perfusion Cell Seeding The first series of experiments were designed to identify and optimize an efficient technique for the successful cell seeding and re-endothelialization of the blood vessels using the MS1 endothelial cell line within an acellular kidney scaffold. A flow rate of 20 ml/min was selected as the maximum perfusion rate, based on our previous cell-seeding experiments. Perfusion beyond this rate showed failure of cell attachment in the scaffold vessels. For ramping perfusion cell seeding, cell suspension was perfused through the kidney vasculature at a rate of 2 ml/min, and gradually increased up to 20 ml/min. Gradual increase in flow rate was employed to prevent cell clogging within the small capillary structures. Among the cell seeding methods tested, including constant perfusion, static+constant perfusion and ramping perfusion, the combination protocol of static and ramping perfusion was shown to be the most effective method (FIG. 17 and Table 1) and, thus, this method of seeding was used for all other experiments in this study. We examined whether seeding of MS1 cells using the combined static and ramping perfusion provides a homogenous distribution and functional alignment of the MS1 cells within the vasculature of the kidney scaffold. Following cell seeding, a vascular tree branching from the renal artery was isolated from the kidney parenchyma (FIG. 18a) and visualized with a fluorescent stereo-microscope in order to detect GFP-expressing MS1 cells (FIG. 18b). The MS1-seeded vascular tree structure [EC(+)] showed an increase in GFP-derived fluorescent intensity compared to the unseeded matrix [EC(−)] (FIG. 18b). Immunohistochemistry using CD31, vascular endothelial cadherin (VE-cad), and CD146 antibodies confirmed that the attached MS1 cells maintained endothelial phenotypes on the renal artery when compared to that on the normal culture condition (FIG. 24). Furthermore, fluorescence imaging of parenchymal surfaces in the [EC(+)] kidney clearly showed capillary-like structures on the cortical surface, indicating that viable GFP-expressing MS1 cells infiltrated the parenchymal cortex (FIG. 18c). Scanning electron microscopy (SEM) confirmed endothelial cell alignment in the vasculature (FIG. 18d). Homogenous re-endothelialization of different-sized vasculatures was confirmed in different regions of renal parenchymal tissues (FIG. 25). These results showed that MS1 cells were uniformly attached and well-organized on the vascular walls along the direction of perfusion.

In vitro Functional Assessment of Re-Endothelialized Kidney Scaffolds

Figure 19:
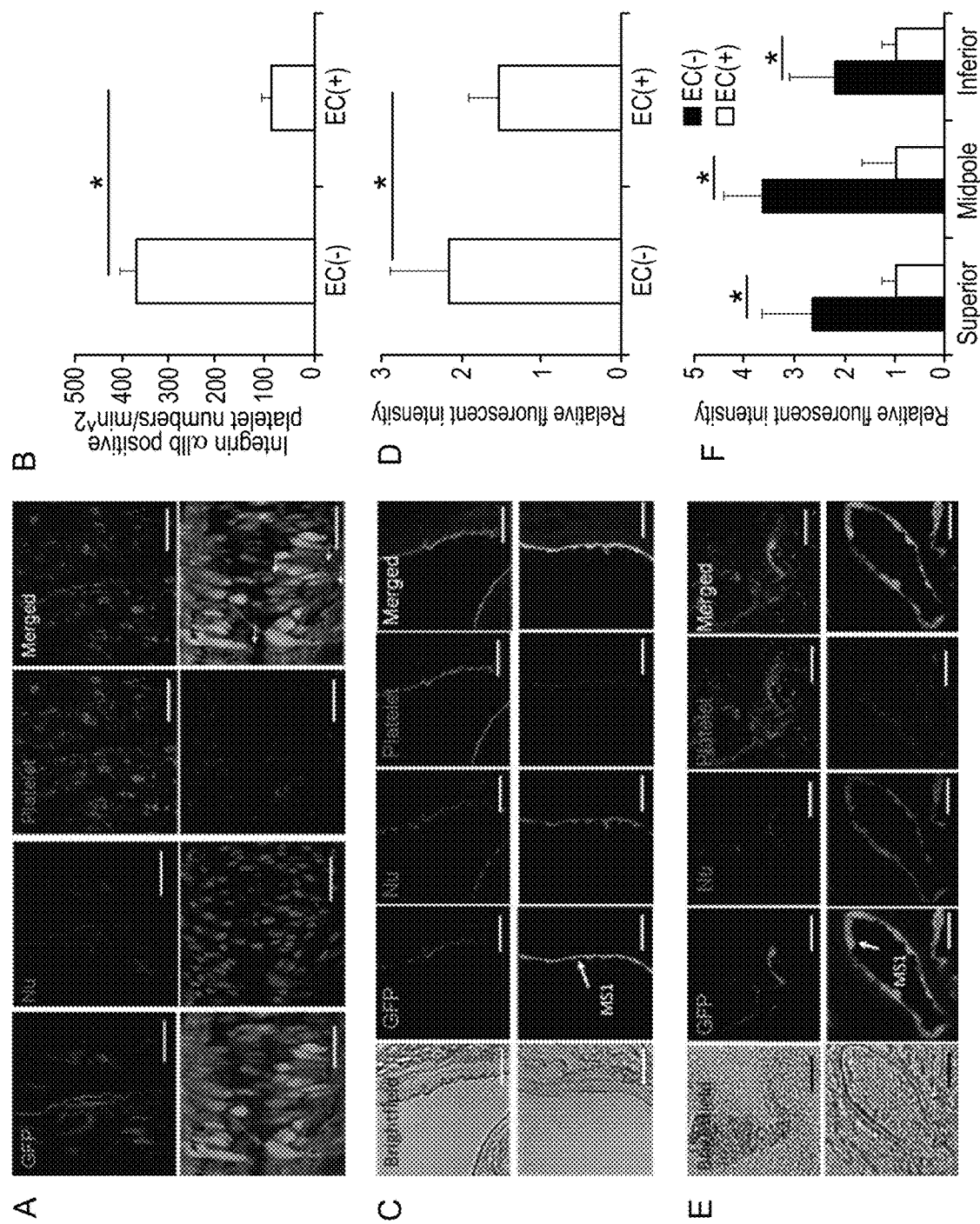
FIG. 19. Imaging and quantification of platelet adhesion on the vasculatures of kidney scaffolds. Numerous integrin αIIb-positive platelets had adhered to the renal artery of [EC(−)] scaffolds (upper panel in a) while the GFP positive MS1 coverage prevented platelet adhesion (lower panel in a), as indicated by arrows in the merged images. Quantitatively, the number of platelets adhered to the artery is significantly lower in [EC(+)] than [EC(−)] scaffolds (*Student t-test, P<0.05, 3-4 sites per kidney, n=3 kidneys) (b). The fluorescent intensity from the integrin αIIb signals was determined to compare the levels of platelet adhesion on intermediate- (c, d) and small-sized (e, f) blood vessels in the parenchyma. Similar to the results from the renal artery and vein, re-endothelialization dramatically reduced platelet adhesion, and this was confirmed by quantitative analysis of intermediate-size (d) (*Student t-test, P<0.05, three blood vessels per kidney, n=3 kidneys) and small size vessels (f) (*Student t-test, P<0.01, nine capillary structured vessels per kidney scaffold, n=3 kidneys). Interestingly, three different sites of the cortex showed this tendency (f). Scale bars: 100 μm (a) and 50 μm (c,e). Data represent mean±SD.
Figure 20:
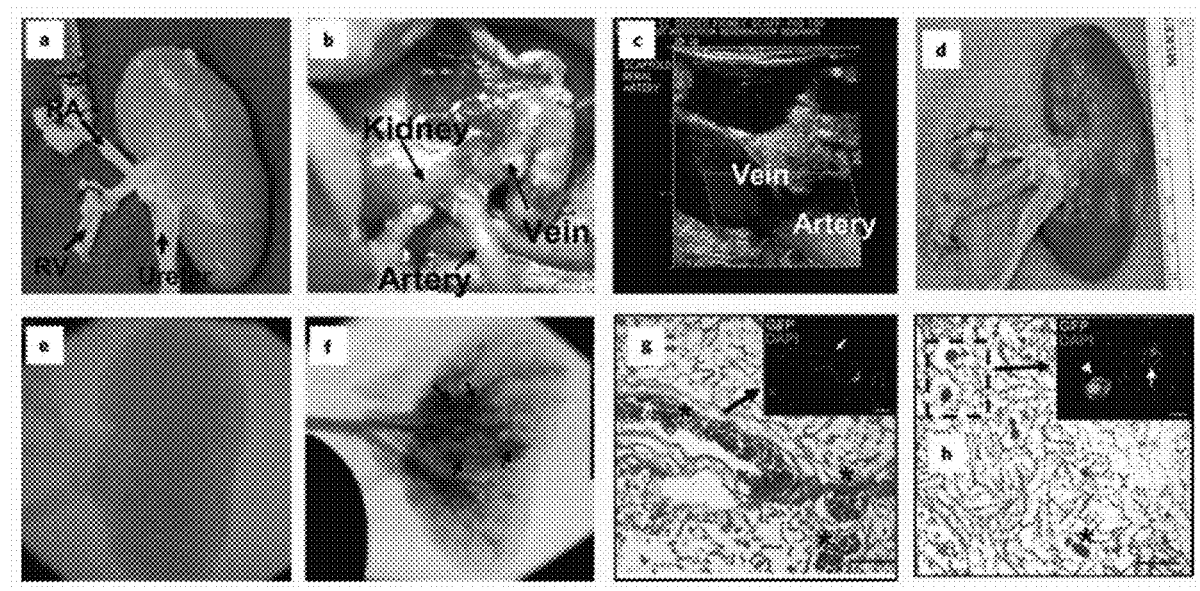
FIG. 20. In vivo implantation of MS1-seeded kidney scaffold into pigs for 2 hours. (a) Before implantation, (b) surgical implantation, (c) ultrasound imaging at 1 hour after implantation, (d) the explanted scaffold from the implantation, and angiogram results of (e) before and (f) after injection of contrast agent, demonstrating severe blood clots (asterisks in g), as confirmed by histological examination (g, h). MS1 detachment (arrows) and cell clogging (arrowheads) are observed in the images of boxes in g and h. Renal artery (RA), renal vein (RV), inferior vena cava (IVC) was shown in the panels. Scale bar: 100 μm (g), 200 μm (h), and 50 μm (box in g and h).
Figure 26:
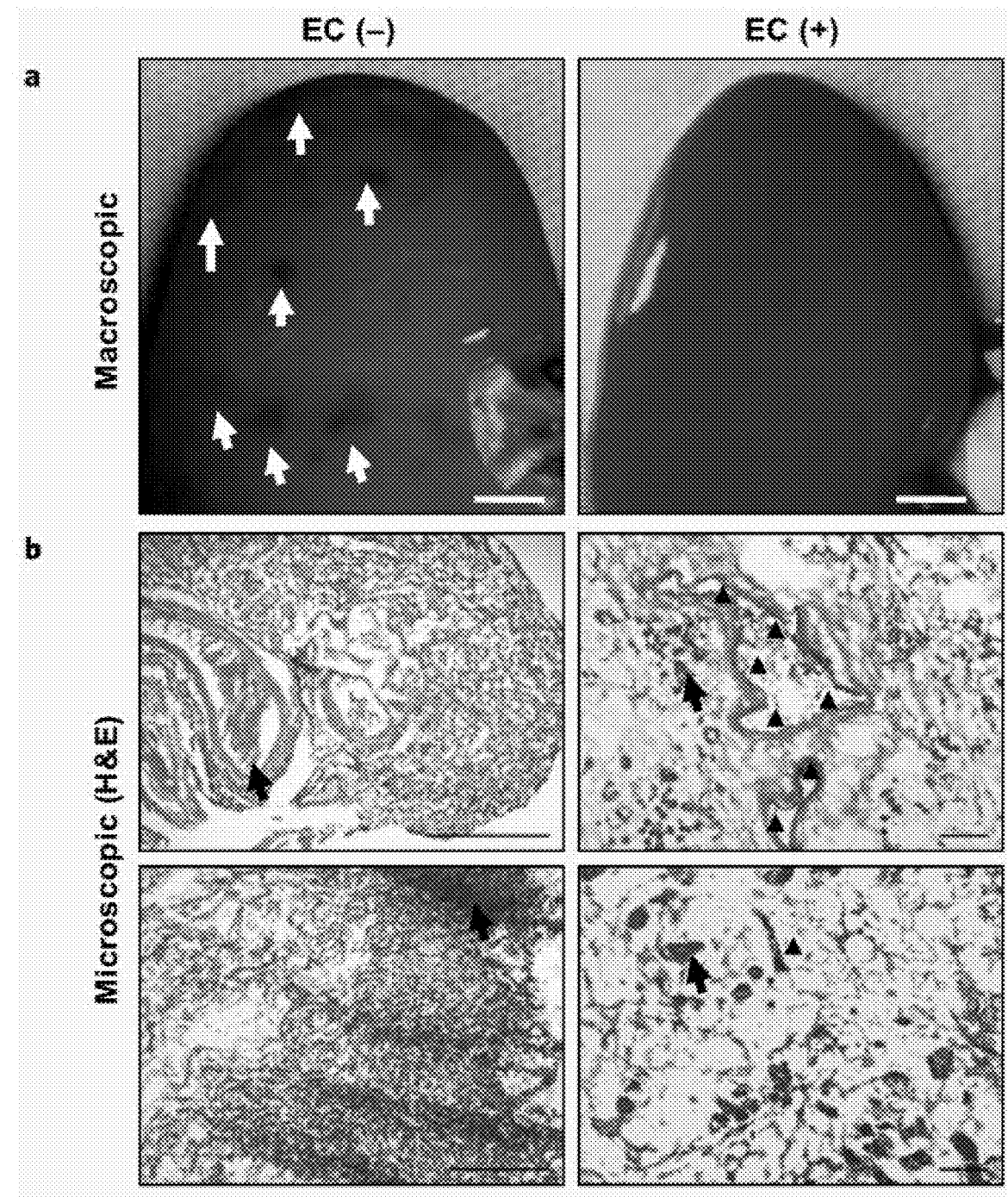
FIG. 26. In vitro blood perfusion to examine the effects of re-endothelialization on the blood clogging and thrombosis. After blood perfusion and rinsing with PBS, gross images of the kidney scaffold (a) showed large blood clot-like objects (arrows) in the unseeded scaffold [EC(−)], while no such finding was detected on the surface of [EC(+)] scaffolds. H&E staining confirmed that severe blood clotting occurred in [EC(−)] scaffolds (arrows in B), whereas the re-endothelialized scaffolds showed intact blood vessels (arrowheads) with only mild blood cell clogging (arrows) in the parenchymal spaces. Scale bars: 1 cm (a), 500 μm [EC(−)], and 100 μm [EC(+)] in (b).
Figure 27:
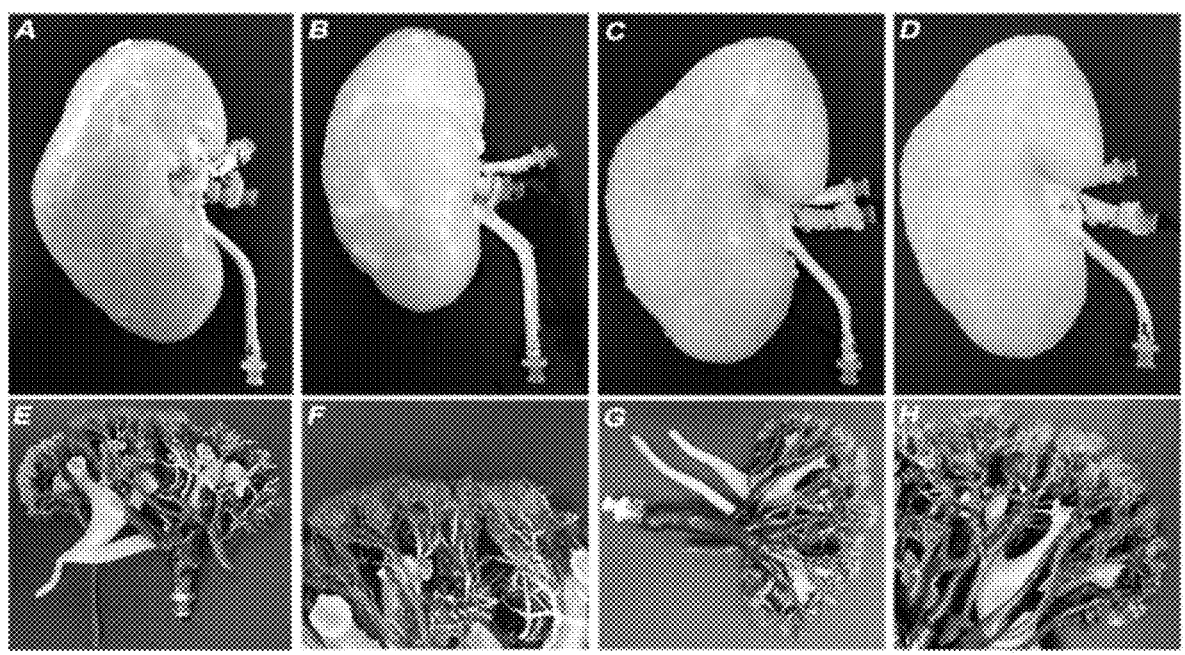
FIG. 27. Whole human kidney de-cellularization and vascular corrosion cast.

To determine whether the seeded kidney scaffolds are functional, heparinized pig blood was perfused through the artery. The functional re-endothelialization of vasculatures was expected to decrease platelet adhesion on re-endothelialized renal scaffolds during blood perfusion and to maintain blood flow through the entire renal parenchyma. Blood infused through the artery of MS1-seeded kidney scaffolds showed significant outflow through the renal vein, indicating that endothelial cell coverage of the vasculature is effective and sufficient to support blood flow throughout the entire kidney scaffold. In contrast, no blood outflow was observed through the renal vein of the EC(−) kidneys. Macroscopic images and H&E staining of the blood-perfused kidney scaffolds confirmed the expectation that clotting was causing the blockage of blood flow in the EC(−) group. Gross images of perfused EC(−) kidney scaffolds clearly showed multiple areas of thrombosis on the parenchymal surfaces (FIG. 26). In contrast, EC(+) scaffolds showed a well-preserved endothelial lining without noticeable blood clots. To demonstrate the effects of re-endothelialization, unseeded and seeded kidney matrices perfused with blood, were immunostained with integrin αIIb antibodies. A minimum expression of integrin αIIb+platelets was observed on the re-endothelialized renal arteries, whereas high levels of platelet accumulation were found in the EC(−) kidneys (FIG. 19a). Quantitatively, the artery in EC(+) kidneys significantly reduced platelet adhesion 4-5 fold compared to EC(−) kidneys (FIG. 19b, P<0.05). Likewise, intermediate- and small-sized blood vessels lined with GFP+MS1 endothelial cells showed no significant platelet adhesion, while strong platelet-derived fluorescence was observed in the EC(−) kidneys (FIGS. 19c, e). The quantification of platelet adhesion by measurement of fluorescence intensity showed a significant decrease in platelet adhesion in the seeded scaffolds (FIGS. 19d, f). To examine whether seeding of MS1 cells onto kidney scaffolds can effectively prevent blood clots in vivo, MS1-seeded kidney scaffolds (FIG. 20a) were implanted in a pig by arterial and venous anastomosis (FIG. 20b). Following implantation, maintenance of blood flow was confirmed in both the renal artery and vein at 1 hour by Doppler Ultrasound (FIG. 20c). Upon retrieval at 2 hours, the explanted kidney showed blood clots within the large blood vessels (FIG. 20d) and occlusion of vascular network was confirmed by angiography. Several areas showed extravasation of contrast medium in the parenchyma (arrows, FIGS. 20e, f). Histological analysis of the explanted kidney scaffolds showed that most of the vasculature throughout the parenchyma in the implanted kidney failed to retain MS1 cell coverage on the vascular walls, indicating that the failure of vascular patency is due to a detachment of endothelial cells after implantation (arrows, FIGS. 20g, h). Detachment of endothelial cells was increased with implantation time increasing from 2 to 4 hours. By 4 hours, re-endothelialized kidney scaffolds had no measurable blood flow in the renal artery and vein (as confirmed by ultrasound imaging and angiography), which is thought to be due to an apparent increase in thrombi located inside the renal vasculature where detachment occurred due to high vascular pressure and flow.

Figure 21:
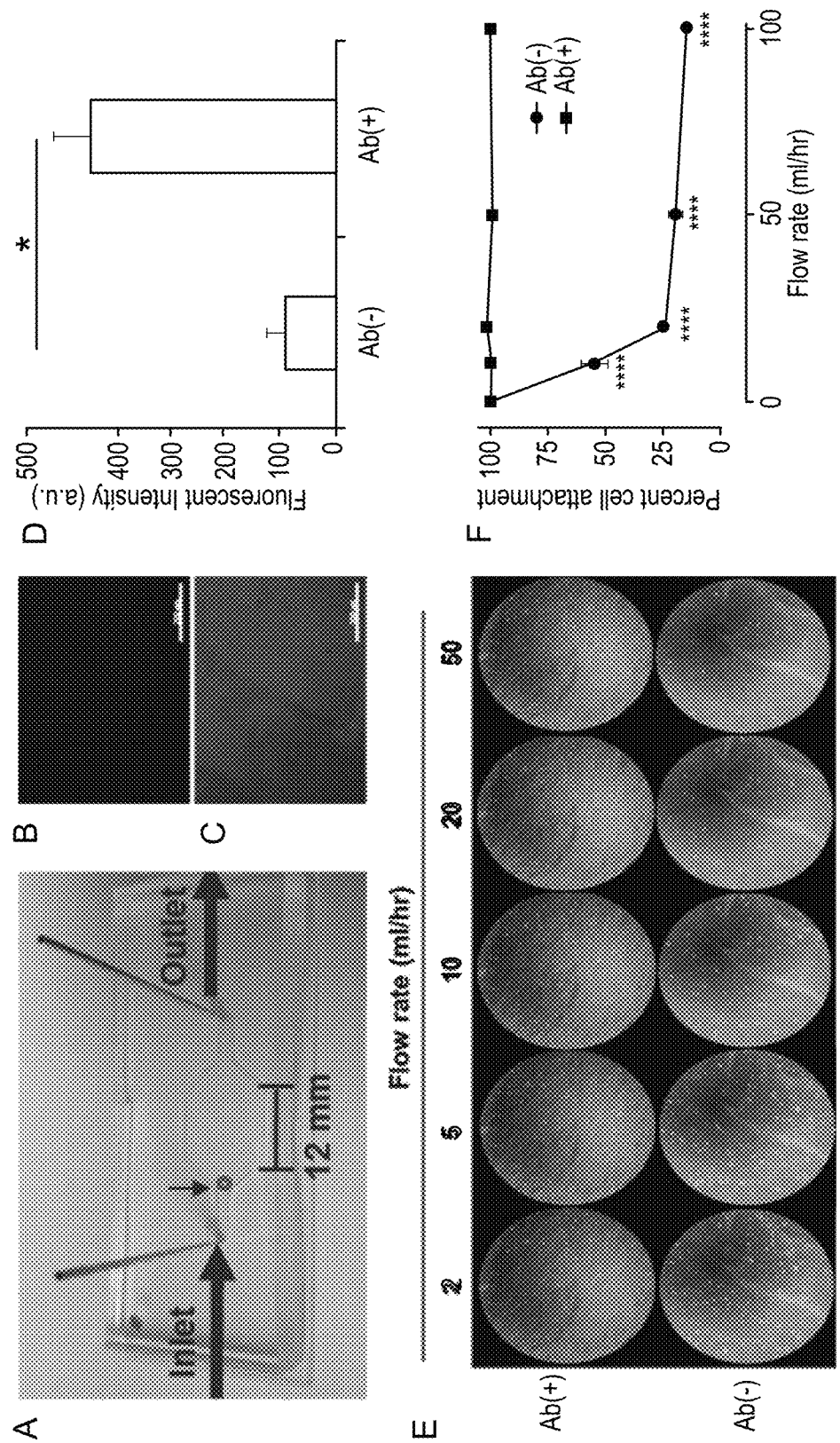
FIG. 21. Cell detachment assay under dynamic flow conditions to determine the effect of antibody conjugation on improvement of cell adherence. A microfluidic system (a) consisting of PDMS-based glass chamber was designed to examine the effect of antibody conjugation on the cell detachment. The conjugated CD31 antibody was visualized as red fluorescent (c) while there is no significant brightness on the untreated surfaces (b). Semi-quantification shows statistical difference between antibody-conjugated surfaces and untreated sample (*Student t-test, P<0.05, n=3). Data represent mean±SD. In the cell detachment test (e, f), MS1 cells that pre-adhered on the Ab-conjugated surfaces [Ab(+)] maintained their cell number; however, cells on the untreated sample [Ab(−)] went detached with the increase of flow rate and reached to higher than 80% of originally pre-attached cells after flowing at 50 ml/hr. Statistically significant differences were found at all points of flow rates (****, two-way ANOVA, P<0.00001, Post-hoc Bonferonni test, P<0.05 for all points, n=4). Scale bar: 200 μm (b,c). Data represent mean±SEM.

Effect of Antibody Conjugation on MS1 Cell Detachment (in vivo) and Endothelial Integrity After Implantation To address the apparent detachment of MS1 cells after implantation in vivo, cell specific antibody was employed to strengthen the binding of endothelial cells expressing CD31. Conjugating CD31 antibody (Ab) to the decellularized vascular matrix was expected to improve MS1 cell attachment during cell seeding as well as cell retention under physiological flow conditions. To test this expectation, CD31 Ab was conjugated onto a collagen pre-coated surface of a microfluidic flow chamber system (FIG. 21a). Conjugation of CD31 Ab was confirmed using a fluorescent-labeled secondary antibody to the CD31 antibody (FIGS. 21b, d). MS1 cells were then placed in the collagen-coated flow chambers±CD31 Ab, and allowed to adhere to the surface for 10 minutes prior to assessing cell detachment in response to a stepwise increase in flow (2-100 ml/hour). There was no detectable endothelial cell detachment in the Ab(+)-conjugated surfaces, whereas there was a significant endothelial cell detachment in the untreated surfaces at all flow rates tested (FIGS. 21e, f, P<0.00001, n=4). These results indicate that CD31 antibody conjugation onto the kidney vascular scaffold improves MS1 cell retention under physiological flow conditions. To determine whether CD31 antibody conjugation could improve MS1 cell retention throughout the renal vascular scaffold in vivo, conjugated scaffolds were implanted into pigs and exposed to physiological blood flow for 4 hours, after which the implanted kidney construct was explanted and angiography was performed to assess vascular patency. Angiography results showed intact and patent vascular trees of parenchyma, which were without extravasation of host blood cells in the [Ab(+)] scaffolds during the entire period (FIG. 22a), confirming the effectiveness of antibody conjugation in the kidney scaffold. This functional outcome was supported by the histomorphological analyses showing that CD31 antibody conjugation significantly maintained endothelialization of intermediate- and small-sized vasculatures (FIG. 22b). Moreover, the endothelium of Ab-conjugated constructs effectively prevented platelet adhesion (FIGS. 22c, d).

Whole-organ engineering using decellularized organ matrices provides the potential to address the limitations of current transplantation. One challenge that must be addressed is to develop a method to prevent thrombosis and maintain continuous blood flow into the engineered organ[16]. In this regard, re-endothelialization of scaffold vasculature has become a promising solution. Although approaches have been employed to establish endothelial cell coverage of vascular trees within decellularized organs, complete and uniform coverage could not be achieved, thus resulting in the failure of long-term patency in vivo[2-5,8]. Disclosed herein is an approach that has developed and optimized a cell-seeding method that results in uniform coverage of endothelial cells across different sizes of blood vessels within the kidney scaffold. More importantly, retention of seeded endothelial cells can be maintained with the conjugation of CD31 antibody to decellularized vascular matrix prior to seeding. In this study several cell seeding methods were tested; however, these techniques resulted in limited or no cell attachment in the intermediate- and large-sized blood vessels with cell "clogging" within the small capillaries in the renal cortex, indicating a need for improved cell seeding methodology. As such, the static and ramping-perfusion seeding methods, which resulted in uniform endothelial cell coverage within the vascular matrix of the renal scaffold, were combined.

Vascular patency as a function of endothelial cell-covered vessel was demonstrated by infusion of whole blood into the artery of kidney scaffolds. To demonstrate the function of endothelial cell covered-vessels, heparinized pig blood was infused into the renal artery of the endothelialized scaffold. Blood perfused through the artery of cell-seeded kidney scaffolds showed outflow through the renal vein. Moreover, the vasculatures within the scaffold maintained stable endothelial cell adherence under high flow conditions (100 ml/min) and showed minimal expression of platelet adhesion, indicating that endothelial cell-covered vasculature is effective and sufficient to support blood flow throughout the entire kidney scaffold. To test the feasibility of implantation of engineered kidney scaffolds in vivo, a surgical technique previously developed in pigs was used, and the experiment showed the intactness of implanted scaffolds. Vascular flow could not be maintained, however[15]. To address this issue, re-endothelialized kidney scaffolds were implanted using the combination seeding method to maintain blood flow into the implant. This approach demonstrated scaffold patency for 2 hours after implantation, after which significant clot formation was observed in the parenchyma. Based on this observation and histological analysis of the kidney scaffolds, it was evident that endothelial cell detachment, which may have occurred from the high intravascular pressure and flow, was the primary cause for thrombosis in the renal scaffold. Accordingly, a method was developed to strengthen the endothelial cell attachment sufficiently to endure physiologic vascular conditions.

Figure 22:
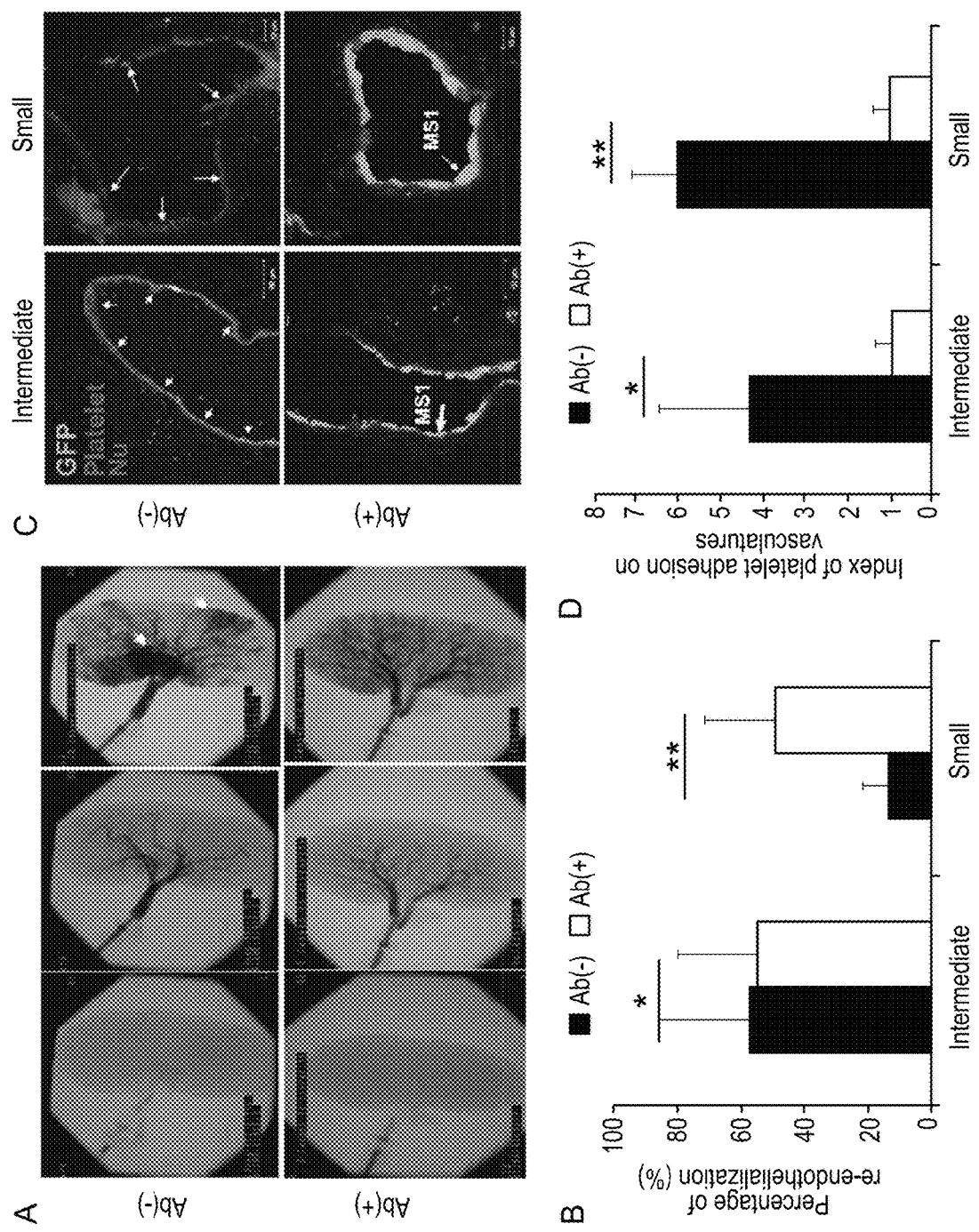
FIG. 22. In vivo kidney implantation to determine the effect of CD31 antibody conjugation of kidney scaffolds on the vascular maintenance. The re-endothelialized kidney scaffolds without [Ab(−)] and with [Ab(+)] antibody conjugation were implanted into pigs for 2 and 4 hours, respectively. The angiogram of the harvested kidney scaffolds showed massive blood clots/occlusions and extravasation of host blood cells in [Ab(−)] (indicated by arrows), whereas a patent vascular tree was observed in [Ab(+)] (a). This functional outcome was confirmed by histological examination, showing higher percentage of MS1 endothelialization of [Ab(+)] than that of [Ab(−)] in the medulla site (intermediate-sized vessels, 3 sites per kidney, n=3 kidneys per group) and small-sized vessels in the cortex (9 sites per kidney, n=3 kidneys per group) (Student t-test,*P<0.05, **P=0.059) (b). The immunostaining using platelet marker (=IIb integrin) showed numerous platelet adhesions (arrows) on the lumens of naked vasculatures of [Ab(−)], while low adhesion was detected on the MS1-adhered intermediate and small blood vessels of [Ab(+)] (c). The extent of platelet adhesion was significantly different with statistical analysis (*Student t-test, P<0.05) (d). Scale bar: 50 (intermediate) and 10 μm (small) (c). Data represent mean±SD.

In this study, an antibody conjugation technique was employed to modify the vascular surfaces of a scaffold in order to enhance endothelial cell adhesion. In in vitro testing using a flow chamber system, the conjugation of an endothelial cell-specific antibody against CD31 to the chamber surface prevented endothelial cell detachment under high flow conditions. This in vitro experiment was performed to confirm the effectiveness of antibody conjugation and the ability of conjugated antibodies to capture cells in motion. The flow rates used for in vitro flow chamber study are much lower than the cell seeding experiments performed with the kidney scaffold. Following implantation of re-endothelialized CD31 antibody-conjugated kidney scaffolds, prolonged endothelial cell attachment to the antibody-conjugated scaffolds was observed that significantly improved vascular patency throughout the parenchyma in vivo. This study shows that the re-endothelialization technique disclosed herein, combined with cell-specific antibody conjugation, results in uniform coverage of endothelial cells within the vasculature of decellularized kidney scaffold and maintains cell attachment leading to prolonged blood flow under physiological vascular conditions. These results have demonstrated that reinforcement of endothelial cell attachment by antibody conjugation improved vascular patency following implantation (FIG. 22). However, it is possible that a relative lack of endothelial cell coverage on the conjugated vascular surface during implantation may attract interaction with other cell types in the blood, such as platelets, monocytes, and neutrophils. To reduce the possibility of such interaction, other anti-thrombotic substances, such as heparin, could be co-conjugated with CD31 antibody. In the platelet adhesion experiment using whole blood that has been disclosed herein, an antibody-conjugated surface significantly reduced platelet adhesion when compared to a non-conjugated vascular surface.

The experiments disclosed herein demonstrate the effectiveness of antibody conjugation-mediated re-endothelialization. One study showed that the antibody-conjugated re-endothelialized vessels maintained patency over a period of 4 hours, while the controls without antibody conjugation resulted in complete obstruction due to thrombosis. The renal blood flow (RBF) rate of pig is approximately 470 ml/min[17], and maintaining renal vascular patency for 4 hours corresponds to 112.8 liters of blood flow into the scaffolds. This study further confirms the feasibility of using porcine-derived decellularized whole kidney as a scaffold for renal tissue engineering. The recellularization and reinforcement methods disclosed herein would serve as an intermediate step to clinical translation of the decellularized scaffold approach. Previous studies in this area have used small animals, such as rodents[3-5]. The porcine kidney transplantable scaffold as disclosed herein provides a renal acellular matrix that has a number of advantages, including: (1) similarity to human kidneys in size, (2) lowered infection risk associated with the transplantation process, and (3) heightened relative safety in using pig material, as other acellular porcine tissues, such as heart valve[18] and small intestinal submucosa (SIS) matrix[19], have already been safely used in the clinic. The use of porcine whole renal scaffolds for renal tissue engineering is reasonably expected to translate to an application in humans. We further expect that an approach termed "semi-xenotransplantation"[16], where autologous cells from the patient could be used to repopulate the acellular porcine kidney matrix, to be safe and effective. The results presented here indicate that endothelial cell seeding into the vascular network within acellular porcine kidneys is feasible and results in homogenous formation of endothelium. These results provide evidence that it is possible to produce a fully endothelialized vascular tree that maintains vascular patency and delivers nutrients and oxygen to engineered kidneys, as well as other engineered whole organ systems.

REFERENCES—FOR EXAMPLE 9 ONLY

1. Chazan, J. A. et al., Clin. Nephrol. 35, 78-85 (1991).
2. Ott, H. C. et al., Nat. Med. 14, 213-221 (2008).
3. Petersen, T. H. et al., Science 329, 538-541 (2010).
4. Uygun, B. E. et al., Nat. Med. 16, 814-820 (2010).
5. Baptista, P. M. et al., Hepatology 53, 604-617 (2011).
6. Atala, A. et al., Sci. Transl. Med. 4, 160rv12 (2012).
7. Crapo, P. M. et al., Biomaterials 32, 3233-3243 (2011).
8. Ott, H. C. et al., Nat. Med. 16, 927-933 (2010).
9. Song, J. J. et al., Nat. Med. 19, 646-651 (2013).
10. Ross, E. A. et al., J. Am. Soc. Nephrol. 20, 2338-2347 (2009).
11. Ross, E. A. et al., Organogenesis 8, 49-55 (2012).
12. Nakayama, K. H. et al., Tissue Eng. Part A 16, 2207-2216 (2010).
13. Sullivan, D. C. et al., Biomaterials 33, 7756-7764 (2012).
14. Ko, I. K. et al., Biomaterials 30, 3702-3710 (2009).
15. Orlando, G. et al., Ann. Surg.256, 363-370 (2012).
16. Orlando, G. et al., Transplantation 91, 1310-1317 (2011).
17. Daghini, E. et al., Radiology 243, 405-412 (2007).
18. Lawton, J. S. et al., J. Thorac. Cardiovasc. Surg. 137, 1556-1557 (2009).
19. Iannotti, J. P. et al., J. Bone Joint Surg. Am. 88, 1238-1244 (2006).

EXAMPLE 10

Whole Organ Engineering—Re-Endothelialization of Kidney Scaffolds

Regenerative medicine has shown immense potential to address the limited number of transplantable organs and to allow immunosuppression-free transplantation, through the generation of body parts from patient's own biomaterials[1]. Among the various approaches to organ bioengineering or regeneration, the seeding of cells on supporting scaffolding material—namely, cell-on-scaffold seeding technology (CSST)[2]—seems to offer the quickest route to clinical application. In fact, this technology has allowed the production of numerous, yet relatively simple body parts for therapeutic purposes, that were eventually implanted in more than 200 patients[1].

In the wake of these preliminary, yet groundbreaking achievements, CSST is being applied also to manufacture more complex, metabolic, transplantable organs, including the kidney. In particular, extracellular matrix (ECM) scaffolds obtained through the detergent-based decellularization of multiple species are used as a template for the seeding of kidney-specific cells or progenitor cells, in an attempt to regenerate the parenchymal compartment, as well as of endothelial cells or progenitor cells aiming at the full regeneration of the endothelium. Since the very first report by Ross et al.[3] on the production of bioactive ECM scaffolds from rodent kidneys, several studies have followed[4-12] and have provided evidence that renal ECM scaffolds can be successfully and consistently produced from virtually all species including humans[9,13], are completely acellular and virtually non-immunogenic, maintain their architecture and essential molecular composition, lack cell membrane molecules, are able to determine cell phenotype and induce genes of renal development, possess remarkable angiogenic properties as demonstrated by the ability to induce vessel formation in the chorioallantoic membrane, are biocompatible in vitro and in vivo, and, when repopulated with renal cells, are able to show some function. Moreover, when acellular porcine renal ECM scaffolds are implanted in pigs, the framework of the innate vasculature remains well preserved and is able to well sustain physiologic blood pressure[4].

In order to validate these promising preliminary data in a more clinically relevant model, our group is applying CSST to human kidneys initially procured for transplant purposes, but eventually discarded for various reasons[13]. In fact, in the United States, because more than 2600 kidneys are discarded annually from the total number of kidneys procured for transplantation, we viewed this organ pool as having potential for use as a platform for renal bioengineering and regeneration research. We showed that SDS-based decellularization consistently and successfully yields human renal ECM scaffolds (hrECMs) with a well-preserved three-dimensional architecture, an intact glomerular basement membrane along with other important structural proteins. Notably, these scaffolds lack HLA antigens and possess a striking ability to induce angiogenesis, which is an essential biological characteristic of any biomaterials in view of optimal, ad hoc re-cellularization and function following implantation in vivo.

Therefore, the disclosed study was conceived, designed and implemented to complete the characterization of hrECMs by evaluating, for the first time, the microvasculature using the resin casting method, in addition to robustly assessing the dimension of the glomerular capillaries and arterioles. Moreover, in order to thoroughly assess the compliance and resilience of the framework of the innate vasculature within hrECMs, the actual arterial and venous pressures were measured within the framework of the vasculature of our matrices, with the use of a pulse-wave, set within the physiological limits. Finally, an assessment was made of the presence of soluble growth factors (GFs) that possibly can be retained within the rhECMs and that are responsible for inducing angiogenesis.

Kidney Procurement and Preparation

Kidneys were procured for transplant purposes but then discarded for various reasons including anatomical abnormalities such as glomerulosclerosis, interstitial fibrosis, tissue inflammation or cortical necrosis. All organs were procured within the designated service area of our local procurement organization (Carolina Donor Service) and were refused by all local, regional, and national transplant centers. Kidneys were offered to the transplant team of the Wake Forest School of Medicine and processed at the Wake Forest Institute for Regenerative Medicine after the complete exhaustion of the national list.

Kidneys were received in sterile cold solution (saline solution NaCl 0.9%) and preserved until shipment. The aortic patch and the renal vein were prepared according to transplant protocol. The renal vein was dissected and sectioned at 2 cm from its origin. Multiple arteries were reconstructed in order to create a single arterial inlet. Peripheral fat and lymphatic tissue were ligated with 2/0 silk ties. Sixteen gauge intravenous catheters were inserted into the renal artery, the renal vein, and the ureter. The renal artery and the ureter were subsequently tested for possible leakages and eventually repaired with 6/0 Prolene sutures. Because all kidneys had been biopsied at the upper pole at the time of procurement, a renorrhaphy of the "wedge" defect was performed with 4-0 PDS suture in a running way. Kidneys were finally placed on ice until decellularization.

Kidney Decellularization and hrECMs Production

The angiocatheters previously inserted in the renal artery and in the ureter were connected to a pump (Masterflex L/S peristaltic pump with Masterflex L/S easy load pump head and L/S 16G tubing, Cole-Palmer Instrument Co, Vernon Hills, Ill., USA) to allow continuous rinsing with different solutions, starting with phosphate buffer saline (PBS) at the rate of 12 ml/minute for 12 hours (8,640 mL total).

Afterward, 0.5% sodium dodecyl sulfate (SDS, Sigma-Aldrich, St. Louis, Mo., USA)-based solution was delivered at the same flow rate for 48 hours (34,560 mL total) in both the renal artery and ureter. Finally the kidneys were rinsed with DNase (Sigma-Aldrich, St. Louis, Mo., USA) for 6 hours at a flow rate of 6 ml/hour and then with phosphate buffer saline, PBS (Sigma-Aldrich, St. Louis, Mo., USA) at the same flow rate for 5 days (43,320 mL total). The histological characterization of the bioscaffolds was performed as previously described[13] in order to confirm absence of cellular residual.

Resin Vascular Cast

Resin casting of the innate vasculature was obtained as previously described[14,15]. A total of 16 kidneys underwent resin vascular cast treatment divided into two different groups: group 1 counting eight native/cellular kidneys versus group 2 counting eight hrECMs. Precasting treatment was carried out via injection through arterial inlet of 60 ml heparinized PBS solution in order to prevent any kind of blood clotting while washing out the remaining blood from the vasculature tree. For each kidney, 60 ml of specific casting resin was prepared by mixing 50 ml of casting resin monomer (Batson's #17 Monomer Base Solution Cat #02599, Polyscience, Inc., Warrington, Pa., USA), 10 ml of catalyst (Batson's #17 Anatomical Corrosion Kit Promoter Cat #02610, Polyscience, Inc., Warrington, Pa., USA) and 10 drops of promoter (Batson's #17 Catalyst Cat #02608, Polyscience, Inc., Warrington, Pa., USA). This solution was then slowly injected through the renal artery (15-20 ml colored by red dye, Batson's #17 Anatomical Corrosion kit Red dye Lot #533945, Polyscience, Inc., Warrington, Pa., USA) the renal vein (15-20 ml colored by blue dye, Batson's #17 Anatomical Corrosion kit Blue dye Lot #623514, Polyscience, Inc., Warrington, Pa., USA) and the ureter (10-15 ml colored by yellow dye, Batson's #17 Anatomical Corrosion kit Yellow dye Lot #623514, Polyscience, Inc., Warrington, Pa., USA). After the onset of polymerization kidneys were placed in deionized water overnight and then all the tissue was cleared by two alternating rinses (24 hours each) with 10% and 5% of hydrochloric acid, respectively.

Scanning Electron Microscopy (SEM)

Five 5×5×5 mm samples were obtained from each kidney cast (a total of eighty samples, forty from group 1 and forty from group 2) in randomly selected areas of the cortex simply cutting them out with microsurgical scissors. These samples were mounted on silver plates sputter coated with gold and analyzed by Scanning Electron Microscopy (SEM) at 15 KV (Hitachi S-2600N Scanning Electron Microscopy, Hitachi, Chiyoda, Tokyo, Japan). From each sample, two three-dimensional images of the afferent artery and the glomeruli were taken (for a total of 160 glomerular images captured). All of the images were then analyzed by Image-J software (http://rsb.info.nih.gov/ij/). Afferent artery diameter was measured at three different points and averaged for statistical analysis. Glomerular diameter measured in the long and short axis and subsequently averaged. Modeling each glomerulus as a sphere, these diameter averages were used to calculate volume ($\frac{4}{3}\pi r^3$). Six randomly selected glomerular capillaries from each image were measured and used to calculate average capillary diameter. From these data, the morphological properties of the glomeruli and their afferent arteries were evaluated.

Determination Of Machine-Perfusion Vascular Responsiveness

Nine donated human kidneys were machine-perfused at 4° C. for 12 hours with modified Krebs solution, using a unique cardioemulation perfusion technology (VasoWave®, Smart Perfusion, Denver, N.C.). This system produces a cardioemulating pulse wave to generate physiological systolic and diastolic pressures and flow rates within the organ. The system is capable of controlling the oxygen content of the perfusate above and below physiological norms. During perfusion, arterial pressure measurements were taken. A comparison was made between machine-set pressures (systolic/diastolic) and actual pressures within organs under perfusion. Organs with intact vasculature replicate an elastic response to machine-set pressures. Following decellularization, scaffolds from the same set of nine human kidneys were again machine-perfused (modified Krebs solution at 4° C., for 12 hours) and arterial pressure measurements were taken as described. It is important to note that, if scaffolds had been damaged by decellularization, they would not elastically respond to machine-set pressures, and would leak fluid and would fail to sustain pressurization. Pressure measurements were collected for both cellularized and decellularized kidneys at a rate of 100/second and then sampled every 1000 points to create mean summary data.

Growth Factor Retention 5 hrECMs and 5 samples of native kidneys before decellularization were used to evaluate growth factor retention. Samples were procured with a 7 mm biopsy punch, stored in sterile PBS with 2% pen/strep (Hyclone Pe/Strep solution, Fisher Scientific, Waltham, Mass., USA) and then shipped to the manufacturer (Raybiotech, http://www.raybiotech.com/) and processed accordingly. Specifically, tissue biopsies underwent homogenization by sonication in RayBiotech's proprietary lysis buffer (500 μL of lysis buffer per 10 mg tissue) and centrifugation for 5 minutes at 10,000×g. Supernatants were then collected and assayed immediately or frozen for future use. Protein expression profiles were collected using the RayBio® Human Growth Factors Antibody Array G series 1, a custom glass chip-based multiplex ELISA array which measures 40 cytokines simultaneously. The tissue supernatants were incubated with the array chips after a blocking step and these were washed to remove nonspecific proteins, and biotin-labeled detection antibodies were added. The cytokine-antibody-biotin complexes can then be visualized through the addition of a HiLyte Fluor 532™ dye-labeled streptavidin. Spot intensities extracted from the scanned array image were normalized to positive controls included within each array. Average fluorescent intensity was obtained from duplicate signal intensities, adjusted to remove background and normalized to a positive control to account for differences among sub-arrays.

Immunofluorescence to Assess Maintenance of Structural Specific hrECMs Components In order to evaluate the presence of specific hrECM proteins, 1 $cm^3$ biopsies taken from the cortex of decellularized human kidneys were fixed in 10% formalin (Azer scientific, PA) for 2 hours. After fixation, samples were dehydrated in alcohol gradients and placed in toluene (Sigma-Aldrich, St. Louis, Mo.) for 30 minutes. Samples were kept overnight in a 50:50 toluene:paraffin mixture. Samples were next changed into paraffin for 2 hours and later embedded. 5 μm thick sections (Rotary Microtome-Leica, Rotary Microtome RM2235) were deparaffinized and rehydrated in alcoholic gradients for histology. Immunofluorescence analysis was conducted by overnight incubation with primary antibodies Collagen IV (ABCAM, Cambridge, Ma. 1:100), VEGFR-2 (ABCAM, Cambridge, Ma. 1.5:100), VE-Cadherin (ABCAM, Cambridge, Ma. 1.5:100) followed by 30 minute incubation with secondary anti-mouse or anti-rabbit Alexa Fluor 555 (Life Technologies Grand Island, NY 1:500). DAPI mounting (Vector Laboratories Burlingame, CA) was used to visualize samples with a Leica DM5500 B Microscope System.

Statistics

All graphical data are displayed as the mean+SEM. Statistical analysis was performed using the Student's T-test and MatLab Software in order to compare measurements of glomeruli, arterioles and capillaries between the two experimental groups as well as the machine-perfusion vascular responsiveness. A p value less than 0.05 was considered statistically significant.

Cast Preparation and Morphometric Analysis

The resin filled the framework of the innate vasculature throughout the whole parenchyma, ultimately producing a high-fidelity three-dimensional casting, as shown in FIGS. 40A-D. The corrosion cast protocol successfully produced 16 satisfactory whole-kidney casts (8 native kidneys and 8 scaffolds), with uniform representation of the vascular network and glomeruli through the entire cortex, as shown in FIGS. 40E-H.

Figure 28:
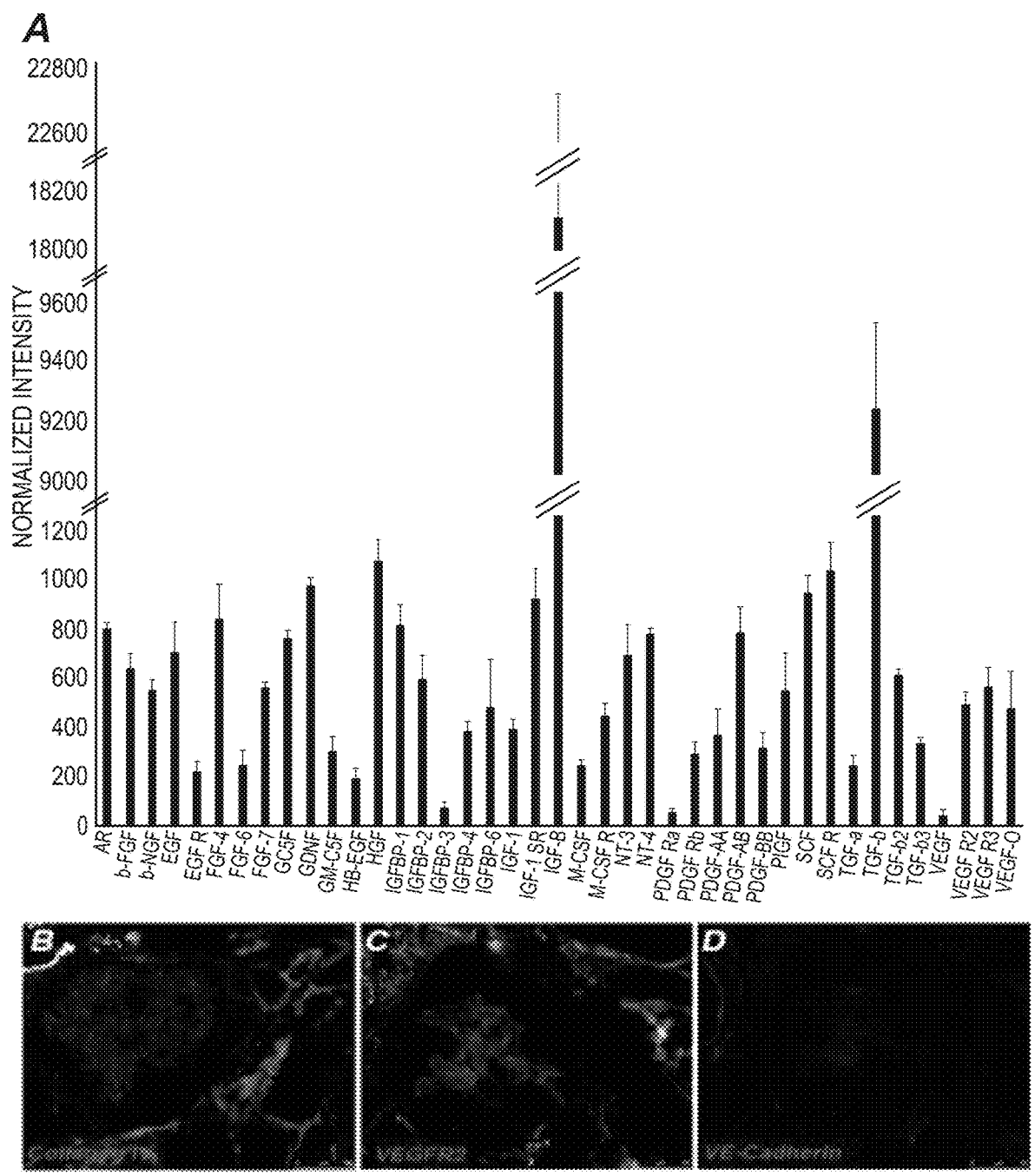
FIG. 28. Glomerular Scanning Electron Microscopy—SEM—morphometric analysis.
Figure 29:
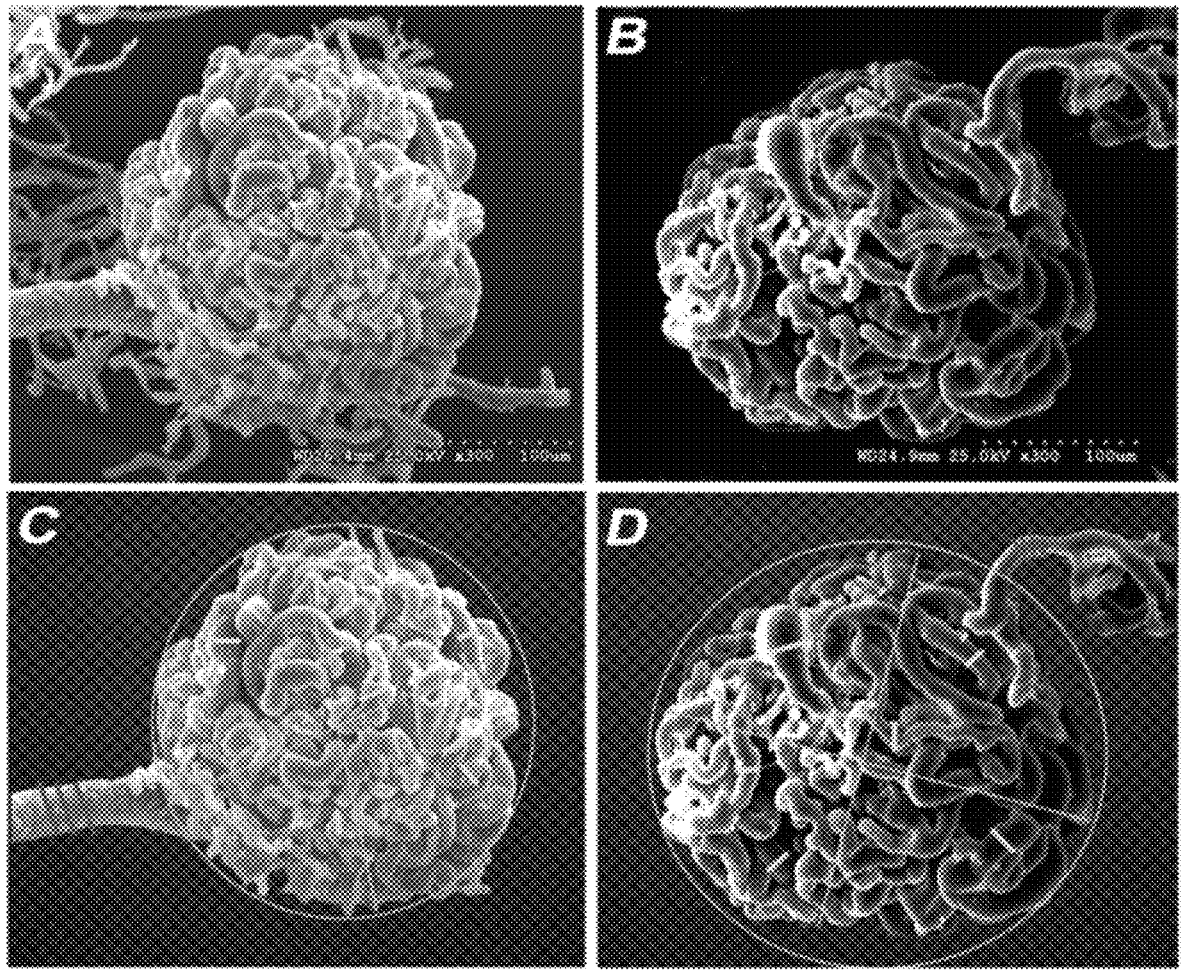
FIG. 29. Morphometric analysis of native and de-cellularized glomeruli. The graphs present in FIG. 3 exemplify the mean measurements expressed in um and um$^3$, of glomerular diameter (A), glomerular volume (B), afferent arteriolar diameter (C) and glomerular capillary with between 80 glomeruli derived from native kidney cast samples and 80 de-cellularized glomeruli derived from kidney cast samples. While glomerular diameter and volume significantly decrease in after de-cellularization, no change was noticed in arteriolar and capillary dimensions before and after de-cellularization. ** $p<0.01$.

Five biopsies were taken from each organ and scaffold. Of each biopsy, five SEM images of randomly selected glomeruli were captured and studied (FIG. 28). Morphometrical endpoints were: sagittal and transversal glomerular diameter (green lines); diameter of the afferent artery (red lines);

diameter of six different glomerular capillaries, randomly selected (yellow lines). Results are shown synoptically in FIG. 29. The average afferent arteriolar diameter was 24.20±0.49 µm in native kidneys versus 23.65±0.63 µm in hrECMs (p=n.s.). The average glomerular diameter was 224.37±5.23 µm in the native kidneys versus 182.93±3.8 µm in the scaffolds (p<0.01). Volumetric calculations were carried out using these figures by modeling glomeruli as spheres. Analysis showed that volume of native glomeruli was statistically higher that in the hrECMs ($7.17 \times 10^6 \pm 6.62 \times 10^5$ µm$^3$ versus $3.81 \times 10^6 \pm 3.07 \times 10^5$ µm$^3$, p<0.01). Mean capillary width was 11.36±0.20 µm for native kidneys and 11.37±0.20 µm for renal scaffolds (p=n.s.). The mean afferent arteriolar diameter was 24.20±0.64 µm for native kidneys and 23.65±0.72 µm for renal scaffolds (p=n.s.).

Machine-Perfusion Vascular Responsiveness

In order to evaluate the effects of decellularization, the vascular elasticity and ability to sustain pressure in both intact (pre-de-cellularization) and processed (post-de-cellularization) kidneys was measured. To accomplish this, the VasoWave perfusion system was connected to the arterial and venous vessels and pulsing was applied while measuring pressure responsiveness and fluid load in the closed-loop system. Machine-perfused kidneys and hrECMs stabilized within 20 minutes of anastomosis and were effectively perfused in a closed-circuit system using 1-1.5 L of modified Krebs solution for 12 hours. No interstitial edema or swelling was noted and there was no fluid 'weeping' from the surfaces or under the capsule of the experimental groups.

Figure 30:
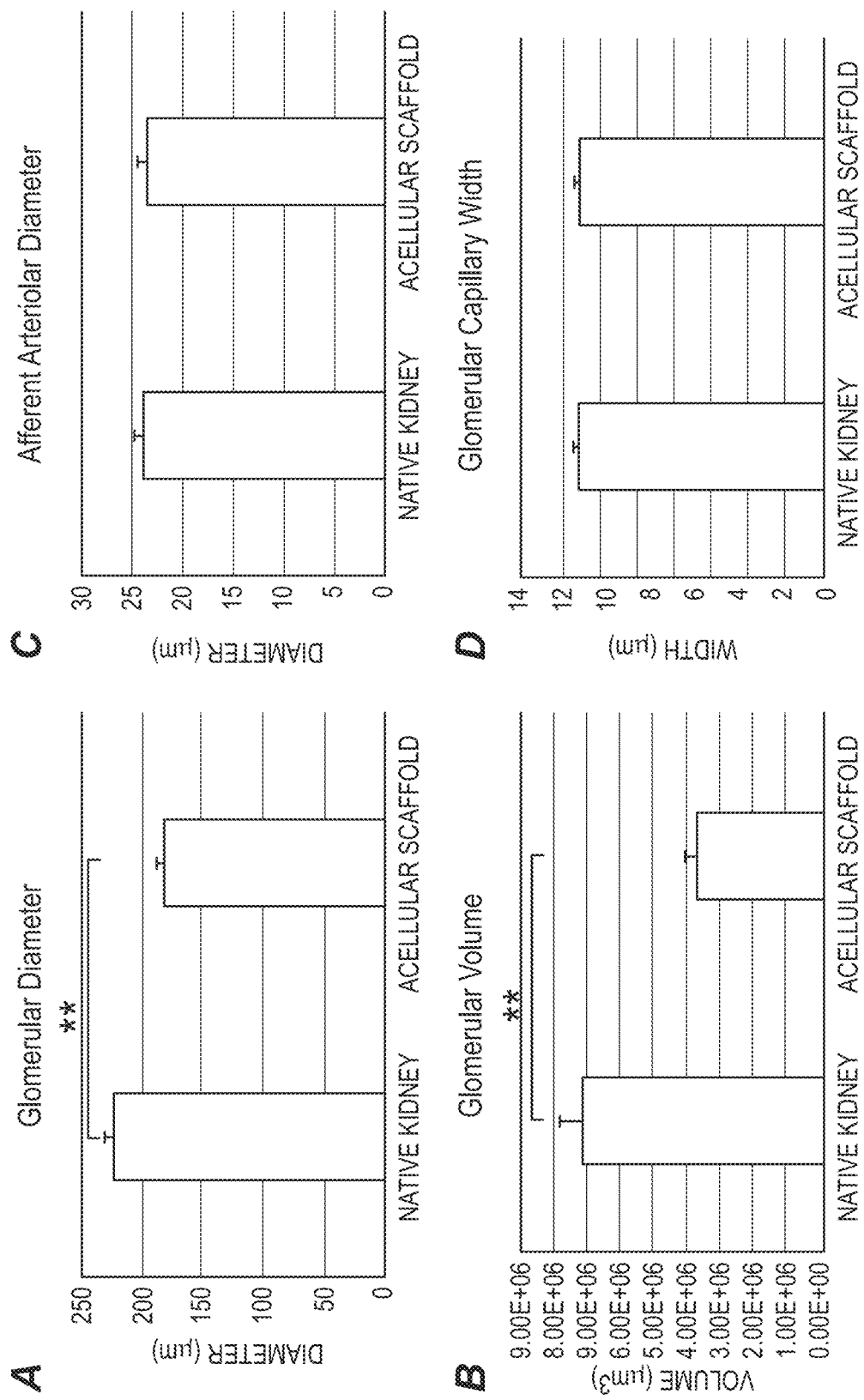
FIG. 30. Measurement of mean systolic (Max) and diastolic (Min) pressure responsiveness. Panel A shows the measurement of mean systolic pressure responsiveness of nine human kidneys (before and after de-cellularization) machine-perfused at 90 mm Hg for 12 hours. Points represent the percent difference in the machine-set pressure and actual pressure. Native kidney, (blue line) and de-cellularized kidney, hrECMs (orange line) demonstrated an elastic response to machine set pressures (black line). The mean vascular elastic response in the native kidney was 0.898% versus 1.76% after de-cellularization. Panel B shows the measurement of mean diastolic pressure responsiveness of nine human kidneys (before and after de-cellularization) machine-perfused at 50 mm Hg for 12 hours. Points represent the percent difference in the machine-set pressure and actual pressure. Native kidney (blue line) and de-cellularized kidney, hrECMs (orange line) demonstrated an elastic response to machine set pressures (black line). The mean vascular elastic response in the native kidney was 7.47% versus 2.48% after de-cellularization. Presence of an elastic rebound in response to the applied pulse wave confirmed that de-cellularization diminished but did not compromise the elastic response of the vascular scaffold.

As shown in FIGS. 30A and 30B, the vasculature of both native kidney and hrECM demonstrated an elastic response to machine-set pressures. With a machine-set systolic pressure of 90 mmHg, the mean vascular elastic response of the native organ (measured by the difference of set versus actual pressure) was 0.898%. The mean vascular elastic response of the native organ to the diastolic (50 mm Hg) pressure wave was 7.47%. Of note, administration of the arterial pressure wave temporally resulted in slightly higher actual arterial pressures, due to arterial dilation opposed by tissue pressure and venous backpressure. This is commonly seen as a manifestation of vascular resistance in normal kidneys.

Following de-cellularization, vascular elastic responses were again evaluated in the same 9 kidneys. With a machine-set systolic pressure of 90 mm Hg, the mean vascular elastic response of the hrECMs (measured by the difference of set versus actual pressure) was 1.76%. There was no temporal rise in actual arterial pressure, demonstrating that decellularization effectively removed tissue backpressure. The mean vascular elastic response of the hrECMs to the diastolic (50 mm Hg) pressure wave was 2.48%. Removal of cellular material did not compromise the elastic response of the vascular scaffold. In fact, smoothing of the elastic response was indicative of more effective perfusion (less difference in the diastolic mean deviation from the machine-set pressure wave).

Growth Factor Analysis

Figure 31:
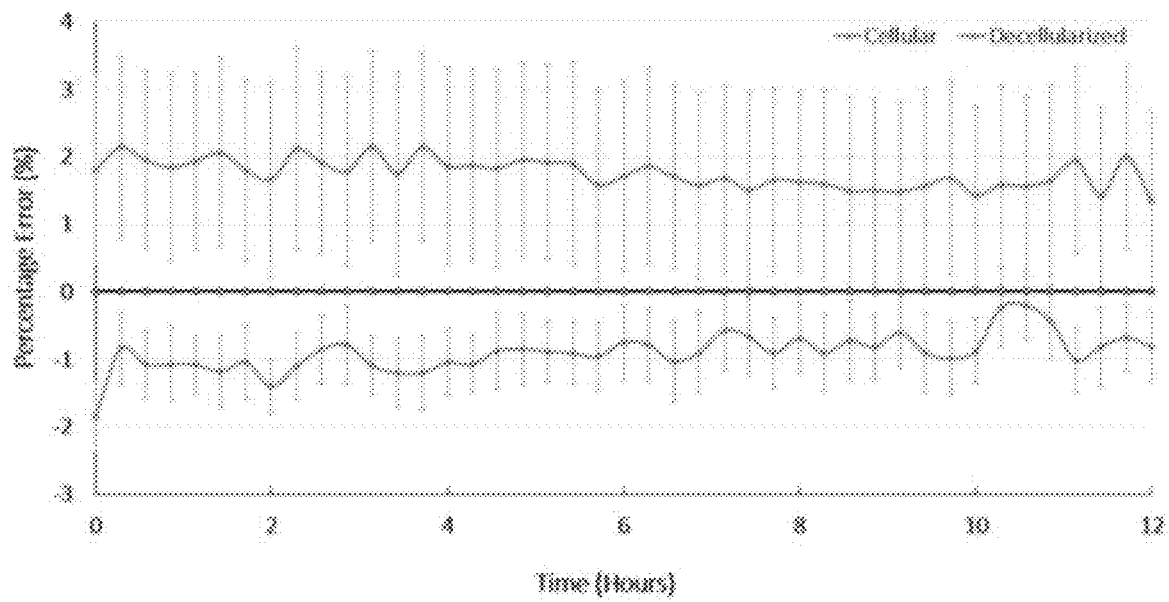
FIG. 31. GFs retention within hrECMs and ad hoc immunofluorescence analysis. Panel A shows the results of a semi-quantitative analysis of the protein expression profile of different GFs measured within the de-cellularized kidney (hrECMs) using a custom RayBio® Human Growth Factors Antibody Array G series 1. Average fluorescent intensity was obtained from duplicate signal intensities, adjusted to remove background and normalized to a positive control to account for differences among sub-arrays. As a general trend, important molecules like TGFβ, IGFII, members of the TGF family and VEGF family are retained within the decellularized matrix. Immunofluorescence for collagen V (B, 20×), vascular endothelial growth factor receptor 2 (VEGFR2, C, 20×) and Ve-Cadherin (D, 20×) demonstrate that the decellularized glomeruli maintain the presence of important fibrous protein (collagen V) as well as VEGFR2 and Ve-Cadherin that are necessary for endothelial cell attachment and function.
Figure 31:
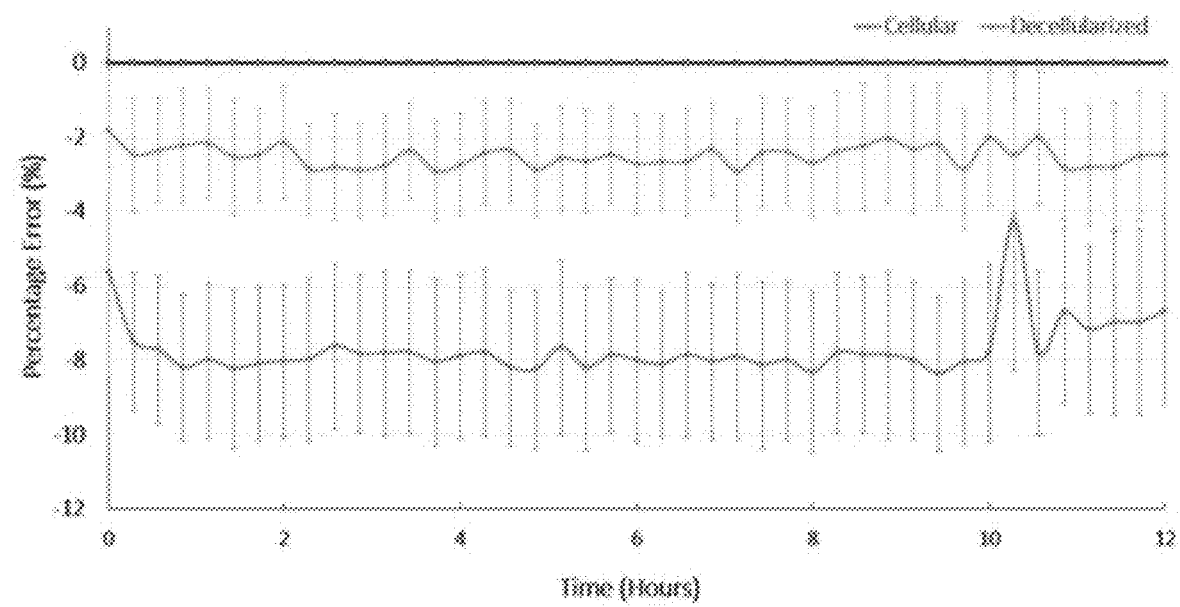

The multiplex array shows hrECMs retain numerous GFs that play vital role during important biological processes, including angiogenesis, renal development and regeneration, as well as glucose homeostasis (FIG. 31 and Table 2). Immunofluorescence confirmed the presence of collagen IV, VEGF-R2, as well as Ve-Cad (FIGS. 31B-D) within the hrECMs, indicating the preservation of the glomerular basement membrane and the presence of key molecules that support the capillaries structure within the glomeruli.

The present study was conceived and designed to address critical, yet unaddressed aspects of ECM characterization, namely the integrity and resilience of the innate vasculature through vessel morphometry and perfusion studies, and the ability of hrECMs to retain GFs through direct quantification of a custom-made panel of relevant GFs and ad hoc "in tissue" staining. The results show that the framework of the innate vasculature of hrECMs is well-preserved and retains its innate resilience, and that GFs that are key players in critical processes of tissue development like angiogenesis remain within the matrix post-de-cellularization at significant concentrations.

TABLE 2

| Human Growth Factors Array - Native kidney | | | | | | |
|---|---|---|---|---|---|---|
| AR | bFGF | b-NGF | EGF | EGF R | FGF-4 | FGF-6 |
| 438.10 ± 16.25 | 5585.10 ± 1363.04 | 462.70 ± 29.95 | 1576.10 ± 326.27 | 5360.30 ± 577.50 | 565.60 ± 20.19 | 54.10 ± 9.80 |
| FGF-7 | GCSF | GDNF | GM-CSF | HB-EGF | HGF | IGFBP-1 |
| 389.70 ± 16.25 | 499.80 ± 23.68 | 569.30 ± 29.04 | 402.90 ± 22.49 | 73.90 ± 10.36 | 16626.40 ± 3402.84 | 10023.00 ± 5834.07 |
| IGFBP-2 | IGFBP-3 | IGFBP-4 | IGFBP-6 | IGF-I | IGF-I SR | IGF-II |
| 2018.9 ± 555.18 | 21.3 ± 5.72 | 266.1 ± 12.27 | 266.5 ± 20.72 | 346 ± 40.67 | 497.9 ± 8.28 | 63180.1 ± 1964.59 |
| M-CSF | M-CSF R | NT-3 | NT-4 | PDGF R a | PDGF R b | PDGF-AA |
| 411.7 ± 161.93 | 523.1 ± 169.12 | 252.9 ± 11.33 | 469.3 ± 11.83 | 164.5 ± 12.02 | 433.7 ± 21.52 | 554.6 ± 48.24 |
| PDGF-AB | PDGF-BB | PlGF | SCF | SCF R | TGF-a | TGF-b |
| 984.2 ± 138.75 | 641.5 ± 170.89 | 281 ± 14.87 | 496.4 ± 68.47 | 386.5 ± 24.35 | 44.9 ± 11.85 | 4520.8 ± 391.55 |
| TGF-b 2 | TGF-b 3 | VEGF | VEGF R2 | VEGF R3 | VEGF-D | |
| 434.9 ± 10.63 | 125.3 ± 10.99 | 28.9 ± 9.62 | 855.4 ± 107.12 | 317 ± 29.87 | 185.8 ± 24.84 | |
| Human Growth Factors Array - Acellular kidney (hrECM) | | | | | | |
| AR | bFGF | b-NGF | EGF | EGF R | FGF-4 | FGF-6 |
| 753.6 ± 29.40 | 612.6 ± 50.56 | 654.3 ± 40.35 | 5948.5 ± 116.63 | 255.8 ± 37.50 | 1051.8 ± 140.84 | 277.2 ± 60.52 |
| FGF-7 | GCSF | GDNF | GM-CSF | HB-EGF | HGF | IGFBP-1 |
| 500.2 ± 22.03 | 732.2 ± 34.15 | 859.1 ± 35.39 | 503 ± 57.29 | 233.3 ± 36.17 | 802.6 ± 88.85 | 791.5 ± 78.59 |
| IGFBP-2 | IGFBP-3 | IGFBP-4 | IGFBP-6 | IGF-I | IGF-I SR | IGF-II |
| 582.9 ± 98.18 | 106.7 ± 16.00 | 502.9 ± 44.40 | 905.7 ± 184.62 | 483.5 ± 47.51 | 958.4 ± 131.08 | 17775.2 ± 4617.7 |
| M-CSF | M-CSF R | NT-3 | NT-4 | PDGF R a | PDGF R b | PDGF-AA |
| 235.9 ± 18.84 | 445.2 ± 47.80 | 785.2 ± 121.75 | 713.2 ± 29.28 | 80.3 ± 13.56 | 475.4 ± 47.61 | 746.8 ± 108.95 |
| PDGF-AB | PDGF-BB | PlGF | SCF | SCF R | TGF-a | TGF-b |
| 957.9 ± 97.99 | 490 ± 67.16 | 904.6 ± 148.18 | 876.3 ± 67.80 | 929.6 ± 110.23 | 268.6 ± 39.50 | 8322.7 ± 297.22 |
| TGF-b 2 | TGF-b 3 | VEGF | VEGF R2 | VEGF R3 | VEGF-D | |
| 611.8 ± 16.95 | 351.1 ± 32.06 | 78.8 ± 17.97 | 542.2 ± 51.91 | 586 ± 76.75 | 538.5 ± 150.54 | |

In regenerative medicine, CSST has shown the greatest potential for clinical translation, allowing the production of body parts bioengineered from patient's cells that were eventually implanted in more than 200 patients without any anastomosis to the recipient's vasculature, at the time of implantation. In contrast, more complex metabolic organs like the kidney do require re-anastomosis between the vascular pedicle of the bio-artificial organ and the recipient's bloodstream, to allow function. Therefore, the acellular framework of the innate vasculature endowed within ECM scaffolds used for tissue engineering purposes should maintain the basic characteristics and resilience of the intact counterpart, in order to allow implantation with physiological blood pressure being sustained in vivo. Moreover, as one of the critical functions of ECM in mammals is to act as reservoir for GFs to be released following specific stimuli[16], ECM scaffolds used for tissue engineering should maintain GFs. As hrECMs were proven to have the ability to induce the formation of new vessels in the in ovo[13] bioassay, there is evidence that several molecules involved in the inflammatory and angiogenesic cascades are present in the matrix post decellularization, demonstrating that the disclosed matrices are bioactive and so may facilitate the regeneration and re-building of new tissue after re-cellularization and ultimately implantation.

A morphometric study of the framework of the innate vasculature was conducted by three-dimensional analysis of SEM images of corrosion casting, as described by Pereira-Sampaio et al. and Manelli et al. Analysis and measurement of casting imaging at SEM revealed that morphology and dimensions of the acellular glomerulus and its vascular network are relatively well-preserved post-de-cellularization and are comparable to their cellular counterparts. The diameter and volume of the glomerular macrovasculature within the hrECMs were found to be contracted when compared with the normal kidney. This finding may be due to the absence of cells, accounting for a significant part of the whole volume of the intact, cellular glomerulus. No significant differences in the width of glomerular capillaries and the branching pattern and integrity of the larger vessels was detected. Overall, these data confirm the operability of the de-cellularization method yielding hrECMs that provide a framework of the vascular network preserved at all hierarchical levels, namely large vessel and small cortical vessels. The preservation of an intact vascular bed in the disclosed hrECMs is important because use of the innate scaffolds in vivo depends on an intact vascular network that is able to sustain physiological blood pressure and perfusion. With regard to the decreased glomerular diameter and volume observed in the disclosed matrices, it is reasonable to expect that the regeneration of the endothelium would normalize those values (i.e., bring them to values observed in the innate, cellular kidney).

As the kidney is one of the major control stations of intravascular blood pressure, experiments were designed to determine whether the intact framework of the vascular network of hrECMs maintains function and resilience, namely its ability to respond to changes in intravascular pressure. To do so, a state of the art technology was used that provided both a cardioemulating, physiologic pulse pressure and the ability to dynamically measure applied pressure and elastic vascular resistance for each pulse wave. Our analysis of pulse wave data and response to pressurization demonstrated that, although the process of de-cellularization removed cells, the scaffolds demonstrated the same elastic response characteristic of intact vascular beds. Specifically, scaffolds did not leak (no fluid wept from the surface) during perfusion and elastic rebound in response to an applied pulse wave was seen, although slightly diminished when compared to intact, cellularized kidneys.

To finalize the characterization of the matrices and determine whether they have the characteristic of implantable organs and induce formation of new vessels, the GFs content of hrECMs was examined. It is important to emphasize that, during kidney development as well as in the natural history of chronic kidney diseases, important GFs secreted and retained within the ECM orchestrate very complex cell-cell and cell-matrix interactions. For example, variation in concentration of several growth factors, including transforming growth factor-α (TGF-α), heparin-binding epidermal growth factor (HB-EGF), insulin-like growth factor (IGF), and fibroblast growth factor (FGF), are responsible for cell migration, proliferation, differentiation, induction of pro-fibrotic processes as well as possible pro-healing signaling with scar resolution[17]. Therefore, as GFs play a major role in determining progression or blockade of kidney damage, it is of vital importance to determine if the de-cellularization process of human kidneys preserves important stimuli that could eventually facilitate cellular repopulation and mediate induction of fibrosis, in future in vivo applications. Interestingly, several GFs, including TGF-α, FGF-6, insulin-like growth factor binding protein 3 (IGFBP-3), HB-EGF, insulin-like growth factor binding protein 6 (IGFBP-6), neurotrophin 3 (NT-3), placenta growth factor (P1GF), transforming growth factor-β (TGF-β), vascular endothelial growth factor (VEGF), and vascular endothelial growth factor-D (VEGF-D), were observed to be present within the hrECMs. The presence of critical transmembrane glycoproteins was confirmed, i.e., Ve-cadherin and VEGFR-2, which are vital for the function and the strength of the endothelium and for the maintenance of glomerular endothelial cells fenestrations, essential for glomerular barrier filtration. For example, VEGFR-2 postnatal deletion demonstrates a global defect in the glomerular microvasculature and the paracrine VEGF-VEGFR-2 signaling loop is identified as a critical component in the developing and in the filtering glomerulus[18]. The presence of these GFs should not be underestimated, showing that hrECMs provide not only structurally supportive vasculature, but also maintain architecturally specific transmembrane glycoproteins for glomerular endothelial cell function and support. Nevertheless, these data reveal, for the first time, that hrECMs are a candidate for tissue engineering purposes and possess all the necessary characteristics to induce functional vasculature in vivo.

The disclosed studies demonstrate that the framework of the innate vasculature of hrECMs is maintained at all hierarchical levels, is resilient, and can sustain intravascular pressures comparable to what is observed in normal physiology. Also, hrECMs retain numerous GFs that are necessary for the maintenance of endothelial cell homeostasis and function. These results establish that the scaffolds prepared as disclosed herein are useful in the regeneration of the cellular compartment and in vivo implantation of bioengineered renal organoids and organs for transplant purposes.

REFERENCES—FOR EXAMPLE 10 ONLY

1. Orlando G, Soker S, Stratta R J. Organ bioengineering and regeneration as the new Holy Grail of organ transplantation Ann Surg. 2013 August; 258(2):221-32.
2. Salvatori M, Peloso A, Katari R, Zambon J P, Soker S, Stratta R J, Orlando G. Semixenotransplantation: the regenerative medicine based-approach to immunosuppression-free transplantation and to meet the organ demand. Xenotransplantation, Jul. 8, 2014 ahead of print.
3. Ross E A, Williams M J, Hamazaki T, Terada N, Clapp W L, Adin C, et al. Embryonic stem cells proliferate and differentiate when seeded into kidney scaffolds. J Am Soc Nephrol 2009; 20:2338-47.
4. Orlando G, Farney A, Sullivan D C, AbouShwareb T, Iskandar S, Wood K J, et al. Production and implantation of renal extracellular matrix scaffolds from porcine kidneys as a platform for renal bioengineering investigations. Ann Surg 2012; 256:363-70.
5. Nakayama K H, Batchelder C A, Lee C I, Tarantal A F. Decellularized rhesus monkey kidney as a three-dimensional scaffold for renal tissue engineering. Tissue Eng Part A 2010; 16(7):2207-16.
6. Nakayama K H, Batchelder C A, Lee C I, Tarantal A F. Renal tissue engineering with decellularized rhesus monkey kidneys: age-related differences. Tissue Eng Part A 2011; 17(23-24):2891-901.
7. Nakayama K H, Lee C C, Batchelder C A, Tarantal A F. Tissue specificity of decellularized rhesus monkey kidney and lung scaffolds. PLoS One 2013; 8(5):e64134.
8. Sullivan D C, Mirmalek-Sani S H, Deegan D B, Baptista P M, Aboushwareb T, Atala A, Yoo J J. Decellularization methods of porcine kidneys for whole organ engineering using a highthroughput system. Biomaterials 2012; 33(31):7756-64.
9. Song J J, Guyette J P, Gilpin S E, Gonzalez G, Vacanti J P, Ott H C. Regeneration and experimental orthotopic transplantation of a bioengineered kidney. Nat Med 2013; 19(5):646-51.
10. Bonandrini B, Figliuzzi M, Papadimou E, Morigi M, Perico N, Casiraghi F, Dipl C, Sangalli F, Conti S, Benigni A, Remuzzi A, Remuzzi G. Recellularization of well-preserved acellular kidney scaffold using embryonic stem cells. Tissue Eng Part A 2014; 20(9-10):1486-98.
11. Wang Y, Bao J, Wu Q, Zhou Y, Li Y, Wu X, Shi Y, Li L, Bu H. Method for perfusion decellularization of porcine whole liver and kidney for use as a scaffold for clinical-scale bioengineering engrafts. Xenotransplantation. Oct. 7, 2014 [Epub ahead of print].
12. Choi S H, Chun S Y, Chae S Y, Kim J R, Oh S H, Chung S K, Lee J H, Song P H, Choi G S, Kim T H, Kwon T G. Development of a porcine renal extracellular matrix scaffold as a platform for kidney regeneration. J Biomed Mater Res A. Jul. 16, 2014 [Epub ahead of print].
13. Orlando G, Booth C L, Wang Z, Totonelli G, Ross C L, Moran E, Salvatori M, Maghsoudlou P, Turmaine M, Delario G, Al-Shraideh Y, Farooq U, Farney A C, Rogers J, Iskandar S S, Burns A, Marini F C, De Coppi P, Stratta R J, Soker S. Discarded human kidneys as a source of ECM scaffolds for kidney regeneration technologies. Biomaterials 2013; 34:5915-25.
14. Pereira-sampaio M A, Henry R W, Favorito L A, Sampaio F J. Cranial pole nephrectomy in the pig model: anatomic analysis of arterial injuries in tridimensional endocasts. J Endourol. 2012; 26(6):716-21.
15. Manelli A, Sangiorgi S, Binaghi E, Raspanti M. 3D analysis of SEM images of corrosion casting using adaptive stereo matching. Microsc Res Tech. 2007; 70(4):350-4.
16. Hynes R O. The extracellular matrix: not just pretty fibrils. Science. Nov. 27, 2009; 326(5957):1216-9.
17. Jain R K, Au P, Tam J, et al. Engineering vascularized tissue. Nat Biotechnol. 2005; 23(7):821-3.
18. Rahimi N, Kazlauskas A. A role for cadherin-5 in regulation of vascular endothelial growth factor receptor 2 activity in endothelial cells. Mol Biol Cell. 1999; 10:3401-3407.

EXAMPLE 11

Whole Organ Engineering—Re-Endothelialization of Liver Scaffolds

Donor shortage remains a continued challenge in liver transplantation. Recent advances in tissue engineering have provided the possibility of creating functional liver tissues as an alternative to donor organ transplantation. Small bioengineered liver constructs have been developed, however a major challenge in achieving functional bioengineered liver in vivo is the establishment of a functional vasculature within the scaffolds. Our overall goal is to bioengineer intact livers, suitable for transplantation, using acellular porcine liver scaffolds. We developed an effective method for reestablishing the vascular network within decellularized liver scaffolds by conjugating anti-endothelial cell antibodies to maximize coverage of the vessel walls with endothelial cells. This procedure resulted in uniform endothelial attachment throughout the liver vasculature extending to the capillary bed of the liver scaffold and greatly reduced platelet adhesion upon blood perfusion in vitro. The re-endothelialized livers, when transplanted to recipient pigs, were able to withstand physiological blood flow and maintained for up to 24 hours. This study demonstrates, for the first time, that vascularized bioengineered livers, of clinically relevant size, can be transplanted and maintained in vivo, and represents the first step towards generating engineered livers for transplantation to patients with end-stage liver failure.

Liver transplantation represents the only curative treatment for end-stage liver disease. Unfortunately this solution is limited by a critical shortage of donor organs that are suitable for transplant. According to the United Network for Organ Sharing, over 16,000 patients are currently awaiting liver transplant, while less than 7000 donor organs become available annually. This discrepancy between organ supply and demand results in thousands of deaths each year. Several treatment strategies are being developed to sustain critically ill patients until a time when a transplantable donor organ is available [1, 2]. However, these therapies can only buy a small amount of additional time for patients in liver failure. Recently, the use of non-heart-beating liver donors (NHBD) has been considered, but this would still not close the organ supply/demand gap [3-6]. Clearly, alternative treatments for patients with end stage liver disease need to be investigated. Over the past decade, the fields of regenerative medicine and tissue engineering have offered new strategies for the generation of engineered organs [7-9]. These new strategies are based upon the use of scaffolds with a preexisting architectural structure that are seeded with an appropriate population of cells [10]. Natural tissue extracellular matrices (ECM) possess a dynamic network of macromolecules with organ-specific anatomical and biochemical properties [11, 12]. It would be advantageous to include these properties in any scaffold considered for organ engineering.

Whole organ engineering represents the ultimate solution for completely solving the shortage of transplantable organs [13-20]. For the reasons mentioned above, decellularized whole organ matrices would be the preferred option for a construct scaffold. These scaffolds are easily generated by perfusion of donor organs with mild detergents that remove the cellular components from the organ [21, 22]. Importantly, decellularized whole organ matrices retain the vascular network and tissue microarchitecture present in the native organ [23, 24]. The current study is based on the development of a decellularized liver scaffold that is subsequently repopulated with cells isolated from liver tissue samples. The ultimate goal of these studies is to create a transplantable organ that could replace the functional capabilities of the patient's failing liver [25, 26].

The decellularization process for the production of an acellular organ scaffold has been under development for many years, and the results have been quite remarkable [20, 21]. However, the recellularization process has proven to be very challenging. One critical obstacle to achieving a transplantable, recellularized organ is reestablishment of a patent vasculature with sufficient endothelial cell coverage to prevent thrombosis. Acellular ECM is potently thrombogenic, and blood clots will form in an insufficiently endothelialized construct, even with the use of standard anticoagulant therapy [27].

Figure 32:
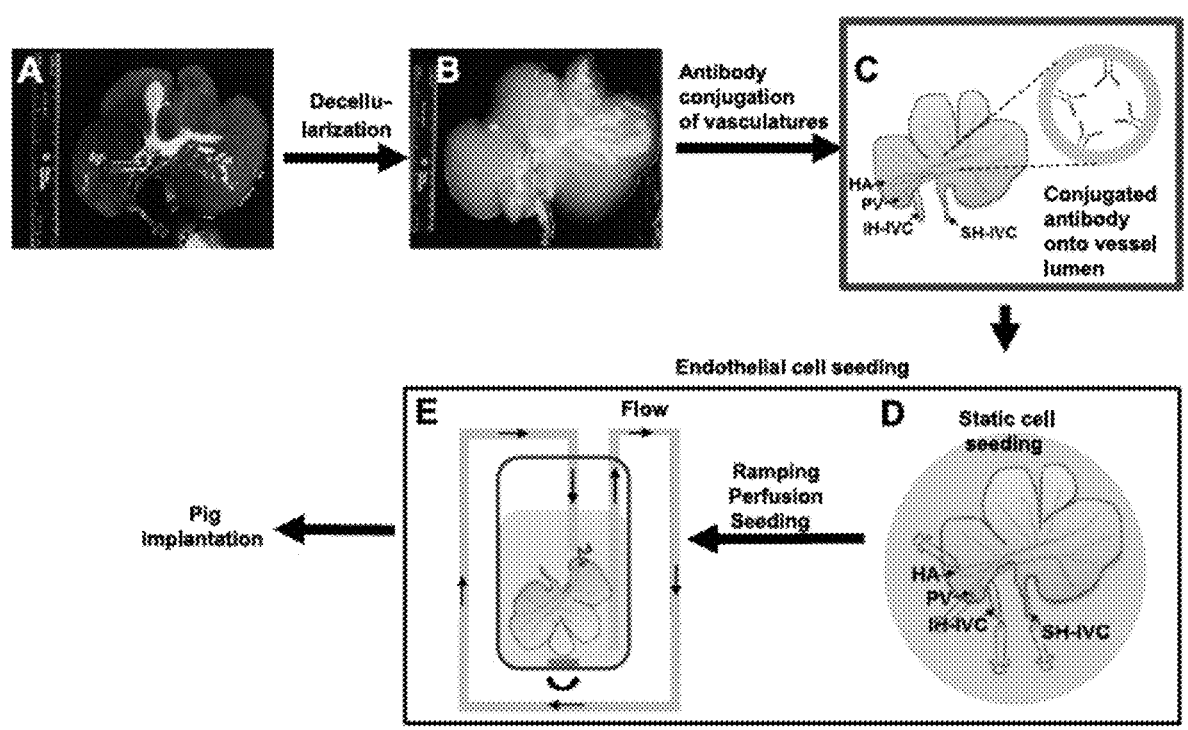
FIG. 32. Schematic diagram of the re-endothelialization processes for decellularized pig liver scaffolds. (A) Native liver harvested from piglets was decellularized using 1% 2-[14-(2,4,4-trimethylpentan-2-yl)phenoxy]ethanol (Triton X100) to obtain a completely decellularized liver scaffold (B). Following antibody conjugation on vasculatures of the liver scaffold (C), the antibody-conjugated scaffold was seeded with endothelial cells (MS1) using a combination of static (D) and perfusion methods (E), and then matured in a bioreactor system. The engineered liver construct was implanted into pigs. PV, HA, SH-IVC, and IH-IVC indicates portal vein, hepatic artery, suprahepatic inferior Vena Cava, and intrahepatic inferior Vena Cava, respectively.

The goal of the current study was to re-establish a functional vasculature in bioengineered livers of clinically relevant size. To achieve this goal, we developed a novel re-endothelialization technique based on using anti endothelial cell antibodies to stabilize seeded cells on the vessel walls. Vascular functionality was validated by transplanting the re-endothelialized livers using a heterotopic transplantation model with inflow from the renal artery and the outflow to the renal vein (FIG. 32). The major findings indicated that the re-endothelialized liver scaffolds were able to withstand physiologic blood pressure and maintain blood flow within the bioengineered livers for 24 hours. This study shows, for the first time, a strategy for overcoming a major hurdle in the engineering of transplantable liver, the establishment of functional vasculature.

Decellularization of Porcine Liver

Native livers were harvested from 5 to 8 kg piglets. The portal vein (PV), common hepatic artery (HA), suprahepatic (SH)- and infrahepatic (IH) inferior vena cava (IVC) were cannulated with smart site connectors (Cole Parmer) attached to 14 G tubing with inflow and outflow adjusted to mimic normal flow through the organ. Detergent solutions (1% 2-[4-(2,4,4-trimethylpentan-2-yl)phenoxy]ethanol (Triton X-100) and 0.1% ammonium hydroxide in distilled water) were perfused into the liver tissue using a peristaltic pump (Master flex L/S with Master flex L/S easy load pump head, Cole Parmer, Vernon Hills, Ill., USA). Decellularization of the liver was performed by perfusing the organ at a flow rate of 0.5 ml/min for 2-3 days, followed by washing with saline for 3-4 days. The decellarized livers were sterilized by gamma irradiation at 1.2 MRad (12,000 Gy) prior to cell seeding.

Characterization of Acellular Liver Scaffold

To evaluate the efficiency of scaffold decellularization, DNA quantification and histological analysis (H&E) were performed. For DNA quantification, samples were excised from representative lobes of native and decellularized livers. The samples were minced and lyophilized in preparation for analysis (Labconco, Kansas City, Mo.). DNA was extracted from 5 mg samples using the Qiagen DNeasy Blood and Tissue Kit (Qiagen Inc., Valencia, Calif.) and quantified using Quant-iT PicoGreen (Invitrogen Corp., Carlsbad, Calif.). Fluorescence from the PicoGreen signal indicates residual DNA and was measured at 525 nm (excitation 490 nm) using a SpectraMax M5 Multi-Mode Microplate Reader (Molecular Devices Inc., Sunnyvale, Calif., US).

To evaluate the maintenance of vasculatures within the decellularized liver scaffold, angiographic studies were performed using computed tomography (CT) and liver vascular casting combined with electron microscopic analysis. For CT imaging of native and decellularized liver scaffold, a CT contrast agent (MICROFIL, Flowtech, Inc., Carver Mass.) was infused through the PV at 1 ml/min flow rate, while the artery and veins were clamped. The livers were scanned on a Toshiba Aquilion 32 CT scanner (Toshiba America Medical Systems, Inc., Tustin, Calif.) and analyzed with CT angiography body and soft tissue deformation processing algorithms. Imaging was conducted using a TeraRecon Aquarius Workstation (TeraRecon Inc., Foster City, Calif.).

Liver casts were prepared using Batson's compound no 17 (Polysciences Inc., Warrington, Pa.) injected through the portal vein with constant flow rate (1 ml/min) using a syringe pump (New Era Pump Systems, Inc., Farmingdale, N.Y., USA). Following the resin injection, the infused liver was incubated to allow the polymerization within the liver vascular system. After curing, the liver tissue was digested with 20% sodium hydroxide at 37° C., followed by washing with deionized water. The vasculatures of the liver cast were imaged using scanning electronic microscopy (SEM). The cast segments were mounted on silver plates, sputter coated with gold and imaged at 15 KV.

Re-Endothelialization of Acellular Liver Scaffold

To improve re-endothelialization of vasculatures within the liver scaffold, rat anti-mouse CD31 antibody (BD sciences, Franklin Lakes, N.J.) was conjugated to the acellular liver scaffold. Liver scaffolds were treated with a solution of 1-Ethyl-3-[3-dimethylaminopropyl] carbodiimide hydrochloride (EDC) (Sigma Aldrich) and Nhydroxysuccinimide esters (NHS) (SigmaeAldrich) in phosphate buffered solution (PBS) for 30 minutes. Subsequently, 20 ml of a 50 mg/mL antibody solution was injected through the artery and veins, followed by incubation for 2 hours at room temperature. Constructs were washed by perfusion with PBS to remove unreacted antibodies and small pieces of the antibody-conjugated constructs were embedded into OCT compound for preparation of frozen blocks, followed by sectioning of the frozen blocks. CD31 antibody conjugation on the vasculatures within the sections was confirmed by treatment with Alexa588 goat anti-rat antibody (BD Biosciences). The conjugated antibody was semi-quantified by imaging three randomly selected areas (n=3 livers per group) with a fluorescence microscope (Leica). Fluorescence intensity was determined using Image J software. For re-endothelialization of the antibody-conjugated liver scaffold, vascular endothelial cells expressing GFP protein (MS1) were used. MS1 seeding was performed using a two-step process: a) static and b) perfusion (FIG. 32). For static cell seeding, 7, 3, 5, and 5 ml of $10 \times 10^6$/ml MS1 cells suspended in DMEM-high glucose medium (Invitrogen Life Technologies, Carlsbad, Calif.) supplemented with 10% FBS (Invitrogen Life Technologies) were infused into PV, HA, SH-IVC, and IH-IVC, respectively. The seeded cells were then allowed to attach for 1 hour, followed by another 1-hour infusion performed following a 180-degree rotation of the liver scaffold from the original position. This allows for a more even distribution of cells within the construct. Following the static seeding, the liver scaffold was connected to a bioreactor system and equilibrated in 10% FBS DMEM medium at 1 ml/min overnight. Perfusion bioreactors consisted of a glass chamber for the liver, with media circulation via platinum-cured silicone tubing (Cole-Parmer, L/S 15) using Cole-Parmer Digital Drive peristaltic pumps. Bioreactors contained 1.5 L of growth medium and were maintained in humidified conditions at 37° C., supplemented with 5% $CO_2$. Media was perfused directly into the liver via the PV under constant stirring via a magnetic stirrer. For perfusion cell seeding, 5 ml of a suspension of $10 \times 10^6$/ml cell perfused through the PV at 3 ml/minute. The flow rate was gradually increased to 5 and 10 ml/minute at 10-12 hour intervals, and maintained at 10 ml/minute for 3 days. After the perfusion culture, several MS1 seeded liver scaffolds were fixed in 10% formalin, embedded in OCT compound, and processed for histological analysis (H&E and DAPI nuclear staining). Efficiency of re-endothelialization of the acellular liver scaffold was determined by histological analysis [H&E staining and fluorescent imaging (GFP and DAPI)] as well as SEM.

In vitro Functional Testing Of Re-Endothelialization

To determine the functionality of the re-endothelialized liver vasculature, MS1-seeded scaffolds were perfused with freshly collected heparinized porcine blood for 1 hour. The blood perfusate was prepared by diluting whole blood at a 3:1 ratio in Kreb's bicarbonate buffer. Unseeded scaffolds were used as controls. To determine platelet adhesion on the scaffolds, paraffin sections were stained with an anti-integrin aIIb antibody (Santa Cruz Biotechnology Inc., Santa Cruz, Calif.) and Alexa 647-conjugated, rabbit anti-goat antibody (Invitrogen Life Technologies), followed by visualization by confocal microscopy (LSM5, Zeiss). The levels of platelets adhered onto vessel walls were quantified using the confocal images from representative regions of the vasculatures (4 random areas, n=3 livers per group) from within the liver parenchyma by measuring the fluorescence intensity using Image J software. The fluorescence intensities were averaged, and then represented as mean±SD.

In vivo Implantation Study

Yorkshire pigs (female, 60e80 kg) were used for the in vivo animal study. All surgical procedures were performed in accordance with the Institutional Animal Care and Use Committee (IACUC) approved protocols. Recipient animals were partitioned into two different groups: i) decellularized liver scaffold without further treatments, n=3 animals and ii) re-endothelialized liver, n=3 animals. The implantation protocol was similar to that developed in our previous study [27]. Briefly, animals were placed in a supine position. The surgical site was disinfected, and an intravenous catheter was placed to allow for fluid replacement and drug delivery during surgery. Cardiopulmonary function was monitored throughout the procedure. Under general anesthesia, a midline abdominal incision was made through the skin and muscle. The abdominal aorta and inferior vena cava just above the iliac bifurcation were identified and dissected from the surrounding tissue. After placing a large Satinsky clamp on the renal artery and renal vein, the portal vein and IH-IVC of the liver scaffold were anastomosed to the aorta and inferior vena cava in an end-to-side fashion using double-armed 6/0 prolene sutures. After reperfusion, the blood flow through the artery and vein of the implanted scaffold was monitored with Color Doppler ultrasonography (Acuson Sequola 512, Simens).

Characterization of the Harvested Liver

At 1 day after implantation, vascular patency in the implanted liver scaffold from the animals was examined by ultrasound imaging and radiographic fluoroscopy using Siemens SIREMOBIL Compact L C-arm (Siemens, Munich, Bavaria, Germany). Conray contrast agent (iothalamate meglumine) (Mallinckrodt Inc., St Louis, Mo.) for the fluoroscopic angiogram was injected through the renal artery. After euthanization, the retrieved liver scaffold was examined by histological (H&E) and immunohistochemical (platelet immunostaining) analysis. For quantification of platelet adhesion, aIIb+platelet fluorescence intensity was obtained from randomly selected images (four per liver from the portal vein branch and central vein). Fluorescence intensity was calculated from the values (total fluorescence intensity/area)] of each fluorescent image using Image J software. The data was represented as mean±SD.

Statistics

Student t-test analysis was used for statistical analyses. Differences were considered significant at P<0.05.

Preparation and Characterization of Acellular Porcine Liver Scaffolds

Figure 33:
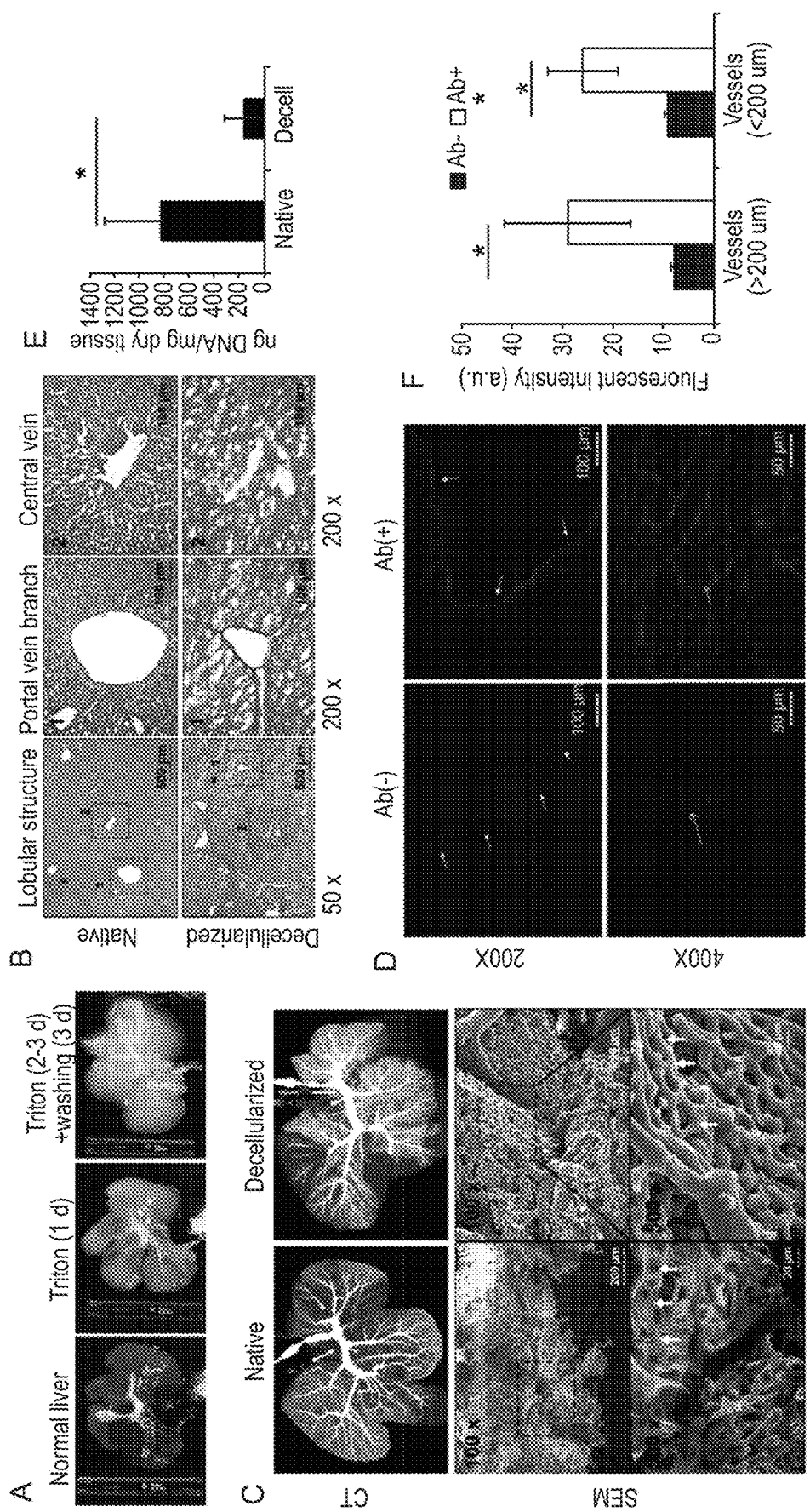
FIG. 33. Preparation of implantable porcine liver scaffold. (A) Gross images of porcine liver decellularization, Ruler scale: 15 cm. (B) Evidence of decellularization of normal porcine liver (H&E staining and residual DNA quantification). Acellular liver scaffolds have no cellular components visible in the portal vein branch and central vein as well as within lobular structures. (E) The quantification of residual DNA showed significant reduction in DNA as compared to that of native liver (n=3 liver scaffolds per group, Student t-test, $P<0.05$). (C) Maintenance of intact and functional vasculatures within the decellularized porcine liver scaffold by CT imaging and vascular casting followed by SEM analysis. CT images indicate intact vasculatures throughout entire lobes of the decellularized liver scaffold. SEM analyses of liver casts demonstrate functional vasculatures. Note the sinusoid-like structures (arrows in the images of ×500). (D) Antibody conjugation onto vasculatures within the liver scaffold. CD31 antibody conjugation was confirmed by positive fluorescence derived from fluorescently labeled secondary antibody. (F) Quantitative results of antibody conjugation showed significant statistical difference in blood vessels of various sizes (Student t-test, $P<0.05$, n=3 liver scaffolds per group). Six large (>200 mm) and three small (<200 mm) blood vessels per scaffold were selected for the quantification.

Perfusion of the decellularization reagent through the portal vein (PV) and hepatic artery (HA) resulted in a gradual color change to white after 1 day, indicating progressive removal of the cellular components within the liver scaffold (FIG. 33A). To evaluate the efficacy of decellularization, histological analysis and DNA quantifications were performed (FIG. 33B). Histological analysis showed that the decellularized scaffold contains no cellular materials at the PV branch and central vein as well as within the liver parenchyma (H&E). Quantification of residual DNA within the liver scaffold indicated a significant reduction as compared to native liver (P<0.05).

To determine the preservation of intact vasculatures within the acellular liver scaffolds, CT angiographic analysis and vascular casting in combination with scanning electronic microscopy (SEM) were performed (FIG. 33C). CT images of the native and decellularized liver scaffolds demonstrate intact vasculatures throughout the lobes of the scaffolds. Additionally, liver vascular casting showed preservation of a functional vascular network within the scaffolds that is capable of allowing efficient perfusion through the entire construct. Importantly, SEM analysis of the liver vascular casts showed intact lobular structures (arrows) within the native and decellularized liver casts, indicating maintenance of an intact capillary bed within parenchymal lobules.

Figure 34:
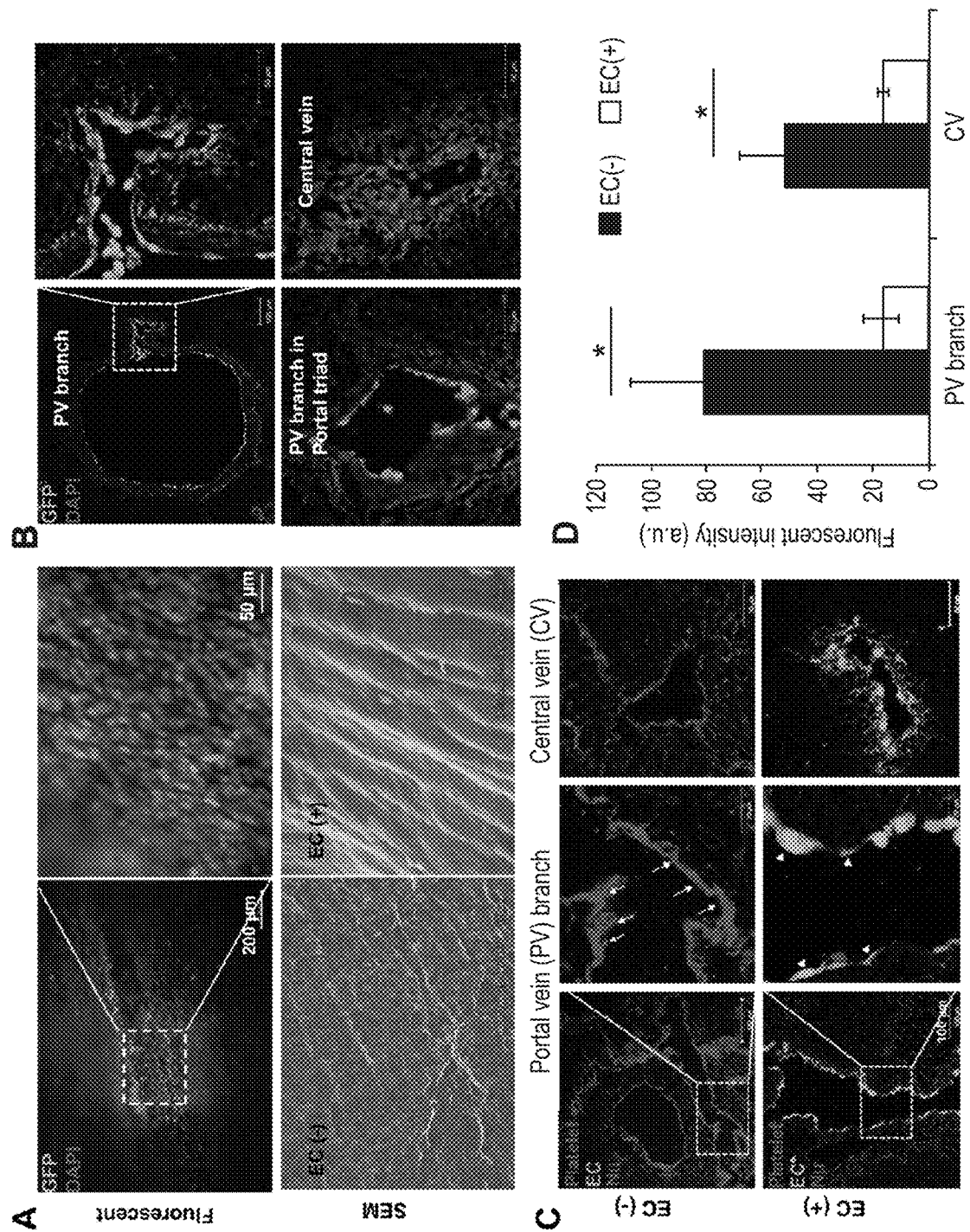
FIG. 34. Structural and functional re-endothelialization of acellular liver scaffolds. (A) Homogenous and well-oriented re-endothelialization of the portal vein (PV) of the decellularized liver scaffold, confirmed by GFP expression and SEM analysis on attached MS1 cells, respectively. (B) Efficient re-endothelialization at the portal triad and central vein (GFP/DAPI staining). (C) Functional re-endothelialization on the vasculature. Blood perfusion of liver scaffolds results in significant levels of platelet adhesion (aIIb positive staining) on the vasculatures of the unseeded scaffold ($EC^-$) indicated by arrows (severe platelet adhesion), while endothelial cell attachment (arrowheads) was significantly reduced in the $EC^+$ scaffolds. Quantitatively, re-endothelialization of liver scaffolds ($EC^+$) significantly reduced platelet adhesion as compared with that of scaffold only. The quantitative results showed significant statistical difference (Student t-test, $P<0.05$, n=3 liver scaffolds per group, four areas from PV and CV per scaffold).

Re-Endothelialization of the Liver Scaffold and Structural and Functional Characterization Homogenous and functional re-endothelialized vasculatures within the decellularized porcine liver scaffolds are critical for establishment of vascular patency. To enhance the attachment of endothelial cells and prevent detachment under physiologic flow conditions, CD31 antibodies were conjugated onto the vascular surfaces, as confirmed by imaging of a fluorescently labeled secondary antibody. The images clearly showed increased fluorescence intensity in antibody-conjugated vasculatures as compared with the unconjugated constructs. This indicated efficient antibody conjugation onto vasculatures of the decellularized scaffolds. The statistical difference was significant in vessels of varying diameters (Student t-test, P<0.05) (FIG. 33D). For re-endothelialization of acellular liver scaffolds, murine endothelial cells (MS1) were seeded onto the scaffold using a combination of static and perfusion techniques. Results from fluorescence imaging and SEM analysis demonstrated that the MS1 cells expressing GFP are intact, well-aligned, and uniformly distributed over the lumen of large vessels (FIG. 34A). Efficient re-endothelialization was also observed on intrahepatic vessels such as PV branches and central veins within portal triads (FIG. 34B). Based on the GFP fluorescence imaging, 80-90% of the extracapillary vasculature, including the portal vein (PV), inferior Vena Cava (IVC), PV branches, and central vein (CV) branches, are covered by endothelial cells.

To determine whether the seeded liver scaffolds are functional, heparinized pig whole blood was perfused through the PV. It was expected that the functional re-endothelialization of vasculatures would reduce platelet adhesion in re-endothelialized liver scaffolds during blood perfusion. After blood perfusion in vitro, the effect of re-endothelialization was determined by immunostaining with integrin aIIb antibodies on unseeded and seeded liver matrices. A minimal number of integrin aIIb+platelets were found on the portal vein and central vein of the re-endothelialized liver scaffolds [EC(+)], whereas high levels of platelet accumulation were observed in the EC(−) livers (FIG. 34C). Quantitatively, the portal vein and central vein of EC+livers showed significantly reduced platelet adhesion. This reduction was 3-4 fold compared to EC$^-$ livers (FIG. 34C, Student t-test, P<0.05). Quantification of platelet adhesion by measurement of fluorescence intensity showed a significant decrease in platelet adhesion in the seeded scaffolds (FIG. 34C). These results indicate that endothelial cell seeding of the acellular porcine liver scaffold results in formation of a uniform and functional endothelial layer inside the vascular remnant lumens.

Implantation of Engineered Porcine Liver Construct

Figure 35:
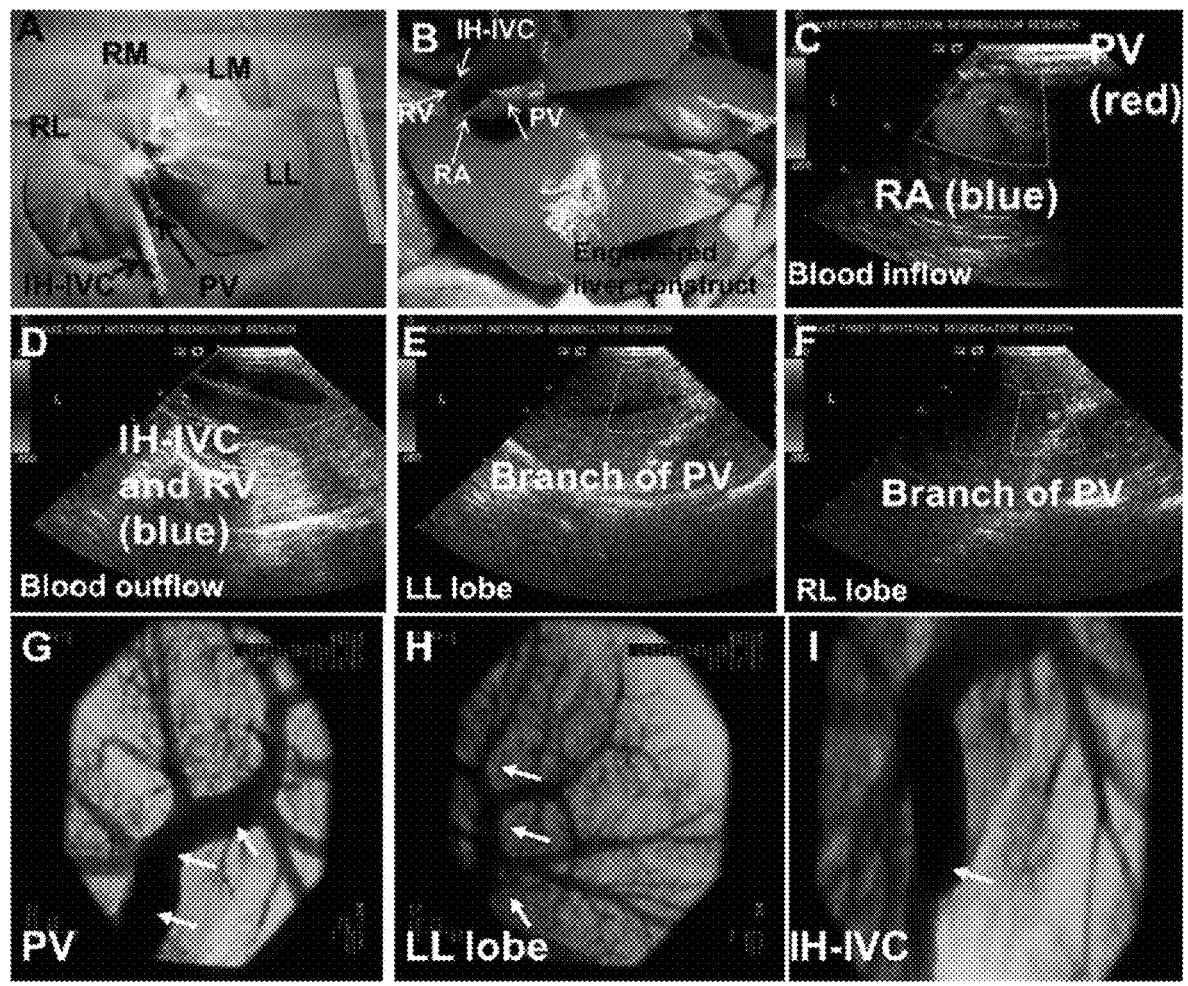
FIG. 35. In vivo implantation of engineered porcine liver constructs into pigs. (A) The engineered liver construct was heterotopically implanted into pigs (B) and showed good blood flow through the entire liver implant, as confirmed by ultrasound imaging at the anastomosis sites of (C) renal artery (RA) and portal vein (PV), (D) infrahepatic (IH)-IVC and renal vein (RV), and each lobe [(E) LL and (F) RL lobe)]. At 4 hours after implantation, the engineered liver implant demonstrated vascular patency, as evidenced by fluoroscopic angiography (GeI). LL and RL represents left and right lateral lobe, respectively.

To test the feasibility of implanting a clinical-scale bioengineered liver, liver constructs (FIG. 35A) were heterotopically implanted into pigs by vascular anastomosis following a left nephrectomy (FIG. 35B). The blood flow and vascular patency were determined by ultrasound and angiography. Following implantation, all liver constructs showed good blood flow within the liver constructs, as confirmed by ultrasound images of blood inflow through the renal artery/portal vein (RA/PV) anastomosis (FIG. 35C), outflow through the intrahepatic-inferior vena cava/renal vein (IH-IVC/RV) anastomosis (FIG. 35D), and flow through the branches of the PV within the left lateral (LL) (FIG. 35E) and right lateral (RL) lobes (FIG. 35F). Results from the fluoroscopic angiography studies confirmed vascular patency through the PV, left lateral (LL) lobe, and IH-IVC heparinized as indicated by the arrows (FIGS. 35G-I).

Figure 36:
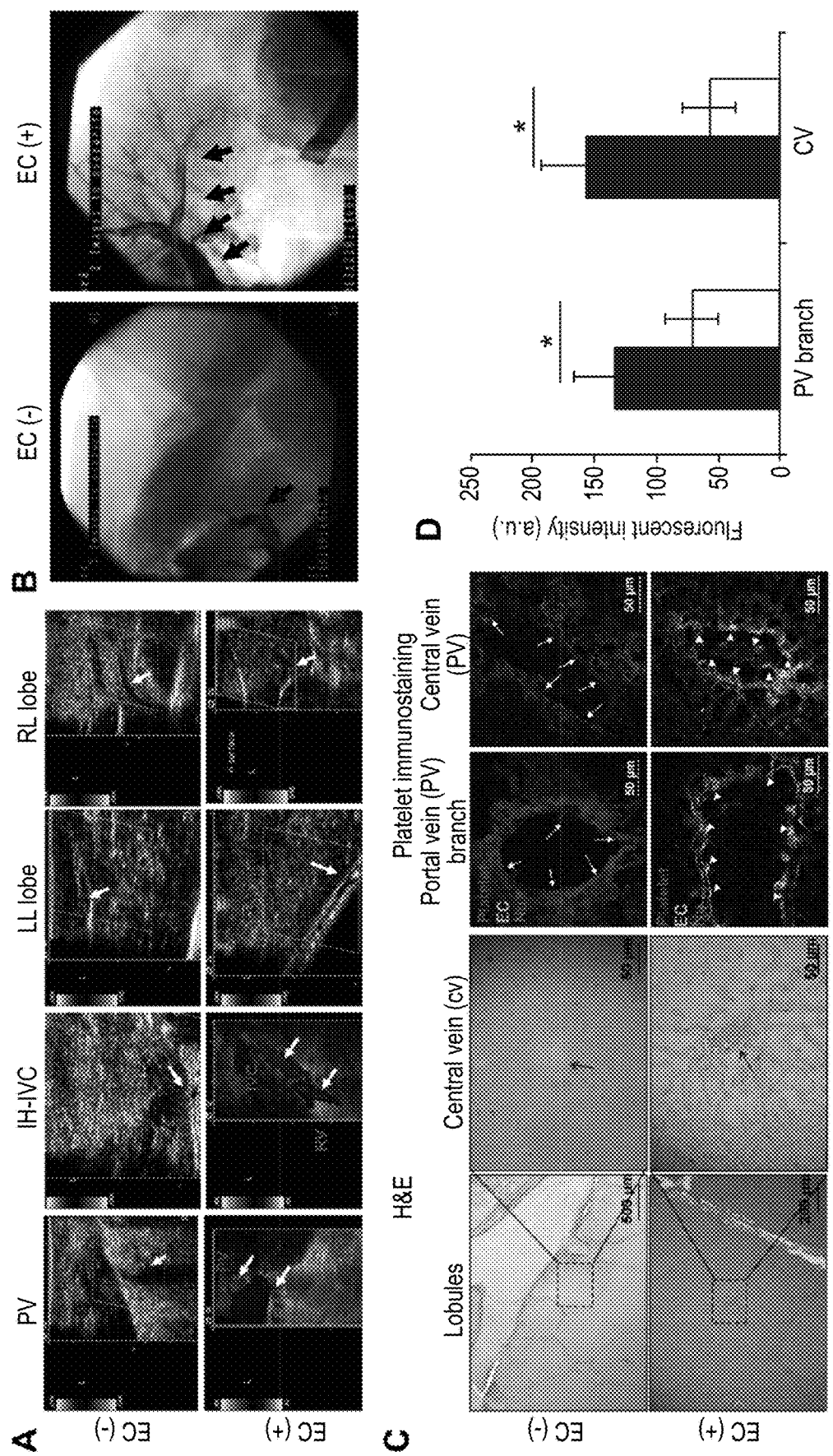
FIG. 36. Improved vascular patency by re-endothelialization of the liver scaffold. At one day post-implantation, re-endothelialization of vasculatures within the implant maintained vascular patency as compared with that of scaffold only, as confirmed by (A) ultrasound imaging as well as (B) fluoroscopic angiography. (C) Results of H&E and immunostaining for platelet adhesion demonstrate that MS1 attachment (arrowhead) on the vasculature significantly reduced platelet adhesion onto vessel walls of the re-endothelialized implants compared with that on scaffold only (arrows). The quantitative results showed significant statistical difference (Student t-test, $P<0.05$, n=3 liver scaffolds per group, four areas from PV and CV per scaffold).

At one day post-implantation, results from vascular imaging demonstrated that the re-endothelialized liver constructs continued to maintain good blood flow and vascular patency as compared to the unseeded scaffolds (FIGS. 36A-B). Ultrasound imaging (FIG. 36A) of the unseeded scaffolds (EC$^-$) showed the absence of blood flow into the liver implant; while the imaging of constructs from the EC$^+$ group showed a significant blood flow into the portal system along with good outflow from the RV. Additionally, a significant blood flow within the liver parenchyma (LL and RL lobe) was noted in the EC$^+$ constructs as compared to the acellular scaffolds.

As expected, significant differences in terms of vascular patency were observed between the unseeded and re-endothelialized groups (FIG. 36B). The unseeded liver implants showed a complete absence of vascular patency. During direct injection of contrast media into the portal vein (PV) for fluoroscopic angiography, a very strong resistance was noted, which was likely due to the complete clotting of the entire portal system. While flow into some main PV branches was detectable, the entire parenchyma was obstructed by blood clots. In contrast, the constructs from the EC$^+$ groups demonstrated maintenance of the native geometrical vessel hierarchy as visualized by the injected contrast agent (arrows), indicating that these vascular networks maintained patency. The EC$^-$ group displayed vascular patency only inside the main portal branches, with irregular and scattered diffusion of the contrast medium within the construct. However, constructs from the EC$^+$ group showed a homogeneous distribution of the contrast agent from the hilar zone to peripheral regions of each lobe. The maintenance of vascular patency was accompanied by the presence of endothelial cells within the vasculatures of the implant (FIG. 36C), which resulted in the reduction of platelet adhesion on the vessel walls. Quantification of platelet adhesion showed a significant difference between the EC$^-$ and EC$^+$ groups (Student t-test, P<0.05).

Production of bioengineered livers for transplantation into patients undergoing liver failure would have an enormous impact on the healthcare field, as this technology could alleviate the current problem of donor organ shortage [26]. Successful generation of bioengineered tissues with simpler structures have been achieved to date, including blood vessels [28], bladder [29] and upper airways segments [30]. However, engineering of complex, solid organs such as kidney and liver pose several additional challenges that must be met before they can be employed clinically. One major obstacle in creating an engineered functional solid organ is reestablishment of the organ's vasculature to a degree that is capable of 1) withstanding physiological blood flow conditions, 2) preventing thrombosis, and 3) able to deliver blood to the entire organ's volume. In the current study, this challenge was overcome with the results showing that re-endothelialized liver scaffolds were able to withstand physiologic blood pressure and maintain blood flow within the bioengineered livers for 24 hours.

Prevention of thrombosis requires coverage of the vascular lumen by endothelial cells in order to prevent platelet adherence to vessel wall. In the current study, successful re-endothelialization of the vasculatures of decellularized liver matrices was demonstrated (FIG. 32). An antibody conjugation technique was employed in order to enhance endothelial cell adhesion during in vitro maturation of the construct, and following implantation in vivo. In our previous study using acellular porcine kidney scaffolds [31], we confirmed effectiveness of CD31 antibody conjugation by demonstrating that antibody conjugation-mediated endothelial cell attachment on the vasculature of implanted scaffolds improved vascular patency throughout the renal matrix, when compared to the re-endothelialized scaffolds without antibody conjugation. In a similar way, for this liver study, the antibody conjugation method was used for better maintenance of re-endothelialization of the engineered liver construct during in vivo implantation. As expected, efficient re-endothelialization via the CD31 antibody conjugation of bioengineered livers prevented thrombosis under normal physiological vascular conditions. While reendothelialization using anti-CD31 antibody conjugation reinforces endothelial cell attachment to the vascular surfaces, it may also be possible to co-conjugate anti-thrombotic agents, such as heparin, to further minimize the potential for thrombosis and allow additional time for maturation of the vasculature in vivo.

The porcine transplant model was chosen for this study in order to validate the function of the reestablished vasculature under clinically relevant conditions. Furthermore, a large animal model for bioengineered organ transplantation represents a significant scale-up of this technology from published studies using rodents [19]. In terms of size, our engineered porcine liver constructs measure approximately 15-20 cm (FIG. 33A) in diameter, which is comparable to that of human liver [greatest transverse (20-22.5 cm), vertical (15-17.5), and greatest antero-posterior diameter (10-12.5 cm) measurement] [32]. The combined hepatic blood flow rate through the portal vein and hepatic artery is approximately 700 ml/min [33]. Maintaining flow through the transplanted construct for 24 hours indicates the potential for handling up to 1000 L of blood over this time frame.

This is the first report that demonstrates implantation of a vascularized liver construct of clinically relevant scale. This finding leads to the expectation that the technology will be useful in humans.

Vessel casting of decellularized livers demonstrated that the sinusoidal basement membrane within the lobular structures is capable of retaining the casting resin. This finding was further supported by histological analysis that confirmed re-endothelialization extending to the capillary bed of the construct.

These data indicate that complete re-endothelialization of a large-scale liver construct is possible and has been achieved. Fluoroscopic angiography showed that the level of re-endothelialization achieved in the current study was sufficient to withstand physiological blood flow conditions for up to 24 hours. This finding is consistent with the Doppler ultrasound data, which measured blood flow within the transplanted construct throughout the 24-hour period. These cumulative findings indicate that re-endothelialized liver constructs have the potential to support a hepatic parenchyma for extended periods of time, in an in vivo model of clinically relevant scale. This finding establishes that the technology disclosed herein allows for the physiological perfusion of bioengineered large organs such as liver, kidney and pancreas (see Example 12) in order to ensure viability and function of the parenchymal cells. In the current study, seeded liver constructs were allowed to partially mature in a perfusion bioreactor for three days. However, further maturation and remodeling of the construct would be expected following transplantation in vivo.

Previous studies by our group indicate that decellularized liver matrices are a suitable scaffold to support cell phenotypes found in the liver parenchyma, including mature hepatocytes [19, 34, 35]. However, for these parenchymal cells to remain viable within the construct, an unobstructed blood flow to these cells must be maintained. The data presented here represent a significant step towards this end. While cells isolated from cadaveric livers deemed unsuitable for transplant represent one potential parenchymal cell source, a construct engineered using these cells would still carry with it the requirement for immunosuppression following transplant. Recent advances in the field of induced pluripotent stem cells (iPS) provide a potential autologous cell source for whole-organ engineering. These cells have also been shown to possess significant capacity for in vitro expansion, meaning that a number of cells sufficient for construct seeding may be obtained from a small population of iPS derived hepatocytes [36].

In conclusion, we have demonstrated for the first time the feasibility to generate natural porcine liver ECM scaffolds with an intact vascular network extending to the capillary bed, which is sufficient to prevent thrombosis within the liver construct for a period of 24 hours following transplantation. Furthermore, we have accomplished these advances in pigs, which represent a clinically relevant scale. These findings demonstrate the feasibility of engineering a whole liver vasculature that would allow integration into the circulatory system to support a bioengineered liver long-term. We see this as a necessary first step towards the generation of an engineered liver for the treatment of end stage liver disease.

REFERENCES—FOR EXAMPLE 11 ONLY

[1] Mitzner S R, Stange J, Klammt S, Koball S, Hickstein H, Reisinger E C. Albumin dialysis MARS: knowledge from 10 years of clinical investigation. ASAIO J 2009; 55:498-502.

[2] Donati G, La Manna G, Cianciolo G, Grandinetti V, Carretta E, Cappuccilli M, et al. Extracorporeal detoxification for hepatic failure using molecular adsorbent recirculating system: depurative efficiency and clinical results in a longterm follow-up. Artif Organs 2014; 38:125-34.

[3] Abt P L, Desai N M, Crawford M D, Forman L M, Markmann J W, Olthoff K M, et al. Survival following liver transplantation from non-heart-beating donors. Ann Surg 2004; 239:87-92.

[4] Perera M T, Bramhall S R. Current status and recent advances of liver transplantation from donation after cardiac death. World J Gastrointest Surg 2011; 3:167-76.

[5] Casavilla A, Ramirez C, Shapiro R, Nghiem D, Miracle K, Bronsther O, et al. Experience with liver and kidney allografts from non-heart-beating donors. Transplantation 1995; 59:197-203.

[6] Abbasoglu O. Liver transplantation: yesterday, today and tomorrow. World J Gastroenterol 2008; 14:3117-22.

[7] Atala A. Organ preservation, organ and cell transplantation, tissue engineering, and regenerative medicine: the terms may change, but the goals remain the same. Tissue Eng Part A 2014; 20:445-6.

[8] Orlando G, Baptista P, Birchall M, De Coppi P, Farney A, Guimaraes-Souza N K, et al. Regenerative medicine as applied to solid organ transplantation: current status and future challenges. Transplant Int 2011; 24:223-32.

[9] Moran E C, Dhal A, Vyas D, Lanas A, Soker S, Baptista P M. Whole-organ bioengineering: current tales of modern alchemy. Transl Res 2014; 163: 259-67.

[10] Faulk D M, Johnson S A, Zhang L, Badylak S F. Role of the extracellular matrix in whole organ engineering. J Cell Physiol 2014; 229:984-9.

[11] Daley W P, Peters S B, Larsen M. Extracellular matrix dynamics in development and regenerative medicine. J Cell Sci 2008; 121:255-64.

[12] Schenke-Layland K, Rofail F, Heydarkhan S, Gluck J M, Ingle N P, Angelis E, et al. The use of three-dimensional nanostructures to instruct cells to produce extracellular matrix for regenerative medicine strategies. Biomaterials 2009; 30:4665-75.

[13] Ott H C, Clippinger B, Conrad C, Schuetz C, Pomerantseva I, Ikonomou L, et al. Regeneration and orthotopic transplantation of a bioartificial lung. Nat Med 2010; 16:927-33.

[14] Ott H C, Matthiesen T S, Goh S K, Black L D, Kren S M, Netoff T I, et al. Perfusiondecellularized matrix: using nature's platform to engineer a bioartificial heart. Nat Med 2008; 14:213-21.

[15] Peloso A, Katari R, Zambon J P, Orlando G. Sisyphus, the Giffen's paradox and the holy grail: time for organ transplantation to transition toward a regenerative medicine-focused type of research. Expert Rev Clin Immunol 2013; 9:883-5.

[16] Petersen T H, Calle E A, Zhao L, Lee E J, Gui L, Raredon M B, et al. Tissue-engineered lungs for in vivo implantation. Science 2010; 329:538-41.

[17] Uygun B E, Soto-Gutierrez A, Yagi H, Izamis M L, Guzzardi M A, Shulman C, et al. Organ reengineering through development of a transplantable recellularized liver graft using decellularized liver matrix. Nat Med 2010; 16:814-20.

[18] Orlando G, Soker S, Stratta R J. Organ bioengineering and regeneration as the new holy grail for organ transplantation. Ann Surg 2013; 258:221-32.

[19] Baptista P M, Siddiqui M M, Lozier G, Rodriguez S R, Atala A, Soker S. The use of whole organ decellularization for the generation of a vascularized liver organoid. Hepatology 2011; 53:604-17.
[20] Badylak S F, Weiss D J, Caplan A, Macchiarini P. Engineered whole organs and complex tissues. Lancet 2012; 379:943-52.
[21] Arenas-Herrera J E, Ko I K, Atala A, Yoo J J. Decellularization for whole organ bioengineering. Biomed Mater 2013; 8:014106.
[22] Gilbert T W. Strategies for tissue and organ decellularization. J Cell Biochem 2012; 113:2217-22.
[23] Tapias L F, Ott H C. Decellularized scaffolds as a platform for bioengineered organs. Curr Opin Organ Transplant 2014; 19:145-52.
[24] Gattazzo F, Urciuolo A, Bonaldo P. Extracellular matrix: a dynamic microenvironment for stem cell niche. Biochim Biophys Acta 2014; 1840:2506-19.
[25] Yagi H, Soto-Gutierrez A, Kitagawa Y. Whole-organ re-engineering: a regenerative medicine approach to digestive organ replacement. Surg Today 2013; 43:587-94.
[26] Soto-Gutierrez A, Wertheim J A, Ott H C, Gilbert T W. Perspectives on whole organ assembly: moving toward transplantation on demand. J Clin Invest 2012; 122:3817-23.
[27] Orlando G, Farney A C, Iskandar S S, Mirmalek-Sani S H, Sullivan D C, Moran E, et al. Production and implantation of renal extracellular matrix scaffolds from porcine kidneys as a platform for renal bioengineering investigations. Ann Surg 2012; 256:363-70.
[28] Hoerstrup S P, Cummings Mrcs I, Lachat M, Schoen F J, Jenni R, Leschka S, et al. Functional growth in tissue-engineered living, vascular grafts: follow-up at 100 weeks in a large animal model. Circulation 2006; 114:1159-66.
[29] Atala A, Bauer S B, Soker S, Yoo J J, Retik A B. Tissue-engineered autologous bladders for patients needing cystoplasty. Lancet 2006; 367:1241-6.
[30] Macchiarini P, Jungebluth P, Go T, Asnaghi M A, Rees L E, Cogan T A, et al. Clinical transplantation of a tissue-engineered airway. Lancet 2008; 372:2023-30.
[31] Ko I K, Abolbashari M, Huling J, Kim C, Mirmalek Sani S H, Moradi M, et al. Enhanced re-endothelialization of acellular kidney scaffolds for whole organ engineering via antibody conjugation of vasculatures. Technology 2014; 2:243-53.
[32] Gray H. The liver. 2i. In: Anatomy of the human body. 20th ed. 1918. p. 1-54.
[33] Winterdahl M, Sorensen M, Keiding S, Mortensen F V, Alstrup A K, Hansen S B, et al. Hepatic blood perfusion estimated by dynamic contrast-enhanced computed tomography in pigs: limitations of the slope method. Invest Radiol 2012; 47:588-95.
[34] Shupe T, Williams M, Brown A, Willenberg B, Petersen B E. Method for the decellularization of intact rat liver. Organogenesis 2010; 6:134-6.
[35] Skardal A, Smith L, Bharadwaj S, Atala A, Soker S, Zhang Y. Tissue specific synthetic ECM hydrogels for 3-D in vitro maintenance of hepatocyte function. Biomaterials 2012; 33:4565-75.
[36] Zhang R, Takebe T, Sekine K, Koike H, Zheng Y, Taniguchi H. Identification of proliferating human hepatic cells from human induced pluripotent stem cells. Transplant Proc 2014; 46:1201-4.
[37] Crapo P M, Gilbert T W, Badylak S F. An overview of tissue and whole organ decellularization processes. Biomaterials 2011; 32:3233-43.
[38] Arruebo M, Valladares M, Gonzalez-Fernandez A. Antibody-conjugated nanoparticles for biomedical applications. J Nanomater 2009; 2009:1-24.
[39] Arbiser J L, Moses M A, Fernandez C A, Ghiso N, Cao Y, Klauber N, et al. Oncogenic H-ras stimulates tumor angiogenesis by two distinct pathways. Proc Natl Acad Sci U. S. A 1997; 94:861-6.

EXAMPLE 12

Whole Organ Engineering—Re-Endothelialization of Pancreas Scaffolds

Diabetes mellitus (DM) has reached pandemic levels and represents a growing burden both on health-care expenditures as well as the quality and quantity of life for afflicted individuals (194). First-line treatment is medical (oral agents and insulin) and behavioral (dietary restrictions and physical activity). Although exogenous insulin therapy is effective at preventing acute metabolic decompensation and is life-saving for type 1 DM (T1DM), less than 40% of patients achieve therapeutic goals (5). Overall, a large number of diabetic patients are inadequately controlled, complete and steady remission of hyperglycemias are rare, and treatment may be complicated by hypoglycemia, with most patients developing irreversible organ complications during their lifetimes. This means that standard exogenous insulin-based intensive glucose control can significantly reduce, but not completely protect against, the long-term complications of DM. β9cell replacement through either islet or pancreas transplantation (PTX) are the only therapies able to reliably re-establish a stable, long-term euglycemic state. PTX is indicated for patients with T1DM and some selected cases of type 2 DM (T2DM), yet it remains underutilized. In fact, in the US, for every 10,000 patients with T1DM, only 3 will actually receive PTX or islet transplant in their lifetime, due to factors such as the lack of suitable pancreas donors, the burden of chronic toxicity determined by life-long immunosuppression, and other issues related to financing and access to transplantation (5). When T2DM is considered, only three patients in one million will ever receive PTX or islet transplant. Therefore, the identification of a new, potentially inexhaustible source of β-cells for transplantation is extremely urgent.

Regenerative medicine has shown an immense potential to address the limited number of transplantable organs and to allow immunosuppression-free transplantation (9-18). Among the different technologies under development, the seeding of cells on supporting scaffolding material (cell-on-scaffold seeding technology, CSST) (19) appears to offer the quickest route to clinical application. This technology has allowed the production of relatively simple organs that were eventually implanted in more than 200 patients, for therapeutic purposes (reviewed by Orlando) (9). As these body parts were bioengineered from patient's own cells, immunosuppression was never needed. CSST is also being considered for bioengineering more complex organs for transplant purposes. We have developed an innovative method that, through the detergent-based de-cellularization of organs (e.g., porcine and human), allows successful and consistent production of acellular extracellular matrix (ECM) scaffolds (20-22). These scaffolds represent a biochemically, geometrically and spatially suitable platform for bioengineering investigations because they are biocompatible, have basic structural components well-preserved, retain essential matrix-bound growth factors and cytokines, and are able to drive differentiation of progenitor cells into an organ-specific phenotype. Moreover, the framework of the innate vasculature remains intact and, when scaffolds are implanted in vivo, the framework has the ability to sustain physiological blood pressure. Initial promising investigations in kidney and endocrine pancreas bioengineering have allowed production of natural scaffolds through the de-cellularization of porcine and human kidneys, as well as of porcine pancreata. In this latter case, a whole-organ, three-dimensional, acellular scaffold was generated using the porcine pancreas. Histology and imaging studies confirmed that the protocol disclosed herein effectively removes cellular material while preserving ECM proteins and the framework of the native vascular tree. Moreover, when these scaffolds are seeded with precursor cells, cells adhere, proliferate and are both viable and functioning; when pancreatic islets are seeded, they are able to respond to a glucose stress test (20).

It is expected that when a patient will need beta cell replacement therapy, s/he will be offered a new generation bio-artificial endocrine pancreas (BAEP) produced from his/her own cells that will be seeded in the three-dimensional framework of ECM scaffolds manufactured from pancreata of human or porcine origin. Therefore, we have applied the disclosed de-cellularization method to discarded human pancreata in order to generate acellular pancreatic ECM scaffolds. Disclosed herein are investigations on the generation of human pancreas acellular ECM scaffolds (hpaECMs), which represent the hardware of the bioengineered BAEP.

Pancreas and Endothelial Cell Procurement

Twenty-five human pancreata obtained from the service area of our local procurement organization (Carolina Donor Services—CDS) were processed. Each organ was originally recovered for transplantation, but subsequently discarded for steatosis, fibrosis, vascular anomalies or inflammation. After the national list was exhausted, pancreata from donors with research consent were released for subsequent investigations.

Pancreas Preparation

Organs were received in cold sterile preservation solution after en-bloc removal that included the whole organ pancreas, duodenum and spleen, and then prepared by removing the duodenum and ligating all of the vascular branches from the arterial arcade connecting the pancreatic head with the duodenum using 390 silk sutures. Thereafter, the pancreatic duct (PD) was cannulated with a 14G catheter. The peripancreatic fat was trimmed, the splenic vessels were ligated at the splenic hilum, and the spleen was removed. The superior mesenteric artery (SMA) and proximal stump of the splenic artery (SA) were cannulated using 16G plastic connectors. Pancreata were then washed with 500 ml of saline solution containing 50 ml of povidone-iodine (betadine) and then with 10% Penn/Strep solution. Pancreata were eventually rinsed with 500 ml of sterile PBS and stored at 4° C.

Pancreas Decellularization

After placing the pancreas in an ad hoc container, PD, SMA and SA were connected to a double-line peristaltic pump (Masterflex L/S, easy load pump head and L/S 16G tubing, Cole-Parmer Instrument Co., Vernon Hills, Ill., USA) (FIG. 1). Then, the pancreas was flushed with 4° C. phosphate buffer solution (PBS) and heparin (1% of 1000 U, 10 U/ml) at 6 ml/minute for 60 minutes (360 mL total). Afterwards, 1% 2-[4-(2,4,4-trimethylpentan-2-yl)phenoxy]ethanol (Triton X-100) and 0.1% ammonium hydroxide solution were perfused at 12.5 ml/minute for 48 hours (72 L total) through both inlets (PD and SMA/SA inlets), at 4° C. The so-obtained hpaECMs were then rinsed with DNAse (D5025—Type IV, deoxyribonuclease from bovine pancreas, Sigma Aldrich, St. Louis, Mo.) and 0.0025% magnesium chloride). Finally, scaffolds were perfused with saline at a flow of 6 mL/minute for 5 days (12,900 L total) to remove detergent and stored at 4° C. Scaffolds destined for cell-seeding experiments (see below) were sterilized by y-irradiation (12,000 Gy) and stored in PBS at 4° C.

Bioscaffold Characterization—Vessel Patency

To evaluate the patency of the hpaECMs' innate vasculature, angiography was performed by injecting 5 ml of contrast agent in each of the inlets (PD, MSA and SA, 15 mL total) at a flow rate of 25 mL/minute.

Bioscaffold Characterization—Collagen and DNA Quantification

Collagen and DNA content of fresh and de-cellularized pancreas was measured through indirect quantification of hydroxyproline residues using the Quick9Zyme Total Collagen Assay (QuicZyme, Biosciences), and using a tissue DNA isolation kit (PureLink Genomic DNA MiniKit, Invitrogen), respectively, as described by Orlando et al. (22).

Bioscaffold Characterization—Basic Histology, Immunofluorescence and Cellularity hpaECMs samples were fixed for 24 hours in formalin, washed in diH2O, dehydrated in graded alcohol, embedded in paraffin, 5 mm-sectioned, and eventually stained with H&E, Masson's Trichrome (MT), elastic Van Gieson (EVG), Alcian Blue (AB) and Picrosirius Red (PR). Slides were compared with counterparts obtained from discarded pancreata that did not undergo de-cellularization.

For immunofluorescence analysis, slides were incubated overnight with primary antibodies against collagen type I (dilution 1:25, Southern Biotech), collagen type IV (dilution 1:100, Southern Biotech), fibronectin (dilution 1:100, Santa Cruz), laminin (dilution 1:200, Sigma), HLA Class I (dilution 1:100, Abcam) and HLA DP+DR+DQ (dilution 1:25, Abcam). Nuclei were counterstained with DAPI. Slides were visualized using fluorescence microscopy (Carl Zeiss) and compared to counterparts obtained from discarded pancreas that did not undergo de-cellularization.

To quantify the remaining cells after de-cellularization, a portion of fresh and acellular tissue was frozen in liquid nitrogen and 10 slides of each tissue were analyzed with an optical microscope. The samples were covered with Vectashield (Vector Laboratories, Inc., Burlingame, Calif.) mounting medium for fluorescence with 40-6-diamidino-2-phenylindole (DAPI) (Vector Laboratories, Inc), and the total number of nuclei per field was counted in random pictures using fluorescence microscopy (Carl Zeiss).

Bioscaffold Characterization—Scanning Electron Microscopy (SEM)

To evaluate scaffold ultrastructure, samples of hpaECMs and normal pancreas were processed and analyzed as described by Orlando et al. (22). Images were recorded with a Jeo17401 FEG scanning electron microscope.

Bioscaffold Characterization—Chicken Chorioallantoic Membrane (CAM) Angiogenic Assay To assess the angiogenic properties of the scaffolds, a CAM assay was used, as previously described (22-24). To assess angiogenesis, the number of blood vessels converging towards de-cellularized matrices was counted manually. Only blood vessels less than 10 mm in diameter were counted by blinded assessors (n=4), with the mean of the counts being considered.

Bioscaffold Characterization—Measurement of Pancreatic Tissue Stiffness

To assess hpaECMs stiffness, dog bone-shaped samples, 4 mm wide at the narrowest point with a length of 18 mm, were punched from wet pancreas before and after the de-cellularization process. The mechanical properties were measured using tensile extension by a uniaxial load test machine (Instron5544, Instron Corporation, Issaquah, Wash.) with an extension rate of 10.0 mm/minute. Stress-strain curves for scaffolds were recorded and Young's modulus, tensile strength, and strain at break were obtained. Six samples were measured for each scaffold allowing the mean and standard deviation to be calculated.

Bioscaffold Characterization—Growth Factor (GF) Analysis

We expected growth factors, cytokines and chemokines to be only partially depleted from our matrices. To confirm this expectation, 5 hpaECMs were produced from 5 different organs (study group). Two samples were procured from each scaffold (10 pieces total) with a 12 mm biopsy punch; the control group consisted of 10 samples obtained in the same fashion from 5 discarded pancreata that did not undergo de-cellularization. All samples were stored in sterile PBS with 2% pen/strep and then shipped to the manufacturer (Raybiotech, http://www.raybiotech.com), where they were processed using the Quantibody® Human Growth Factor Array Q1. The results of the experiments assessing depletion of growth factors from the matrices are presented in Table 3.

respectively) (Table 3). In Group 2, PDGF-AA (platelet-derived growth factor AA), HB-EGF (heparin binding epidermal growth factor), TGFα (transforming growth factor α) and TGFβ1 (transforming growth factor β1) were well-preserved at 81.21%, 57.35%, 48.88% and 49.16% of the initial content. MCFr (mitochondrial carrier family receptor), SCF (stem cell factor), and TGFβ3 (transforming growth factor β3) were moderately present: 26.05%, 17.17%, and 14.72%, respectively. In Group 3, BDNF (brain derived neurotrophic factor), b-NGF (nerve growth factor binding protein), GDNF (glial cell line derived neurotrophic factor) and NT-3 were present at 13.97%, 14.18%, 16.09% and 10.11% of the initial content, respectively. NT-4 (neurotrophin 4) was almost completely absent post-de-cellularization (5.07%). In Group 4, GH (growth hormone), BMP7 (bone morphogenetic protein 7), BMP5 (bone morphogenetic protein 5), BMP4 (bone morphogenetic protein 4), IGF-1 (insulin-like growth factor 1) and NGFr (nerve growth factor receptor) remained at 37.76%, 24.7%, 32.6%, 9.23%, 2.6%, and 7.67% of the initial content, respectively. Assessment of the Ability of hpaECMs to Sustain Cell Attachment and Growth

TABLE 3

| Angiogensis and vasculogenesis | | | | Embryogenesis, growth and regeneration | | | |
|---|---|---|---|---|---|---|---|
| Growth factor | Native Pancreas (pg/ml; av) | hpaECM (pg/ml; av) | Percentage remaining after decellularization (%) | Growth factor | Native Pancreas (pg/ml; av) | hpaECM (pg/ml; av) | Percentage remaining after decellular-Percentage |
| EG-VEGF | 29.33 | 25.62 | 87.35 | PDGF-AA | 980.94 | 796.63 | 81.21 |
| VEGF R3 | 371.74 | 149.96 | 40.34 | HB-EGF | 1.36 | 0.78 | 57.35 |
| FGF4 | 70024.94 | 9869.22 | 14.09 | TGF-a | 0.45 | 0.22 | 48.88 |
| VEGF R2 | 851.24 | 116.71 | 13.71 | TGF-b1 | 23.43 | 11.52 | 49.16 |
| AR | 50.13 | 6.36 | 12.63 | MCF R | 2131.05 | 55.26 | 26.05 |
| bFGF | 62182.22 | 6819.13 | 10.95 | SCF | 283.15 | 48.62 | 17.17 |
| VEGF | 69.95 | 6.44 | 9.2 | TGF-b3 | 85.64 | 12.61 | 14.72 |
| VEGF D | 37.01 | 0.36 | 0.97 | | | | |

| Viscero afferent neuronal development | | | | Insulin level and glucose homeostasis control | | | |
|---|---|---|---|---|---|---|---|
| Growth factor | Native Pancreas (pg/ml; av) | hpaECM (pg/ml; av) | Percentage remaining after decellular-Percentage | Growth factor | Native Pancreas (pg/ml; av) | hpaECM (pg/ml; av) | Percentage remaining after decellular-Percentage |
| BDNF | 1.36 | 0.19 | 13.97 | GH | 1009.83 | 381.39 | 37.76 |
| b-NGF | 4.16 | 0.59 | 14.18 | BMP7 | 1248 | 308.4 | 24.7 |
| GDNF | 26.55 | 4.34 | 16.09 | BMP5 | 2199.15 | 717.03 | 32.6 |
| NT-3 | 23.72 | 2.4 | 10.11 | BMP4 | 98.27 | 9.08 | 9.23 |
| NT-4 | 25.99 | 1.32 | 5.07 | IGF-1 | 1431.39 | 37.3 | 2.6 |
| | | | | NGF R | 50.17 | 3.85 | 7.67 |

Figure 37:
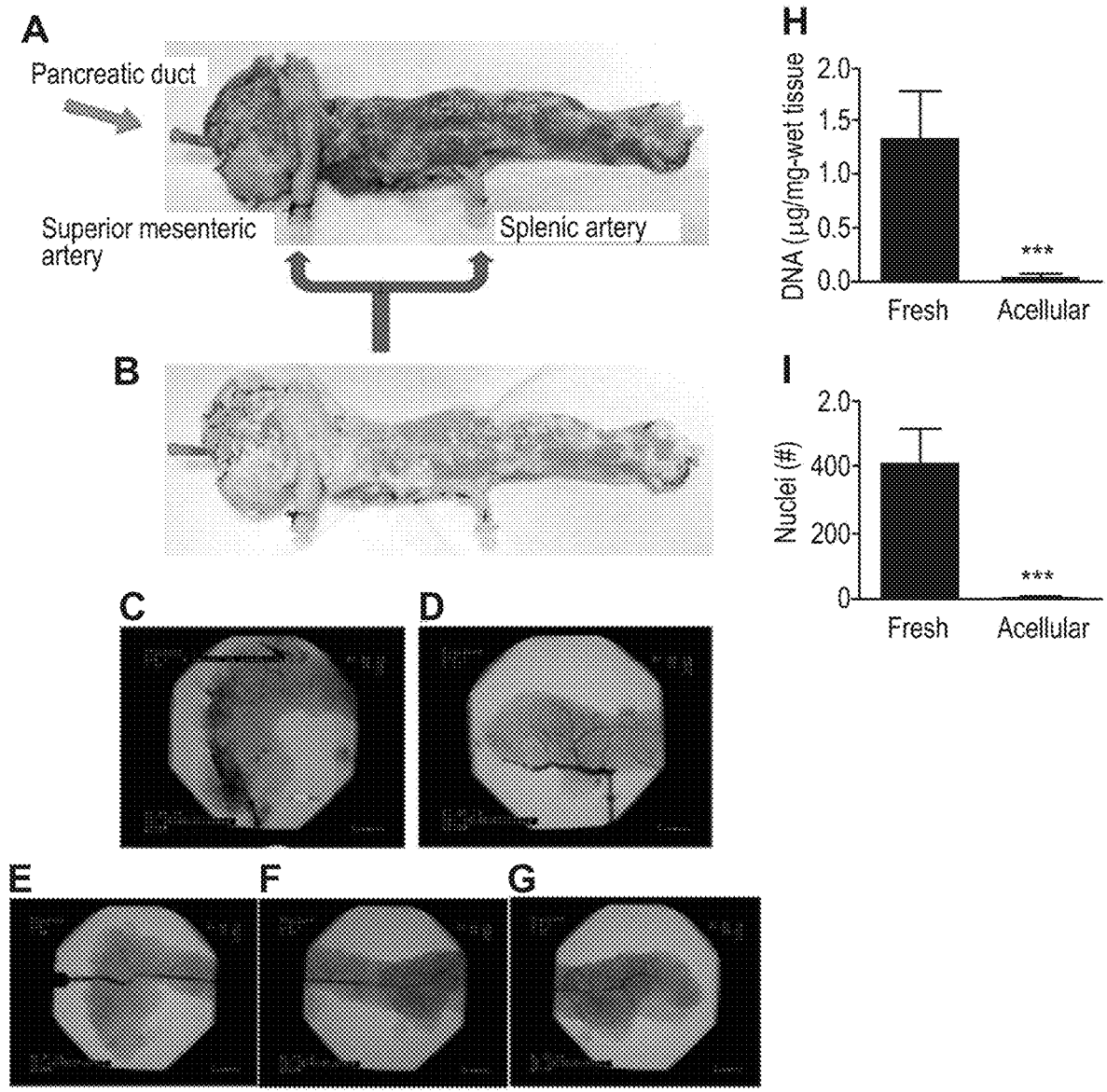
FIG. 37. De-cellularization process, fluoroscopy and DNA quantitation. Panels A and B show the set-up of the core for organ decellularization in a discarded human pancreas before and after the treatment. Red arrows in the first image show the arterial, represented by superior mesenteric artery (SMA) and splenic artery (SA) that share one of the two detergent inflows. Green arrow indicates the second inflow through the pancreatic duct (PD). During decellularization, the color of the organ macroscopically changed from a golden brown color to straw yellow but without reaching the whitish color described for porcine pancreas scaffolds (20). Fluoroscopy of hpaECMs performed through SMA (Panel C), SA (panel D) and PD (panel E, F, G). Contrast media flows within the framework of the innate vasculature of hpaECMs without extravasation. Panel H confirms satisfactory cell and DNA clearance. Statistical analysis included t-test of fresh versus acellular tissue; *** $p<0.001$.

GF analysis. Table 3 illustrates the growth factors (GFs) retained within hpaECMs after decellularization. GFs were divided in four groups by their function: angiogenesis and vasculogenesis (Group 1), growth and regeneration (Group 2), neuronal development (Group 3) and insulin level and glucose homeostasis Group 4). In Group 1, EG-VEGF (Endocrine Gland—derived Vascular Endothelial Growth Factor) and VEGF9r3 (Vascular Endothelial Growth Factor receptor 3) were significantly present (87.35% and 40.34% of the initial content, respectively); VEGF-r2 (vascular endothelial growth factor receptor 2), AR (amphiregulin), FGF94(fibroblast growth factor 4), bFGF (fibroblast growth factor binding protein) were moderately present (13.71%, 12.63%, 14.09% and 10.95%, respectively) whereas VEGF (vascular endothelial growth factor), FGF97 (fibroblast growth factor 7) and VEGF D (vascular endothelial growth factor D) were poorly present (9.2%, 3.81% and 0,97%, a) Human islets: Pancreases were processed using standard Liberase HI collagenase digestion with mechanical dissociation within a Ricordi chamber. Islets were purified with an optiprep discontinuous gradient method, identified and counted using dithizone staining. paECMs samples were prepared as shown in FIG. 37, sterilized via γ-irradiation and placed in RPMI with 10% FBS overnight at 4° C., prior to seeding. The day after, 200 islets per scaffold were statically seeded on matrices with fresh media and cultured under standard conditions in RPMI media with 10% FBS for 4 days prior to perifusion testing (20). As control, additional islets were cultured on standard Petri dishes under the same culture conditions. Briefly, each group of 200 islets was placed into perifusion chambers, either seeded on scaffolds or free. The chambers were then perfused with Krebs-Ringer-bicarbonate (KRB) solution containing 0.2% bovine serum albumin (BSA) at a flow rate of 0.3 mL/minute.

During the procedure, the KRB was continuously gassed with 95% air/5% $CO_2$. The islets were pre-perfused for 1 hour in a low-glucose (3.3 mM) KRB solution prior to sampling. After one hour, effluent samples were collected from the low-glucose KRB solution every 5 minutes for 20 minutes. Then a high-glucose solution (16.7 mM) was perfused through the chambers for 30 minutes with effluent sample collection every 2 minutes. Following the 30 minutes of high glucose, the chambers were perfused again with low-glucose KRB for 30 minutes with sample collection every 5 minutes. The effluent samples were stored at −20° C. until analyzed for insulin content via radioimmunoassay. Insulin values are normalized to basal averages, n=4, error bars represent SEM.

b) Human endothelial cells: Human primary pancreatic endothelial cells (hPPECs) were isolated from discarded pancreata as described by Navone et al. (25). Cells were then expanded on matrigel-coated flasks and grew with endothelial proliferation medium (EndoPM). At the time of seeding, $20 \times 10^6$ cells were injected with a syringe pump in a whole acellular pancreas scaffold through the SMA and SA, at a flow of 0.2 ml/minute. Cells were allowed to attach for 2 hours, after which perfusion culture was started. Seeded matrices were cultured in a custom-built bioreactor (FIG. 43B). Media were infused through Luer lock access ports and allowed to equilibrate with 5% $CO_2$ and 95% room air by insertion of 0.22 μm filters and magnetic stirring. The system (and the related technical support) was designed and developed by SKE Advanced Therapies. After 6 days, matrices were fixed in formalin, sampled into 5-μm sections, and stained for H&E, CD31 (clone JC70A, 1:100, DAKO), Ki67 (clone Mib1, 1:600, DAKO) using standard protocols. Antigen retrieval was performed with Tris EDTA pH 9 for both antibodies. The percentage of Ki67+ cells was obtained as the ratio of Ki67+ and hematoxylin+ cells. Immunohistochemistry and H&E-stained images were recorded using Aperio Scan System (Leica Microsystems).

Human Pancreas De-Cellularization

Non-ionic detergent-based (Triton-based) perfusion allowed complete clearance of the cellular compartment of discarded pancreata (FIG. 37A-B). Fluoroscopy depicted an intact vascular network that retained the hierarchical branching structures (Supplementary FIG. 37C-G). In fact, contrast media flowed progressively from larger vessels to smaller capillaries to eventually drain out through the venous outlets, without extravasating within the hpaECMs.

Collagen and DNA Quantification

To investigate the ability of the de-cellularization protocol to maintain ECM components of the native pancreas, fresh and acellular samples were processed for collagen quantification. Quantitative assay showed statistically increased collagen in acellular matrices compared to fresh tissue (from 22.9±10.0 to 75.4±16.8 μg/mg, $P<0.001$). DNA analysis was performed as indirect proof of successful decellularization and demonstrated approximately 99% clearance of DNA in comparison with the native organ (from 1.35±0.43 to 0.04±0.03 μg/mg, $P<0.001$) (FIGS. 1C-G).

Basic Histology, Immunofluorescence and Cellularity

Figure 38:
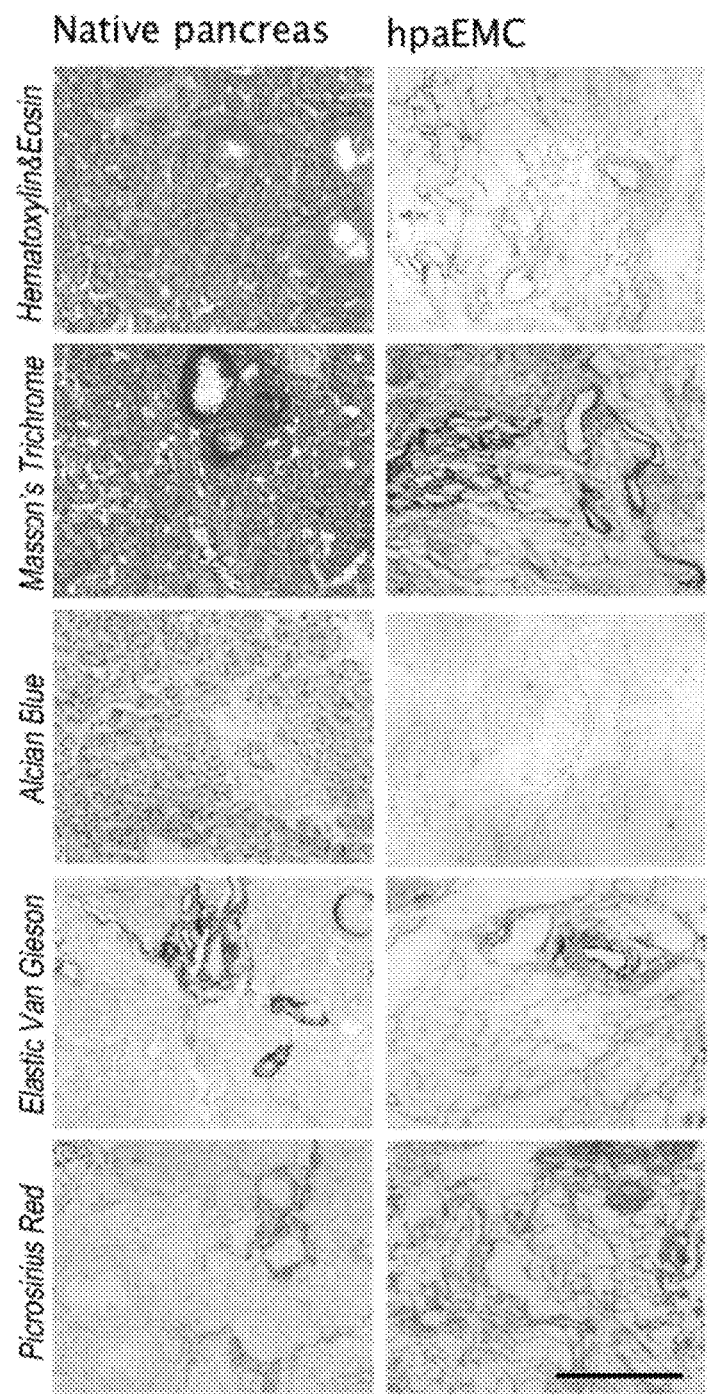
FIG. 38. Basic histology of hpaECMs as compared to the native pancreas. H&E demonstrates complete loss of cellular elements with preservation of the intercellular framework. Without wishing to be bound by theory, the larger empty spaces on the left aspect of the section may reflect pathological lesions, possibly representing focal fat necrosis. Masson trichrome shows the light green ECM framework. On the left aspect of the right panel there is evidence of scarring, indicated by the dense area staining green. Alcian blue demonstrates preservation of the ground substance in the connective tissue framework, although the process of digestion involved in de-cellularization has altered the faint blue color of Alcian blue into a faint green color, as can be seen in the right panel. The van Gieson stain for elastic tissue demonstrates preservation of the elastic tissue of a couple of small structure of unclear nature in the right panel. The picrosirius red demonstrates abundant collagen in the right panel, reflecting significant scarring in the field photographed in contrast to the left panel.

Fresh and acellular samples were processed for Masson trichrome, Picrosirius red, elastic Van Gieson and Alcian blue (FIG. 38). All stainings confirmed complete absence of nuclear material and cells, consistent with the H&E and DAPI findings. Masson trichrome and Picrosirius red revealed preservation of collagen fibers, both in the native tissue and acellular matrices. Alcian blue staining indicated some preservation of sulfated glycosaminoglycan proteins in the scaffolds. Elastic Van Gieson staining showed that elastin was retained after de-cellularization. Elastin is an essential component of the basal membrane of vascular structures and ducts in the pancreas, as highlighted by EVG staining in fresh samples.

Figure 39:
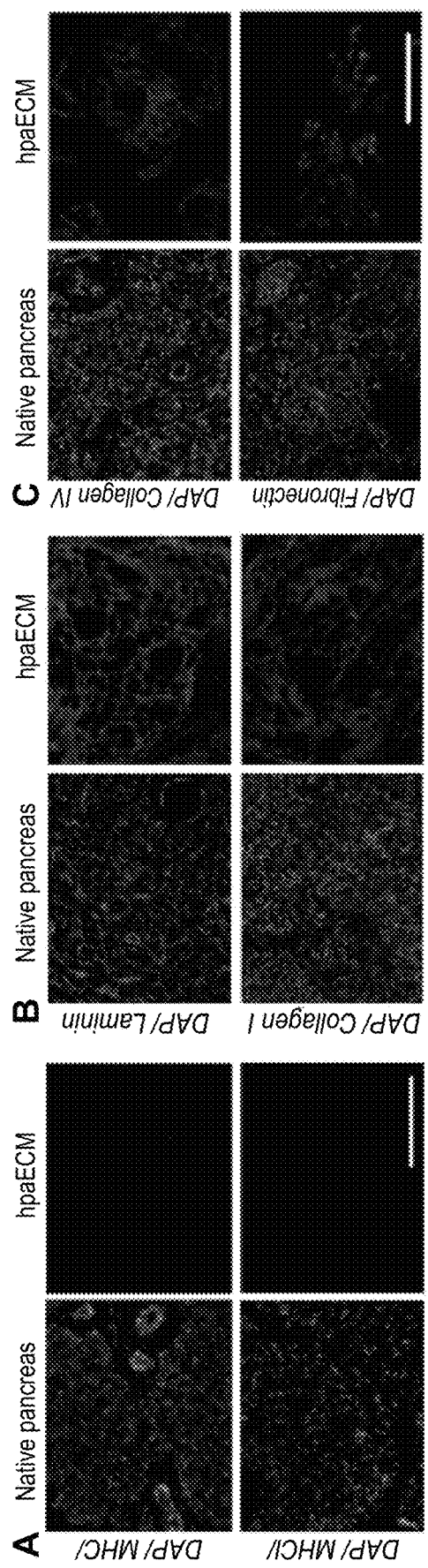
FIG. 39. Immunohistochemistry. Aside of nuclear staining, presence of possible immunogens was ruled out by immunostaining for major histocompatibility complexes of class I and II (MHC I and II). Immunostaining for critical, ubiquitous components of pancreas ECM showed that laminin, fibronectin, collagen type I and IV remain well-preserved in hpaECMs (nuclei were counterstained with DAPI) and displays a similar distribution of these proteins in the fresh and de-cellularized pancreas bioscaffold sections.

DAPI and H&E staining, as well as immunofluorescence for both MHC class I and class II antigens confirmed the complete clearance of the cellular compartment of the hpaECMs (FIG. 39). As expected, the scaffolding architecture of the pancreas was well preserved. In fact, H&E staining showed the pink eosinophilic staining typical of collagen in the absence of any basophilic staining indicative of cellular nuclear material. Specific nuclei staining with DAPI confirmed the absence of cell nuclei after de-cellularization. This finding was also supported by the count of the total number of nuclei per field in random pictures (from 410±120 to 0 nuclei, $P<0.001$). As an indirect sign of successful de-cellularization, neither MHC class I- nor class II-positive cells were seen in the pancreatic matrices.

Immunofluorescence for specific ECM molecules that have a significant role in the pancreatic parenchyma was performed for a fuller characterization of our scaffolds. Immunostaining detected the presence of laminin, collagen I, collagen IV and fibronectin in the native pancreas (FIG. 39). Laminin detection in the acellular matrix showed strong positivity similar to fresh tissue, especially around vessels and structures resembling the native sites of the islets. In contrast, preservation of collagen I was less evident with respect to the fresh pancreatic ECM, while immunofluorescence for collagen IV and fibronectin showed specific distribution of both components at the same level of native tissue.

Scanning Electron Microscopy (SEM) Analysis

Figure 40:
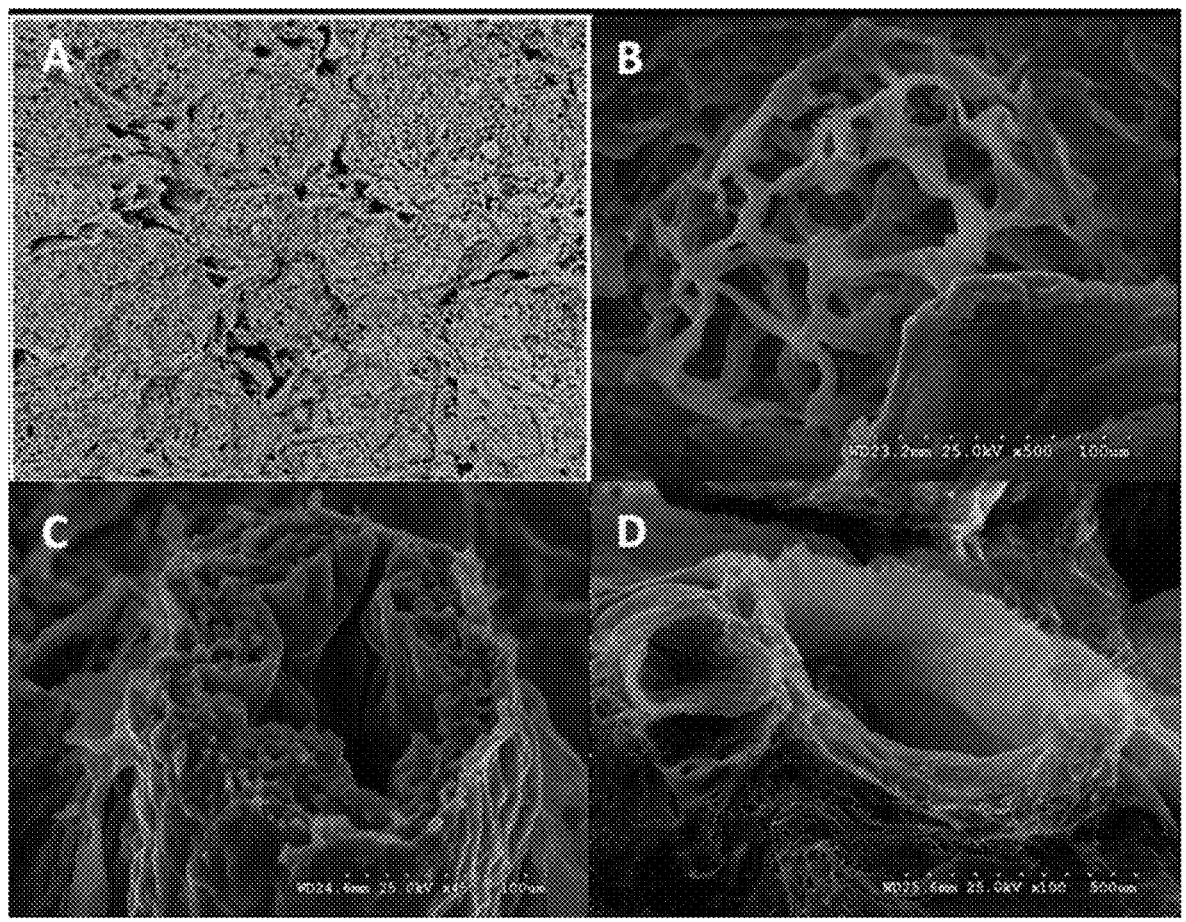
FIG. 40. SEM of intact and acellular pancreas ECM. A. Low power magnification of a cross section through the de-cellularized pancreas demonstrating preservation of the ECM supporting the exocrine and endocrine elements as well as the vasculature. B. Three dimensional view of the ECM framework of an islet of Langerhans in the de-cellularized pancreas, identifiable by what is presumably its spherical microvascular framework. C. Cross-section through an arteriole with the lumen delimited by the internal elastic membrane and external to it, the individual layers of basement membrane of dissolved smooth muscle fibers of the arteriole's media. D. A venule identifiable by the smaller number of layers of smooth muscle cells (identified by the layers of basement membrane) forming its wall and two small tributaries contributing to its formation.

SEM revealed retained nanofibrous structures in hpaECMs and confirmed the absence of intact cells, indicating that the de-cellularization process produced an acellular matrix scaffold that retained the micro- and ultra-structural details of pancreas architecture (FIG. 40).

CAM Assay

Figure 41:
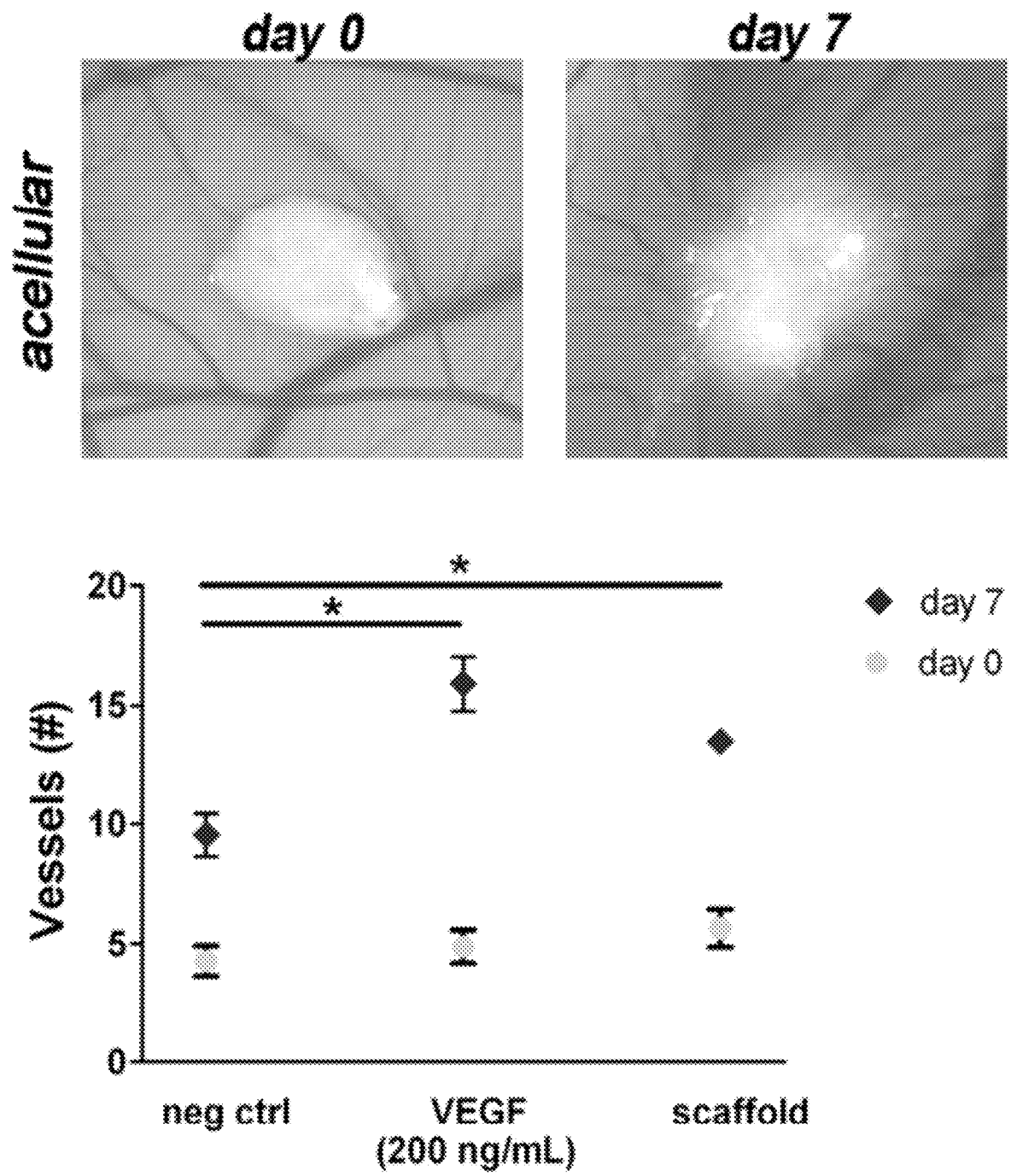
FIG. 41. CAM assay. CAM assay showed that, after seven days of implantation, the number of vessels converting towards the de-cellularized pancreas significantly increased in comparison to the same samples at day 0, and the negative control.

To test the ability of pancreatic acellular matrices to induce neo-angiogenesis, fragments of de-cellularized pancreas were placed on the chicken egg CAM. Macroscopic observations of CAM treated with acellular matrices showed that the scaffolds integrated well with the developing environment of the chicken egg and representative images of scaffold placed in ovo at 0 and 7 days of incubation demonstrated attraction of blood vessels that, in a spoke-wheel pattern, seem to penetrate the tissue (FIG. 41). The effect of pancreatic acellular matrices on directed blood vessel growth was quantified by manually counting the total number of blood vessels converging towards matrices. Seven days after implantation, the number of vessels growing towards the acellular scaffold was significantly increased in comparison to the same sample at day 0 ($P<0.05$) and to the filter membrane loaded with PBS that was used as a negative control ($P<0.05$). Interestingly, acellular matrices pro-angiogenic effect after 7 days from implantation into the CAM, was comparable with VEGF-loaded membrane used as positive control ($P>0.05$).

Acellular Scaffold Stiffness Properties

Figure 44:
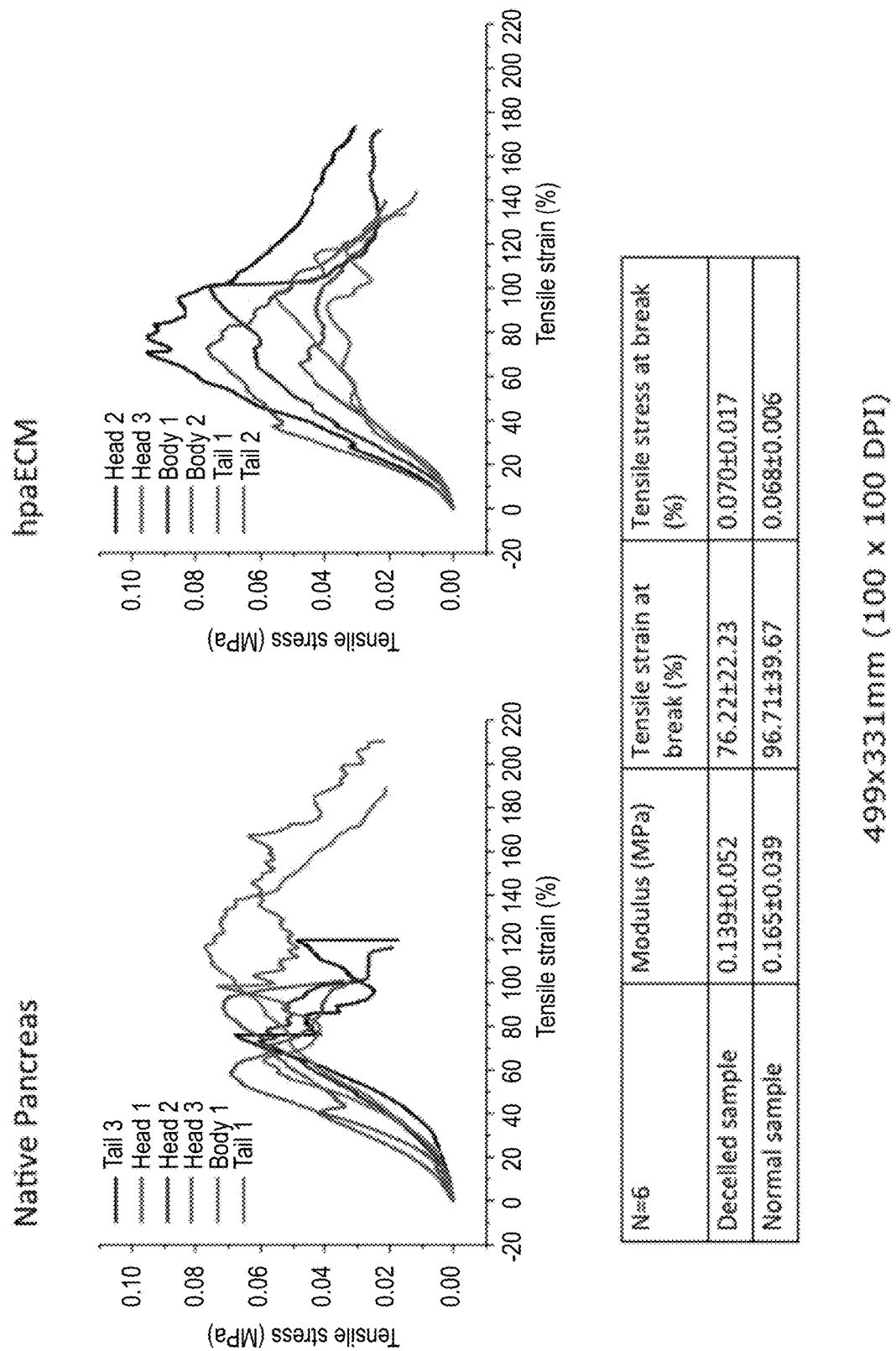
FIG. 44. Mechanical properties of hpaECMs. Graph on mechanical properties show similar patterns between native pancreata (non-treated) and hpaECM for tensile strain. Table below indicates data related to modulus (expressed in MPa), tensile strain at break (%) and tensile stress at break (%).

It has been proposed that the ECM has the ability to maintain the original mechanical properties of native organs. By assessing the mechanical properties of our scaffolds, we were able to partially elucidate the influence of the de-cellularization process on ECM in terms of destruction, degradation and/or decomposition. The properties of native pancreas were compared with that of hpaECMs. The results showed that the Young's moduluses and tensile strain at break had slight decreases, but no significant difference after the removal of cellular components, changing from 0.165±0.039 MPa and 96.71±39.67% to 0.139±0.052 MPa and 76.22±22.23%, respectively (FIG. 44). The tensile stress at break of decellularized pancreata (0.070±0.017 MPa) was comparable to the native pancreas (0.068±0.006 MPa) (P<0.05). These results indicated that the ECM plays a prominent role in determining the mechanical properties of the pancreas, and that our decellularization method effectively maintains the integrity of the tissue's ECM without destruction or degradation.

hpaECMs Retain GFs

Data obtained from the quantitative array platform showed that several GFs were still present in the hpaECMs after de-cellularization. Some of these molecules are essential in angiogenesis and vasculogenesis, cell development, neuronal growth and regeneration, as well as insulin level and glucose homeostasis (Table 3).

Figure 42:
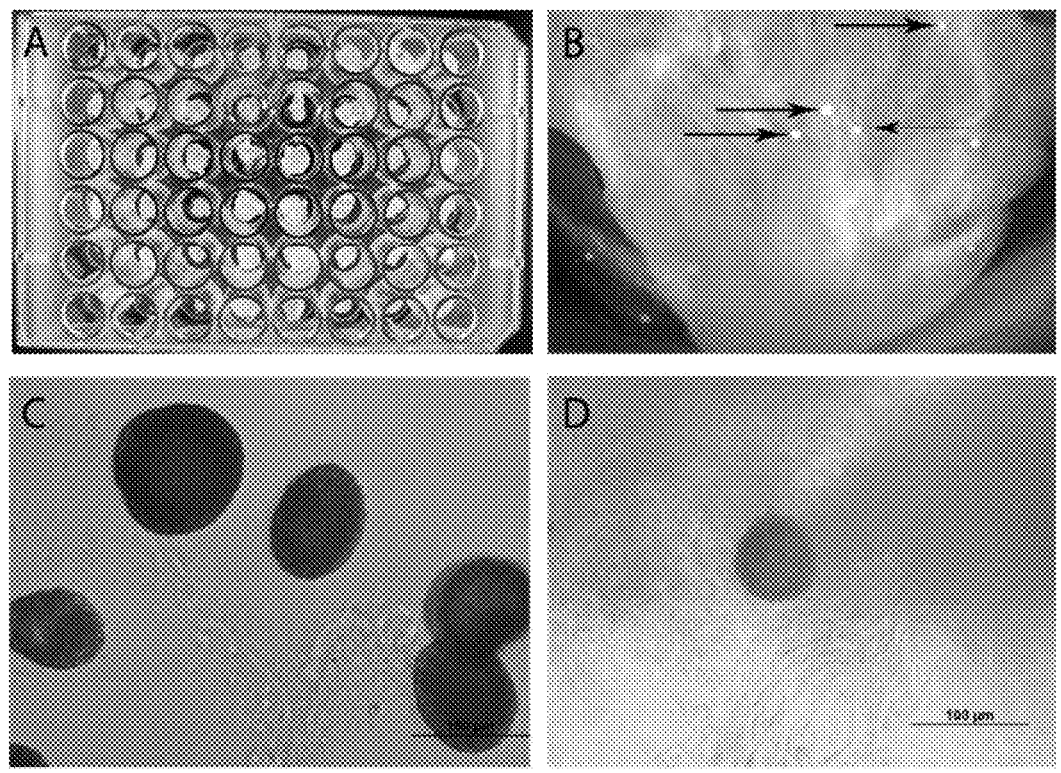
FIG. 42. Seeding of islets onto de-cellularized scaffolds. (A) De-cellularized scaffolds prior to seeding. (B) Scaffold immediately after seeding, black arrows indicate islets. (C) Dithizone-stained islets after 4 days in culture on culture plates. (D) Dithizone-stained islet located on periphery of scaffold, 4 days after seeding onto scaffolds. The plot (E) illustrates dynamic perifusion results for human islets after 4 days if culture. Here, both islets in standard culture conditions as well as islets seeded statically on scaffolding demonstrated similar responses to changes in glucose where insulin secretion rates increased during the 16.7 mM glucose perifusion, then dropped back down to basal levels during the second 3.3 mM glucose perifusion period. Of 3 separate perifusion experiments the average stimulation index for islets cultured on the scaffolds was 2.81±0.48 which was not significantly different from islets cultured on standard plastic petri dishes, which had a stimulation index of 3.44±1.821 (p=0.59, average±standard deviation, n=3).
Figure 42:
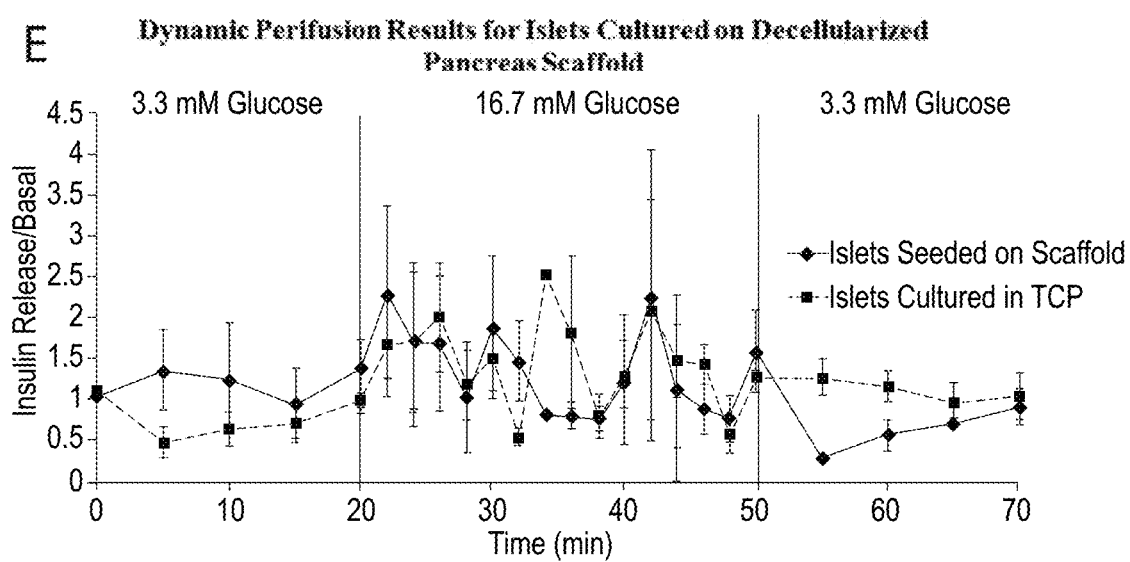
Figure 43:
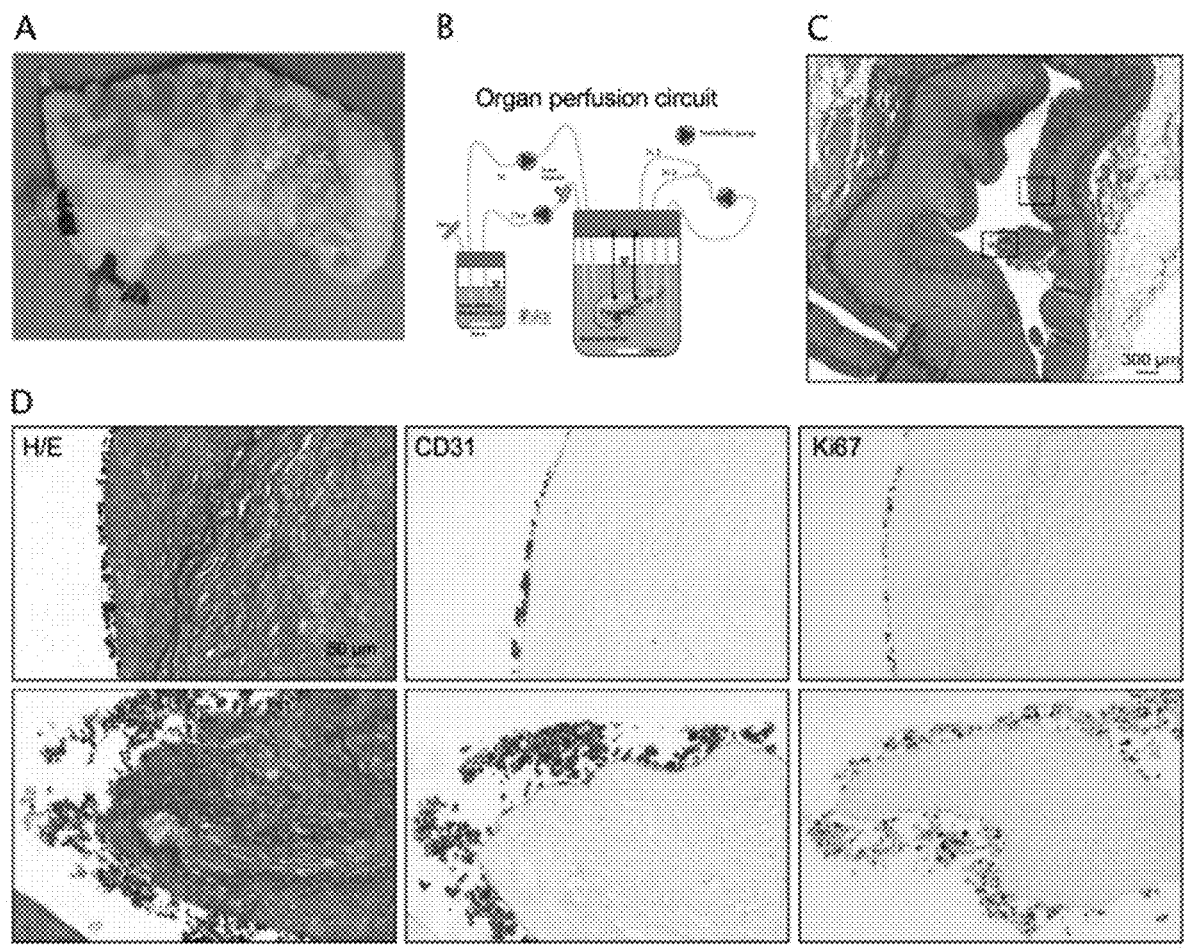
FIG. 43. Endothelial cell seeding. Matrix was seeded with human pancreatic endothelial cells and cultured for six days in a bioreactor, consisting of a closed circuit with one chamber for organ housing, a reservoir for medium oxygenation and a peristaltic pump (Ismatec), connected by tubing (ID 1/16", Pharmed BPT). Pancreatic tail was surgically isolated in order to obtain a smaller volume to seed, keeping at the same time an inflow (SA—red connector) and an outflow (Splenic Vein 9SV9 blue connector) (Panel A). Panel B indicates a schematic representation of the perfusion circuit for seeded pancreatic scaffold culture. Panel C shows a representative image of H&E stain showing localization of infused cells in vessels. Boxes indicate areas reported with high magnification in the panel below. Panel D illustrates representative images of H&E (left), CD31 (middle) and Ki67 (right) matrix staining.

Cell Seeding of Acellular Pancreatic Scaffold a) Human Islets: Islets stained positive for DTZ on both scaffolding (FIG. 42D) and culture dishes (FIG. 42C). Both islets seeded on scaffolds and islets on culture dishes were functional following 4 days of culture with similar stimulation indices (as defined as the peak insulin secretion rate divided by the basal insulin secretion rate) of 2.81±0.48 and 3.44±1.821, respectively (p=0.59, average±standard deviation, n=3).

b) Human endothelial cells: At H&E, cells were ubiquitous within the matrices, yet tended to localize at the level of small and large vessels (FIG. 43). Cells distributed in a line on the edges of the vessel walls resembling primitive structures of vessel formation. All cells confirmed their endothelial nature as evidenced by CD31 staining. More than 50% of cells were proliferating, as determined by Ki67 staining, demonstrating that a mid-term culture in the acellular scaffold allows cell survival and proliferation.

The experiments disclosed in this Example and elsewhere throughout the application represent a progression that supports the expectation that ECM scaffolds generated from native pancreas tissue can serve as a platform for insulin-producing bioengineered tissue (4, 20, 26). The importance of transitioning to human organs is obvious in the context of clinical relevance. The results disclosed herein indicate that whole discarded human pancreata can be consistently and successfully decellularized through detergent-based perfusion methodology. Indeed, cell clearance is achieved despite preservation of the ECM's architecture, composition and mechanical properties. In addition, the framework of the vascular network remains intact at all hierarchical levels. As a corollary to the complete absence of HLA class I and II antigens, it may be inferred that the so-obtained scaffolds may not be significantly immunogenic. Interestingly, for the first time it is disclosed that numerous GFs are retained in significant amounts within the three-dimensional structure of hpaECMs. Some of these GFs are key players in essential pathways such as angiogenesis, cell proliferation and glucose metabolism, and their presence may justify the scaffold's ability to induce angiogenesis in the CAM assay.

The data obtained with discarded human pancreas are consistent with our previous experience with discarded human kidneys (22). However, in contrast to that experience, we used non-ionic detergent (Triton) rather than the more aggressive SDS for two reasons: first, because the density of the pancreas texture is inferior to the kidney, which is basically refractory to nonionic detergents such as Triton; second, we believe that pancreatic enzymes released during cell breakdown occurring during the de-cellularization process can, in turn, contribute to further clearance of the cellular compartment. Moreover, these experiments with human pancreas are consistent with experiments performed using porcine pancreas (20). In those experiments, pig pancreata were subjected to a 24-hour cycle of de-cellularization with a non-ionic detergent-based (Triton-based) solution. Nevertheless, in the case of discarded pancreata, a 48-hour de-cellularization cycle was used—twice the length—that was infused through three different inlets (PD, SMA and SA), rather than just two, namely the PD and the superior mesenteric vein. The adjustment followed initial unsuccessful attempts while using only the original two inlets, 24-hour approach, in which a frank impairment of the de-cellularization process was observed, possibly attributable to the significant tissue damage that had justified discard. Overall, it was expected that the 3-inlet approach— namely, PD, SMA and SA— would lead to successful de-cellularization, as it would allow ad hoc delivery of the detergent throughout the whole pancreas; and that the higher volume would possibly circumvent hurdles deriving from organ damage such as steatosis and fibrosis.

In order to assess the cytocompatibility of hpaECMs, islets and a unique endothelial cell line isolated from the human pancreas, namely hPPECs, were used. In both cases, findings show that the matrices are both and cell-friendly, as they allow attachment, function and maintain the initial phenotype. In the attempt to assess cytocompatibility, while the choice of islets is obvious, hPPECs are justified because it is expected that the first step to follow the production of hpaECMs will be the reconstitution of the endothelium starting from a patient's own endothelial cells. Consistent with the disclosures herein relating to renal ECM scaffolds produced from discarded kidneys, it is important to emphasize that the strategy of using discarded organs introduces a new type of biomaterial, represented by natural scaffolds obtained from the manipulation of organs with pre-existing damage.

REFERENCES—FOR EXAMPLE 11 ONLY 1) http://www.cdc.gov/diabetes/pubs/estimates11.htm
2) Boyle J P, Thompson T J, Gregg E W, Barker L E, Williamson D F. Projection of the year 2050 burden of diabetes in the US adult population: dynamic modeling of incidence, mortality, and prediabetes prevalence. Popul Health Metr 2010; 8:29
3) American Diabetes Association. Economic costs of diabetes in the U.S. in 2012. Diabetes Care 2013; 36:1033946
4) Orlando G, Gianello P, Salvatori M, Stratta R J, Soker S, Ricordi C, Domínguez-Bendala J. Cell replacement strategies aiming at reconstitution of the beta cell compartment in type 1 diabetes. Diabetes 2014; 63(5):1433944
5) Orlando G, Stratta R J, Light J. Pancreas transplantation for type 2 diabetes mellitus. Curr Op Org Transpl 2011; 16:1109115
6) American Diabetes Association. Diagnosis and classification of diabetes mellitus. Diabetes Care 2009; 32 (Suppl 1):S62-S67
7) Esmatjes E, Fernandez C, Rueda S, Nicolau J, Chiganer G, Ricart M J, Junca E, Fernandez-Cruz L. The utility of the C9peptide in the phenotyping of patient candidates for pancreas transplantation. Clin Transplant 2007; 21:358-362

8) Wilkin T J. The accelerator hypothesis: a review of the evidence for insulin resistance as the basis for type I as well as type II diabetes. Int J Obes (Lond) 2009; 33:716-726
9) Orlando G, Soker S, Stratta R J. Organ bioengineering and regeneration as the new Holy Grail of organ transplantation Ann Surg. 2013 August; 258(2):221932.
10) Orlando G, Wood K J, De Coppi P, Baptista P M, Binder K W, Bitar K N, Breuer C, Burnett L, Christ G, Farney A, Figliuzzi M, Holmes J H IV, Koch K, Macchiarini P, Mirmalek9Sani S H, Opara E, Remuzzi A, Rogers J, Saul J M, Seliktar D S, Shapira9Schweitzer K, Smith T, Solomon D, Van Dyke M, Yoo J J, Zhang Y, Atala A, Stratta R J, Soker S. Regenerative medicine as applied to general surgery. Ann Surg 2012; 255:8679880.
11) Orlando G. Immunosuppression9free transplantation reconsidered from a regenerative medicine perspective. Exp Rev Clin Immun 2012:8:1799187.
12) Orlando G, Wood K J, Soker S, Stratta R J. How regenerative medicine may contribute to the achievement of an immunosuppression9free state. Transplantation 2011; 92(8):e3698.
13) Orlando G. Transplantation as a subfield of regenerative medicine. An interview by Lauren Constable. Expert Rev Clin Immunol 2011; 7:1379141.
14) Orlando G, Wood K J, Stratta R J, Yoo J, Atala A, Soker S. Regenerative medicine and organ transplantation: Past, present and future. Transplantation 2011; 91:131097.
15) Orlando G, Baptista P, Birchall M, Di Coppi P, Farney A, Opara E, Rogers J, Seliktar D, Shapira-Schweitzer K, Stratta R J, Atala A, Wood K J, Soker S. Regenerative medicine as applied to solid organ transplantation: current status and future development. Transpl Int 2011; 24:2239232.
16) Badylak S F, Weiss D J, Caplan A, Macchiarini P. Engineered whole organs and complex tissues. Lancet 2012; 379(9819):943952.
17) Badylak S F, Taylor D, Uygun K. Whole9organ tissue engineering: decellularization and recellularization of three-dimensional matrix scaffolds. Ann Rev Biomed Eng 2011; 13:27953.
18) Soto-Gutierrez A, Wertheim J A, Ott H C, Gilbert T W. Perspectives on whole9organ assembly: moving toward transplantation on demand. J Clin Invest 2012; 122(11): 3817923.
19) Salvatori M, Peloso A, Katari R, Zambon J P, Soker S, Stratta R J, Orlando G. Semi-xenotransplantation: combining transplantation with organ bioengineering and regeneration technologies to manufacture complex modular organs. Xenotransplantation, Jul. 8, 2014. doi: 10.111/ xen.12122.
20) Mirmalek9Sani A, Orlando G, McQuilling J, Pareta R, Mack D, Salvatori M, Farney A C, Stratta R J, Atala A, Opara E C, Soker S. Porcine pancreas extracellular matrix as a platform for endocrine pancreas bioengineering. Biomaterials 2013; 34(22):5488995.
21) Orlando G, Farney A, Sullivan D C, AbouShwareb T, Iskandar S, Wood K J, Atala A, Stratta R J, Yoo J J, Soker S. Production and implantation of renal extracellular matrix scaffolds from porcine kidneys as a platform for renal bioengineering investigations. Ann Surg 2012; 256 (2):363970.
22) Orlando G, Booth C L, Wang Z, Totonelli G, Ross C L, Moran E, Salvatori M, Maghsoudlou P, Turmaine M, Delario G, Al9Shraideh Y, Farooq U, Farney A C, Rogers J, Iskandar S S, Burns A, Marini F C, De Coppi P, Stratta R J, Soker S. Discarded human kidneys as a source of ECM scaffolds for kidney regeneration technologies. Biomaterials 2013; 34:5915925.
23) Baiguera S, Macchiarini P, Ribatti D. Chorioallantoic membrane for in vivo investigation of tissue-engineered construct biocompatibily. J Biomed Mater Res 2012; 100: 1425e34
24) Totinelli G, Maghsaudlou P, Garriboli M, Riegler J, Orlando G, Burns A J, Sebire N J, Smith V V, Fishman J M, Ghionzoli M, Turmaine M, Birchall M A, Atala A, Soker S, Lythgoe M F, Seifalian A, Pierro A, Eaton S, De Coppi P. A rat decellularized small bowel scaffold that preserves villus crypt architecture for intestinal regeneration. Biomaterials 2012; 33(12): 3401e10.
25) Navone S E, Marfia G, Invernici G, Cristini S, Nava S, Balbi S, Sangiorgi S, Ciusani E, Bosutti A, Alessandri G, Slevin M, Parati E A. Isolation and expansion of human and mouse brain microvascular endothelial cells. Nat Protoc 2013; 8(9):1680993.
26) Salvatori M, Peloso A, Zambon J P, Patel T, Orlando G. Extracellular Matrix Scaffold Technology for Bioartificial Pancreas Engineering: State of the Art and Future Challenges. J Diabetes Sci Technol 2014; 8(1):1599169.

Each of the references cited herein is incorporated by reference herein in its entirety, or in relevant part, as would be apparent from the context of its citation.

From the disclosure herein it will be appreciated that, although specific embodiments of the disclosure have been described herein for purposes of illustration, various modifications may be made without deviating from the spirit and scope of the disclosure.

What is claimed is:

1. A method of decellularizing a human organ that is diseased, injured, damaged, or discarded for a medical reason comprising:
   (a) Perfusing an ex vivo organ that is diseased, injured, damaged, or discarded for a medical reason with at least 50 volumes of a detergent, wherein the volume is the volume of the organ being perfused; and
   (b) Rinsing the ex vivo organ with at least 50 volumes of a neutral buffer, wherein the perfusing and rinsing are performed using at least two different fluid inlets and at least one different fluid outlet.

2. The method according to claim 1 wherein the organ is selected from the group consisting of kidney, pancreas, and liver.

3. The method according to claim 1 wherein the flow rate of the two fluid inlets is about equal.

4. The method according to claim 1 further comprising an initial step of delivering distilled water to the organ at a rate of about 12 ml per minute for at least 10 hours.

5. The method according to claim 1 further comprising delivering at least one liter of 0.0025 w/w % DNase solution to the detergent-treated organ prior to rinsing the organ.

6. The method according to claim 1 wherein the detergent is sodium dodecyl sulfate or 214-(2,4,4-trimethylpentan-2-yl)phenoxylethanol.

7. The method according to claim 1 further comprising exposing the organ to a bactericidal agent.

8. The method according to claim 7 wherein the bactericidal agent is povidone-iodine.

9. The method according to claim 1 wherein the neutral buffer contains 10 U/ml heparin.

10. The method according to claim 1 wherein at least one fluid inlet and the fluid outlet are derived from different vessel systems.

11. The method according to claim 10 wherein the at least one fluid inlet is an artery and the fluid outlet is a vein or duct.

12. The method according to claim 1 wherein the organ is diseased.

13. The method according to claim 1 wherein the organ is damaged.

14. The method according to claim 1 wherein the organ has been discarded for a medical reason.

15. The method according to claim 1 further comprising attaching the organ scaffold to an antibody product specifically binding to the cell or to an anti-thrombotic composition.

16. The method according to claim 15 wherein the organ scaffold is attached to an antibody product.

17. The method according to claim 16 wherein the antibody product comprises an antigen binding site for CD31.

* * * * *